us007754431B2

United States Patent
Ring et al.

(10) Patent No.: US 7,754,431 B2
(45) Date of Patent: Jul. 13, 2010

(54) TLE3 AS A MARKER FOR CHEMOTHERAPY

(75) Inventors: Brian Z. Ring, Foster City, CA (US); Douglas T. Ross, Burlingame, CA (US); Robert S. Seitz, Hampton Cove, AL (US); Rodney A. Beck, Harvest, AL (US)

(73) Assignee: Applied Genomics, Inc., Huntsville, AL (US)

( * ) Notice: Subject to any disclaimer, the term of this patent is extended or adjusted under 35 U.S.C. 154(b) by 0 days.

(21) Appl. No.: 12/578,255

(22) Filed: Oct. 13, 2009

(65) Prior Publication Data

US 2010/0062444 A1    Mar. 11, 2010

Related U.S. Application Data

(63) Continuation of application No. 12/277,920, filed on Nov. 25, 2008.

(60) Provisional application No. 60/991,487, filed on Nov. 30, 2007.

(51) Int. Cl.
   *C12Q 1/68*   (2006.01)
   *G01N 33/48*  (2006.01)
(52) U.S. Cl. .................. 435/6; 436/63; 436/64
(58) Field of Classification Search ............ None
   See application file for complete search history.

(56) References Cited

U.S. PATENT DOCUMENTS

| 5,637,471 | A | 6/1997 | Artavanis-Tsakonas et al. |
|---|---|---|---|
| 2004/0029114 | A1 | 2/2004 | Mack et al. |
| 2004/0038207 | A1 | 2/2004 | Orntoft |
| 2004/0072154 | A1 | 4/2004 | Morris et al. |
| 2004/0156854 | A1 | 8/2004 | Mulligan et al. |
| 2004/0253606 | A1 | 12/2004 | Aziz et al. |
| 2005/0181375 | A1 | 8/2005 | Aziz et al. |
| 2006/0121511 | A1 | 6/2006 | Lee et al. |
| 2006/0234287 | A1 | 10/2006 | Erlander et al. |
| 2006/0286586 | A1 | 12/2006 | Drexhage et al. |
| 2007/0037145 | A1 | 2/2007 | Morris et al. |
| 2007/0059706 | A1 | 3/2007 | Yu et al. |
| 2007/0065888 | A1 | 3/2007 | Ring et al. |
| 2007/0172844 | A1 | 7/2007 | Lancaster et al. |
| 2007/0178090 | A1 | 8/2007 | Sukumar et al. |
| 2007/0237770 | A1 | 10/2007 | Lai et al. |
| 2008/0318228 | A1 | 12/2008 | Lee et al. |
| 2009/0004173 | A1 | 1/2009 | Evans et al. |
| 2009/0092973 | A1 | 4/2009 | Erlander et al. |
| 2009/0105167 | A1 | 4/2009 | Potti et al. |

FOREIGN PATENT DOCUMENTS

| EP | 1538218 A1 | 6/2005 |
|---|---|---|
| WO | WO-9407522 A1 | 4/1994 |
| WO | WO-9408037 A1 | 4/1994 |
| WO | WO 2004/053066 A2 | 6/2004 |
| WO | WO-2005054513 A2 | 6/2005 |
| WO | WO 2006/089233 A2 | 8/2006 |
| WO | WO-2006125195 A2 | 11/2006 |

OTHER PUBLICATIONS

Leo, Di et al., 2002, "Predictive molecular markers in the adjuvant therapy of breast cancer: state of the art in the year 2002," *Int. J. Clin. Oncol.*, 7:245-53.
Ross, DT et al., 2007, "A differentiation based immunohistochemical classifier that is prognostic for head and neck tumor patients," *Modern Pathology*, 20(2S):228A.
Nakaya, HI et al., 2007, "Splice variants of TLE family genes and up-regulation of a TLE3 isoform in prostate tumors," *Biochemical and Biophysical Research Communications*, 364(4):918-923.
International Search Report for PCT/US2008/084685, Nov. 25, 2008.
National Institutes of Health Consensus Development Panel, 2001, "NIH Consensus Development Conference Statement: Adjuvant Therapy for Breast Cancer, Nov. 1-3, 2000," *J. Nat. Cancer Inst. Monographs*, 30:5-15.
Kulkarni, S. et al., 2008, "TLE3 as a biomarker for taxane sensitivity in breast cancer," *J. Clinical Oncology*, 26(15S):573.
Kulkarni, SA et al., 2009, "TLE3 as a candidate biomarker of response to taxane therapy," *Breast Cancer Research*, 11(2):R17.
Paik et al., 2000, "HER2 and choice of adjuvant chemotherapy for invasive breast cancer: National Surgical Adjuvant Breast and Bowel Project Protocol B-15," *J. Nat'l Cancert Institute*, 92(24):1991-1998.
United Kingdom Search Report, GB0910374.8, Aug. 7, 2007.
Ton, Van Agthoven et al., 2009, "Relevance of breast cancer antiestrogen resistance genes in human breast cancer progression and tamoxifen resistance," *J. Clin. Oncology*, 27(4):542-549.

*Primary Examiner*—Sarae Bausch
(74) *Attorney, Agent, or Firm*—Choate Hall & Stewart LLP; Charles E. Lyon; Katherine Nicole Clouse

(57) ABSTRACT

Methods of using TLE3 as a marker for predicting the likelihood that a patient's cancer will respond to chemotherapy. Methods of using TLE3 as a marker for selecting a chemotherapy for a cancer.

17 Claims, 18 Drawing Sheets

SEQUENCE LISTING

<160> NUMBER OF SEQ ID NOS: 404

<210> SEQ ID NO 1
<211> LENGTH: 20
<212> TYPE: PRT
<213> ORGANISM: Homo sapiens

<400> SEQUENCE: 1

Thr Glu Glu Ser Ile Asn Asp Glu Asp Ile Tyr Lys Gly Leu Pro Asp
1               5                   10                  15

Leu Ile Asp Glu
        20

<210> SEQ ID NO 2
<211> LENGTH: 15
<212> TYPE: PRT
<213> ORGANISM: Homo sapiens

<400> SEQUENCE: 2

Glu Lys Arg Thr Asn Gly Leu Arg Arg Thr Pro Lys Gln Val Asp
1               5                   10                  15

<210> SEQ ID NO 3
<211> LENGTH: 13
<212> TYPE: PRT
<213> ORGANISM: Homo sapiens

<400> SEQUENCE: 3

Asp Tyr Ile Ser Lys Ser Lys Glu Asp Val Lys Leu Lys
1               5                   10

<210> SEQ ID NO 4
<211> LENGTH: 18
<212> TYPE: PRT
<213> ORGANISM: Homo sapiens

```
<400> SEQUENCE: 4

Glu Lys Thr Gly Val Cys Pro Glu Leu Gln Ala Asp Gln Asn Cys Thr
1               5                   10                  15

Gln Glu

<210> SEQ ID NO 5
<211> LENGTH: 14
<212> TYPE: PRT
<213> ORGANISM: Homo sapiens

<400> SEQUENCE: 5

Pro Asn Asp Lys Glu Gly Ser Cys Pro Gln Val Asn Ile Asn
1               5                   10

<210> SEQ ID NO 6
<211> LENGTH: 15
<212> TYPE: PRT
<213> ORGANISM: Homo sapiens

<400> SEQUENCE: 6

Arg Asp Gln Cys Gln Val Asp Thr Gln Cys Pro Gly Gln Met Lys
1               5                   10                  15

<210> SEQ ID NO 7
<211> LENGTH: 19
<212> TYPE: PRT
<213> ORGANISM: Homo sapiens

<400> SEQUENCE: 7

Ser Lys Thr Ile Asn Pro Gln Val Ser Lys Thr Glu Tyr Lys Glu Leu
1               5                   10                  15

Leu Gln Glu

<210> SEQ ID NO 8
<211> LENGTH: 15
<212> TYPE: PRT
<213> ORGANISM: Homo sapiens

<400> SEQUENCE: 8

Asp Asp Asn Ala Thr Thr Asn Ala Ile Asp Glu Leu Lys Glu Cys
1               5                   10                  15

<210> SEQ ID NO 9
<211> LENGTH: 15
<212> TYPE: PRT
<213> ORGANISM: Homo sapiens

<400> SEQUENCE: 9

Asn Gln Thr Asp Glu Thr Leu Ser Asn Val Glu Val Phe Met Gln
1               5                   10                  15

<210> SEQ ID NO 10
<211> LENGTH: 19
<212> TYPE: PRT
<213> ORGANISM: Homo sapiens

<400> SEQUENCE: 10

Ser Ser Asp Asp Gly Ile Arg Pro Leu Pro Glu Tyr Ser Thr Glu Lys
1               5                   10                  15

His Lys Lys

<210> SEQ ID NO 11
```

```
<211> LENGTH: 17
<212> TYPE: PRT
<213> ORGANISM: Homo sapiens

<400> SEQUENCE: 11

Asp Gly Lys Ser Lys Asp Lys Pro Pro Lys Arg Lys Lys Ala Asp Thr
1               5                   10                  15

Glu

<210> SEQ ID NO 12
<211> LENGTH: 15
<212> TYPE: PRT
<213> ORGANISM: Homo sapiens

<400> SEQUENCE: 12

Asn Lys Thr Lys Lys Lys Lys Ser Ser Arg Leu Pro Pro Glu Lys
1               5                   10                  15

<210> SEQ ID NO 13
<211> LENGTH: 18
<212> TYPE: PRT
<213> ORGANISM: Homo sapiens

<400> SEQUENCE: 13

Lys Asn Lys Glu Pro Leu Thr Lys Lys Gly Glu Thr Lys Thr Ala Glu
1               5                   10                  15

Arg Asp

<210> SEQ ID NO 14
<211> LENGTH: 17
<212> TYPE: PRT
<213> ORGANISM: Homo sapiens

<400> SEQUENCE: 14

Lys Leu Thr Cys Thr Asp Leu Asp Ser Ser Pro Arg Ser Phe Arg Tyr
1               5                   10                  15

Ser

<210> SEQ ID NO 15
<211> LENGTH: 17
<212> TYPE: PRT
<213> ORGANISM: Homo sapiens

<400> SEQUENCE: 15

Glu Val Asp Tyr Glu Asn Pro Ser Asn Leu Ala Ala Gly Asn Lys Tyr
1               5                   10                  15

Thr

<210> SEQ ID NO 16
<211> LENGTH: 20
<212> TYPE: PRT
<213> ORGANISM: Homo sapiens

<400> SEQUENCE: 16

Lys Thr Leu Gln Val Phe Asn Pro Leu Arg Phe Ser Arg Glu Asn Ser
1               5                   10                  15

Glu Lys Ile His
            20

<210> SEQ ID NO 17
<211> LENGTH: 15
<212> TYPE: PRT
```

<213> ORGANISM: Homo sapiens

<400> SEQUENCE: 17

Gln His Phe Ala Ile Ile Glu Cys Lys Val Ala Val Ala Leu Thr
1               5                   10                  15

<210> SEQ ID NO 18
<211> LENGTH: 17
<212> TYPE: PRT
<213> ORGANISM: Homo sapiens

<400> SEQUENCE: 18

Arg Lys Phe Leu Ala Pro Asp His Ser Arg Pro Pro Gln Pro Val Arg
1               5                   10                  15

Gln

<210> SEQ ID NO 19
<211> LENGTH: 18
<212> TYPE: PRT
<213> ORGANISM: Homo sapiens

<400> SEQUENCE: 19

Met Ala Lys Ala Glu Val Lys Leu Ala Ile Phe Gly Arg Ala Gly Val
1               5                   10                  15

Gly Lys

<210> SEQ ID NO 20
<211> LENGTH: 16
<212> TYPE: PRT
<213> ORGANISM: Homo sapiens

<400> SEQUENCE: 20

Val Leu Pro Leu Lys Asn Ile Leu Asp Glu Ile Lys Lys Pro Lys Asn
1               5                   10                  15

<210> SEQ ID NO 21
<211> LENGTH: 17
<212> TYPE: PRT
<213> ORGANISM: Homo sapiens

<400> SEQUENCE: 21

Tyr Glu Leu Cys Arg Glu Val Arg Arg Arg Met Val Gln Gly Lys
1               5                   10                  15

Thr

<210> SEQ ID NO 22
<211> LENGTH: 19
<212> TYPE: PRT
<213> ORGANISM: Homo sapiens

<400> SEQUENCE: 22

Thr Lys Pro Thr Thr Ile Ile Glu Lys Asn Gly Asp Ile Leu Thr Leu
1               5                   10                  15

Lys Thr His

<210> SEQ ID NO 23
<211> LENGTH: 15
<212> TYPE: PRT
<213> ORGANISM: Homo sapiens

<400> SEQUENCE: 23

Lys Asn Thr Glu Ile Ser Phe Lys Leu Gly Val Glu Phe Asp Glu

```
                 1               5                  10                 15

<210> SEQ ID NO 24
<211> LENGTH: 15
<212> TYPE: PRT
<213> ORGANISM: Homo sapiens

<400> SEQUENCE: 24

His Leu Gln Lys Trp Asp Gly Gln Glu Thr Thr Leu Val Arg Glu
 1               5                  10                 15

<210> SEQ ID NO 25
<211> LENGTH: 21
<212> TYPE: PRT
<213> ORGANISM: Homo sapiens

<400> SEQUENCE: 25

Asp Gly Asn Asp Val Glu Phe Thr Trp Leu Arg Gly Asn Asp Ser Val
 1               5                  10                 15

Arg Gly Leu Glu His
             20

<210> SEQ ID NO 26
<211> LENGTH: 19
<212> TYPE: PRT
<213> ORGANISM: Homo sapiens

<400> SEQUENCE: 26

Leu Gln Gln Met Ala Ala Lys Asp Arg Gly Thr Thr Lys Glu Val Glu
 1               5                  10                 15

Glu Val Ser

<210> SEQ ID NO 27
<211> LENGTH: 20
<212> TYPE: PRT
<213> ORGANISM: Homo sapiens

<400> SEQUENCE: 27

Lys Arg Lys Ile Ser Phe Ala Ser Ile Glu Ile Ser Ser Asp Asn Val
 1               5                  10                 15

Asp Tyr Ser Asp
             20

<210> SEQ ID NO 28
<211> LENGTH: 19
<212> TYPE: PRT
<213> ORGANISM: Homo sapiens

<400> SEQUENCE: 28

Gln Arg Gln Gln Ile Ala Lys Ser Phe Lys Ala Gln Phe Gly Lys Asp
 1               5                  10                 15

Leu Thr Glu

<210> SEQ ID NO 29
<211> LENGTH: 20
<212> TYPE: PRT
<213> ORGANISM: Homo sapiens

<400> SEQUENCE: 29

Arg Glu Ile Met Lys Ala Tyr Glu Glu Asp Tyr Gly Ser Ser Leu Glu
 1               5                  10                 15

Glu Asp Ile Gln
```

-continued

```
                    20

<210> SEQ ID NO 30
<211> LENGTH: 18
<212> TYPE: PRT
<213> ORGANISM: Homo sapiens

<400> SEQUENCE: 30

Glu Glu Tyr Glu Lys Ile Ala Asn Lys Ser Ile Glu Asp Ser Ile Lys
1               5                   10                  15

Ser Glu

<210> SEQ ID NO 31
<211> LENGTH: 21
<212> TYPE: PRT
<213> ORGANISM: Homo sapiens

<400> SEQUENCE: 31

Glu Gly Gly Ser Leu Val Pro Ala Ala Arg Gln Gln His Cys Thr Gln
1               5                   10                  15

Val Arg Ser Arg Arg
            20

<210> SEQ ID NO 32
<211> LENGTH: 15
<212> TYPE: PRT
<213> ORGANISM: Homo sapiens

<400> SEQUENCE: 32

Arg Lys Ala Gly Lys Ser Lys Lys Ser Ser Arg Lys Glu Ala Glu
1               5                   10                  15

<210> SEQ ID NO 33
<211> LENGTH: 16
<212> TYPE: PRT
<213> ORGANISM: Homo sapiens

<400> SEQUENCE: 33

Lys Thr His Glu Lys Tyr Gly Trp Val Thr Pro Pro Val Ser Asp Gly
1               5                   10                  15

<210> SEQ ID NO 34
<211> LENGTH: 15
<212> TYPE: PRT
<213> ORGANISM: Homo sapiens

<400> SEQUENCE: 34

Met Asp Leu Glu Gly Asp Arg Asn Gly Gly Ala Lys Lys Lys Asn
1               5                   10                  15

<210> SEQ ID NO 35
<211> LENGTH: 19
<212> TYPE: PRT
<213> ORGANISM: Homo sapiens

<400> SEQUENCE: 35

Asn Leu Glu Asp Leu Met Ser Asn Ile Thr Asn Arg Ser Asp Ile Asn
1               5                   10                  15

Asp Thr Gly

<210> SEQ ID NO 36
<211> LENGTH: 15
<212> TYPE: PRT
```

<213> ORGANISM: Homo sapiens

<400> SEQUENCE: 36

Arg Gly Ser Gln Ala Gln Asp Arg Lys Leu Ser Thr Lys Glu Ala
1               5                   10                  15

<210> SEQ ID NO 37
<211> LENGTH: 18
<212> TYPE: PRT
<213> ORGANISM: Homo sapiens

<400> SEQUENCE: 37

Met Asp Leu Glu Ala Ala Lys Asn Gly Thr Ala Trp Arg Pro Thr Ser
1               5                   10                  15

Ala Glu

<210> SEQ ID NO 38
<211> LENGTH: 17
<212> TYPE: PRT
<213> ORGANISM: Homo sapiens

<400> SEQUENCE: 38

Asn Phe Ser Phe Pro Val Asn Phe Ser Leu Ser Leu Leu Asn Pro Gly
1               5                   10                  15

Lys

<210> SEQ ID NO 39
<211> LENGTH: 16
<212> TYPE: PRT
<213> ORGANISM: Homo sapiens

<400> SEQUENCE: 39

Lys Asn Ser Gln Met Cys Gln Lys Ser Leu Asp Val Glu Thr Asp Gly
1               5                   10                  15

<210> SEQ ID NO 40
<211> LENGTH: 13
<212> TYPE: PRT
<213> ORGANISM: Homo sapiens

<400> SEQUENCE: 40

Met Ala Leu Arg Gly Phe Cys Ser Ala Asp Gly Ser Asp
1               5                   10

<210> SEQ ID NO 41
<211> LENGTH: 16
<212> TYPE: PRT
<213> ORGANISM: Homo sapiens

<400> SEQUENCE: 41

Lys Asn Trp Lys Lys Glu Cys Ala Lys Thr Arg Lys Gln Pro Val Lys
1               5                   10                  15

<210> SEQ ID NO 42
<211> LENGTH: 16
<212> TYPE: PRT
<213> ORGANISM: Homo sapiens

<400> SEQUENCE: 42

Asp Ser Ile Glu Arg Arg Pro Val Lys Asp Gly Gly Thr Asn Ser
1               5                   10                  15

<210> SEQ ID NO 43

```
<211> LENGTH: 20
<212> TYPE: PRT
<213> ORGANISM: Homo sapiens

<400> SEQUENCE: 43

Met Leu Glu Lys Phe Cys Asn Ser Thr Phe Trp Asn Ser Ser Phe Leu
1               5                   10                  15

Asp Ser Pro Glu
            20

<210> SEQ ID NO 44
<211> LENGTH: 15
<212> TYPE: PRT
<213> ORGANISM: Homo sapiens

<400> SEQUENCE: 44

Ser Ile Leu Cys Gly Thr Phe Gln Phe Gln Thr Leu Ile Arg Thr
1               5                   10                  15

<210> SEQ ID NO 45
<211> LENGTH: 14
<212> TYPE: PRT
<213> ORGANISM: Homo sapiens

<400> SEQUENCE: 45

Glu Asn Asn Glu Ser Ser Asn Asn Pro Ser Ser Ile Ala Ser
1               5                   10

<210> SEQ ID NO 46
<211> LENGTH: 16
<212> TYPE: PRT
<213> ORGANISM: Homo sapiens

<400> SEQUENCE: 46

Gln Glu Val Lys Pro Asn Pro Leu Gln Asp Ala Asn Ile Cys Ser Arg
1               5                   10                  15

<210> SEQ ID NO 47
<211> LENGTH: 16
<212> TYPE: PRT
<213> ORGANISM: Homo sapiens

<400> SEQUENCE: 47

Asp Glu Ile Ser Gln Arg Asn Arg Gln Leu Pro Ser Asp Gly Lys Lys
1               5                   10                  15

<210> SEQ ID NO 48
<211> LENGTH: 18
<212> TYPE: PRT
<213> ORGANISM: Homo sapiens

<400> SEQUENCE: 48

Val Gln Asp Phe Thr Ala Phe Trp Asp Lys Ala Ser Glu Thr Pro Thr
1               5                   10                  15

Leu Gln

<210> SEQ ID NO 49
<211> LENGTH: 18
<212> TYPE: PRT
<213> ORGANISM: Homo sapiens

<400> SEQUENCE: 49

Met Asp Ala Leu Cys Gly Ser Gly Glu Leu Gly Ser Lys Phe Trp Asp
1               5                   10                  15
```

<210> SEQ ID NO 50
<211> LENGTH: 15
<212> TYPE: PRT
<213> ORGANISM: Homo sapiens

<400> SEQUENCE: 50

Arg Lys Gln Glu Lys Gln Thr Ala Arg His Lys Ala Ser Ala Ala
1               5                   10                  15

<210> SEQ ID NO 51
<211> LENGTH: 13
<212> TYPE: PRT
<213> ORGANISM: Homo sapiens

<400> SEQUENCE: 51

Asp Pro Gln Ser Val Glu Arg Lys Thr Ile Ser Pro Gly
1               5                   10

<210> SEQ ID NO 52
<211> LENGTH: 19
<212> TYPE: PRT
<213> ORGANISM: Homo sapiens

<400> SEQUENCE: 52

Met Lys Asp Ile Asp Ile Gly Lys Glu Tyr Ile Ile Pro Ser Pro Gly
1               5                   10                  15

Tyr Arg Ser

<210> SEQ ID NO 53
<211> LENGTH: 18
<212> TYPE: PRT
<213> ORGANISM: Homo sapiens

<400> SEQUENCE: 53

Arg Asp Arg Glu Asp Ser Lys Phe Arg Arg Thr Arg Pro Leu Glu Cys
1               5                   10                  15

Gln Asp

<210> SEQ ID NO 54
<211> LENGTH: 15
<212> TYPE: PRT
<213> ORGANISM: Homo sapiens

<400> SEQUENCE: 54

Ser Lys His Glu Ser Ser Asp Val Asn Cys Arg Arg Leu Glu Arg
1               5                   10                  15

<210> SEQ ID NO 55
<211> LENGTH: 20
<212> TYPE: PRT
<213> ORGANISM: Homo sapiens

<400> SEQUENCE: 55

Met Ala Ala Pro Ala Glu Pro Cys Ala Gly Gln Gly Val Trp Asn Gln
1               5                   10                  15

Thr Glu Pro Glu
            20

<210> SEQ ID NO 56
<211> LENGTH: 17

```
<212> TYPE: PRT
<213> ORGANISM: Homo sapiens

<400> SEQUENCE: 56

Asp Pro Gly Val Val Asp Ser Ser Ser Gly Ser Ala Ala Gly Lys
1               5                   10                  15

Ser

<210> SEQ ID NO 57
<211> LENGTH: 13
<212> TYPE: PRT
<213> ORGANISM: Homo sapiens

<400> SEQUENCE: 57

His Thr Leu Val Ala Glu Asn Ala Met Asn Ala Glu Lys
1               5                   10

<210> SEQ ID NO 58
<211> LENGTH: 18
<212> TYPE: PRT
<213> ORGANISM: Homo sapiens

<400> SEQUENCE: 58

Met Ser Asp Ser Val Ile Leu Arg Ser Ile Lys Lys Phe Gly Glu Glu
1               5                   10                  15

Asn Asp

<210> SEQ ID NO 59
<211> LENGTH: 14
<212> TYPE: PRT
<213> ORGANISM: Homo sapiens

<400> SEQUENCE: 59

Thr Asn Ser Ser Leu Asn Gln Asn Met Thr Asn Gly Thr Arg
1               5                   10

<210> SEQ ID NO 60
<211> LENGTH: 15
<212> TYPE: PRT
<213> ORGANISM: Homo sapiens

<400> SEQUENCE: 60

Gln Glu Val Leu Ser Lys Ile Gln His Gly His Thr Ile Ile Ser
1               5                   10                  15

<210> SEQ ID NO 61
<211> LENGTH: 15
<212> TYPE: PRT
<213> ORGANISM: Homo sapiens

<400> SEQUENCE: 61

Gly Ala Asp Asp Pro Ser Ser Val Thr Ala Glu Glu Ile Gln Arg
1               5                   10                  15

<210> SEQ ID NO 62
<211> LENGTH: 14
<212> TYPE: PRT
<213> ORGANISM: Homo sapiens

<400> SEQUENCE: 62

Asn Ala Val Ala Ser Pro Glu Phe Pro Pro Arg Phe Asn Thr
1               5                   10
```

<210> SEQ ID NO 63
<211> LENGTH: 18
<212> TYPE: PRT
<213> ORGANISM: Homo sapiens

<400> SEQUENCE: 63

Lys Pro Asn Gly Ile Tyr Arg Lys Leu Met Asn Lys Gln Ser Phe Ile
1               5                   10                  15

Ser Ala

<210> SEQ ID NO 64
<211> LENGTH: 13
<212> TYPE: PRT
<213> ORGANISM: Homo sapiens

<400> SEQUENCE: 64

Met Ala Ser Ser Arg Cys Pro Ala Pro Arg Gly Cys Arg
1               5                   10

<210> SEQ ID NO 65
<211> LENGTH: 10
<212> TYPE: PRT
<213> ORGANISM: Homo sapiens

<400> SEQUENCE: 65

Gln Gly Gly Ser Gly Asn Pro Val Arg Arg
1               5                   10

<210> SEQ ID NO 66
<211> LENGTH: 17
<212> TYPE: PRT
<213> ORGANISM: Homo sapiens

<400> SEQUENCE: 66

Glu Phe Val Gly Asp Gly Ile Tyr Asn Asn Thr Met Gly His Val His
1               5                   10                  15

Ser

<210> SEQ ID NO 67
<211> LENGTH: 16
<212> TYPE: PRT
<213> ORGANISM: Homo sapiens

<400> SEQUENCE: 67

Met Pro Leu Ala Phe Cys Gly Ser Glu Asn His Ser Ala Ala Tyr Arg
1               5                   10                  15

<210> SEQ ID NO 68
<211> LENGTH: 18
<212> TYPE: PRT
<213> ORGANISM: Homo sapiens

<400> SEQUENCE: 68

Asp His Leu Gly Lys Glu Asn Asp Val Phe Gln Pro Lys Thr Gln Phe
1               5                   10                  15

Leu Gly

<210> SEQ ID NO 69
<211> LENGTH: 16
<212> TYPE: PRT
<213> ORGANISM: Homo sapiens

<400> SEQUENCE: 69

-continued

Glu Ile Arg Glu Glu Gln Cys Ala Pro His Glu Pro Thr Pro Gln Gly
1               5                   10                  15

<210> SEQ ID NO 70
<211> LENGTH: 12
<212> TYPE: PRT
<213> ORGANISM: Homo sapiens

<400> SEQUENCE: 70

Met Ser Leu Ser Phe Cys Gly Asn Asn Ile Ser Ser
1               5                   10

<210> SEQ ID NO 71
<211> LENGTH: 18
<212> TYPE: PRT
<213> ORGANISM: Homo sapiens

<400> SEQUENCE: 71

Gln Arg Val Asn Glu Thr Gln Asn Gly Thr Asn Asn Thr Thr Gly Ile
1               5                   10                  15

Ser Glu

<210> SEQ ID NO 72
<211> LENGTH: 19
<212> TYPE: PRT
<213> ORGANISM: Homo sapiens

<400> SEQUENCE: 72

Asp Glu Ile Gly Asp Asp Ser Trp Arg Thr Gly Glu Ser Ser Leu Pro
1               5                   10                  15

Phe Glu Ser

<210> SEQ ID NO 73
<211> LENGTH: 21
<212> TYPE: PRT
<213> ORGANISM: Homo sapiens

<400> SEQUENCE: 73

Met Val Lys Val Thr Phe Asn Ser Ala Leu Ala Gln Lys Glu Ala Lys
1               5                   10                  15

Lys Asp Glu Pro Lys
            20

<210> SEQ ID NO 74
<211> LENGTH: 16
<212> TYPE: PRT
<213> ORGANISM: Homo sapiens

<400> SEQUENCE: 74

Gln Thr Ile Glu Glu Asn Ile Lys Ile Phe Glu Glu Glu Val Glu
1               5                   10                  15

<210> SEQ ID NO 75
<211> LENGTH: 21
<212> TYPE: PRT
<213> ORGANISM: Homo sapiens

<400> SEQUENCE: 75

His Asp Lys Glu Thr Tyr Lys Leu Gln Arg Arg Glu Thr Ile Lys Gly
1               5                   10                  15

Ile Gln Lys Arg Glu
            20

```
<210> SEQ ID NO 76
<211> LENGTH: 20
<212> TYPE: PRT
<213> ORGANISM: Homo sapiens

<400> SEQUENCE: 76

Met Ala His Ala Ala Ser Gln Leu Lys Lys Asn Arg Asp Leu Glu Ile
1               5                   10                  15

Asn Ala Glu Glu
            20

<210> SEQ ID NO 77
<211> LENGTH: 20
<212> TYPE: PRT
<213> ORGANISM: Homo sapiens

<400> SEQUENCE: 77

His Lys Lys Glu Thr Glu Ser Asp Gln Asp Asp Glu Ile Glu Lys Thr
1               5                   10                  15

Asp Arg Arg Gln
            20

<210> SEQ ID NO 78
<211> LENGTH: 20
<212> TYPE: PRT
<213> ORGANISM: Homo sapiens

<400> SEQUENCE: 78

Glu Gly Phe Lys Val Lys Thr Lys Lys Glu Ile Arg His Val Glu Lys
1               5                   10                  15

Lys Ser His Ser
            20

<210> SEQ ID NO 79
<211> LENGTH: 18
<212> TYPE: PRT
<213> ORGANISM: Homo sapiens

<400> SEQUENCE: 79

Glu Arg Ala Leu Ala Ala Ala Gln Arg Cys His Lys Lys Val Met Lys
1               5                   10                  15

Glu Arg

<210> SEQ ID NO 80
<211> LENGTH: 15
<212> TYPE: PRT
<213> ORGANISM: Homo sapiens

<400> SEQUENCE: 80

Thr Ala Gly Met Lys Asp Leu Leu Ser Val Phe Gln Ala Tyr Gln
1               5                   10                  15

<210> SEQ ID NO 81
<211> LENGTH: 16
<212> TYPE: PRT
<213> ORGANISM: Homo sapiens

<400> SEQUENCE: 81

Asp Pro Pro Arg Thr Val Leu Gln Ala Pro Lys Glu Trp Val Cys Leu
1               5                   10                  15

<210> SEQ ID NO 82
```

```
<211> LENGTH: 20
<212> TYPE: PRT
<213> ORGANISM: Homo sapiens

<400> SEQUENCE: 82

Met Glu Ala Ala Asp Ala Ser Arg Ser Asn Gly Ser Ser Pro Glu Ala
1               5                   10                  15

Arg Asp Ala Arg
            20

<210> SEQ ID NO 83
<211> LENGTH: 17
<212> TYPE: PRT
<213> ORGANISM: Homo sapiens

<400> SEQUENCE: 83

Glu Leu His Leu Lys Pro His Leu Glu Gly Ala Ala Phe Arg Asp His
1               5                   10                  15

Gln

<210> SEQ ID NO 84
<211> LENGTH: 18
<212> TYPE: PRT
<213> ORGANISM: Homo sapiens

<400> SEQUENCE: 84

Glu Gly Glu Gly Leu Gly Gln Ser Leu Gly Asn Phe Lys Asp Asp Leu
1               5                   10                  15

Leu Asn

<210> SEQ ID NO 85
<211> LENGTH: 17
<212> TYPE: PRT
<213> ORGANISM: Homo sapiens

<400> SEQUENCE: 85

Glu Leu His Leu Lys Pro His Leu Glu Gly Ala Ala Phe Arg Asp His
1               5                   10                  15

Gln

<210> SEQ ID NO 86
<211> LENGTH: 17
<212> TYPE: PRT
<213> ORGANISM: Homo sapiens

<400> SEQUENCE: 86

Gly Ser Glu Glu Arg Gly Ala Gly Arg Gly Ser Ser Gly Gly Arg Glu
1               5                   10                  15

Glu

<210> SEQ ID NO 87
<211> LENGTH: 18
<212> TYPE: PRT
<213> ORGANISM: Homo sapiens

<400> SEQUENCE: 87

Lys Ile Trp Ser Leu Ala Glu Thr Ala Thr Ser Pro Asp Asn Pro Arg
1               5                   10                  15

Arg Ser

<210> SEQ ID NO 88
```

-continued

<211> LENGTH: 20
<212> TYPE: PRT
<213> ORGANISM: Homo sapiens

<400> SEQUENCE: 88

Lys Lys Leu Leu Lys Thr Ala Phe Gln Pro Val Pro Arg Arg Pro Gln
1               5                   10                  15

Asn His Leu Asp
            20

<210> SEQ ID NO 89
<211> LENGTH: 21
<212> TYPE: PRT
<213> ORGANISM: Homo sapiens

<400> SEQUENCE: 89

Arg Arg Ser Ser Thr Thr His Val Lys Gln Ala Ile Asn Lys Met Leu
1               5                   10                  15

Thr Lys Ile Ser Ser
            20

<210> SEQ ID NO 90
<211> LENGTH: 20
<212> TYPE: PRT
<213> ORGANISM: Homo sapiens

<400> SEQUENCE: 90

Met Arg Arg Lys Asn Thr Cys Gln Asn Phe Met Glu Tyr Phe Cys Ile
1               5                   10                  15

Ser Leu Ala Phe
            20

<210> SEQ ID NO 91
<211> LENGTH: 21
<212> TYPE: PRT
<213> ORGANISM: Homo sapiens

<400> SEQUENCE: 91

Asn Glu Thr Ile Leu Tyr Phe Pro Phe Ser Ser His Ser Ser Tyr Thr
1               5                   10                  15

Val Arg Ser Lys Lys
            20

<210> SEQ ID NO 92
<211> LENGTH: 19
<212> TYPE: PRT
<213> ORGANISM: Homo sapiens

<400> SEQUENCE: 92

Lys Val Gln Ile Pro Ala Tyr Ile Glu Met Asn Ile Pro Leu Val Ile
1               5                   10                  15

Leu Cys Gln

<210> SEQ ID NO 93
<211> LENGTH: 18
<212> TYPE: PRT
<213> ORGANISM: Homo sapiens

<400> SEQUENCE: 93

Met Leu Thr Glu Leu Glu Lys Ala Leu Asn Ser Ile Ile Asp Val Tyr
1               5                   10                  15

His Lys

```
<210> SEQ ID NO 94
<211> LENGTH: 22
<212> TYPE: PRT
<213> ORGANISM: Homo sapiens

<400> SEQUENCE: 94

Arg Asp Asp Leu Lys Lys Leu Leu Glu Thr Glu Cys Pro Gln Tyr Ile
1               5                   10                  15

Arg Lys Lys Gly Ala Asp
            20

<210> SEQ ID NO 95
<211> LENGTH: 17
<212> TYPE: PRT
<213> ORGANISM: Homo sapiens

<400> SEQUENCE: 95

Lys Met Gly Val Ala Ala His Lys Lys Ser His Glu Ser His Lys
1               5                   10                  15

Glu

<210> SEQ ID NO 96
<211> LENGTH: 17
<212> TYPE: PRT
<213> ORGANISM: Homo sapiens

<400> SEQUENCE: 96

Pro Glu Ser Arg Lys Asp Pro Ser Gly Ala Ser Asn Pro Ser Ala Asp
1               5                   10                  15

Ser

<210> SEQ ID NO 97
<211> LENGTH: 15
<212> TYPE: PRT
<213> ORGANISM: Homo sapiens

<400> SEQUENCE: 97

His Gly Leu Ala Pro His Glu Ser Gln Leu His Leu Lys Gly Asp
1               5                   10                  15

<210> SEQ ID NO 98
<211> LENGTH: 18
<212> TYPE: PRT
<213> ORGANISM: Homo sapiens

<400> SEQUENCE: 98

Glu Gln Gln His Lys Leu Asp Phe Lys Ala Tyr Glu Gln Ala Leu Gln
1               5                   10                  15

Tyr Ser

<210> SEQ ID NO 99
<211> LENGTH: 15
<212> TYPE: PRT
<213> ORGANISM: Homo sapiens

<400> SEQUENCE: 99

His Gly Leu Ala Pro His Glu Ser Gln Leu His Leu Lys Gly Asp
1               5                   10                  15

<210> SEQ ID NO 100
<211> LENGTH: 20
```

```
<212> TYPE: PRT
<213> ORGANISM: Homo sapiens

<400> SEQUENCE: 100

Glu Glu Tyr Val Gly Leu Ser Ala Asn Gln Cys Ala Val Pro Ala Lys
1               5                   10                  15

Asp Arg Val Asp
            20

<210> SEQ ID NO 101
<211> LENGTH: 15
<212> TYPE: PRT
<213> ORGANISM: Homo sapiens

<400> SEQUENCE: 101

Arg Val Asp Cys Gly Tyr Pro His Val Thr Pro Lys Glu Cys Asn
1               5                   10                  15

<210> SEQ ID NO 102
<211> LENGTH: 15
<212> TYPE: PRT
<213> ORGANISM: Homo sapiens

<400> SEQUENCE: 102

Val Pro Trp Cys Phe Lys Pro Leu Gln Glu Ala Glu Cys Thr Phe
1               5                   10                  15

<210> SEQ ID NO 103
<211> LENGTH: 15
<212> TYPE: PRT
<213> ORGANISM: Homo sapiens

<400> SEQUENCE: 103

Val Pro Trp Cys Phe Lys Pro Leu Gln Glu Ala Glu Cys Thr Phe
1               5                   10                  15

<210> SEQ ID NO 104
<211> LENGTH: 16
<212> TYPE: PRT
<213> ORGANISM: Homo sapiens

<400> SEQUENCE: 104

Lys Lys Glu Pro Val Thr Thr Arg Gln Val Arg Thr Ile Val Glu Glu
1               5                   10                  15

<210> SEQ ID NO 105
<211> LENGTH: 17
<212> TYPE: PRT
<213> ORGANISM: Homo sapiens

<400> SEQUENCE: 105

Gln Asp Gly Lys Val Ile Ser Ser Arg Glu Gln Val His Gln Thr Thr
1               5                   10                  15

Arg

<210> SEQ ID NO 106
<211> LENGTH: 15
<212> TYPE: PRT
<213> ORGANISM: Homo sapiens

<400> SEQUENCE: 106

Ser Ser Ser Ile Lys Gly Ser Ser Gly Leu Gly Gly Gly Ser Ser
1               5                   10                  15
```

```
<210> SEQ ID NO 107
<211> LENGTH: 20
<212> TYPE: PRT
<213> ORGANISM: Homo sapiens

<400> SEQUENCE: 107

Asp Glu Glu Asp Lys Leu Arg His Phe Arg Glu Cys Phe Tyr Ile Pro
1               5                   10                  15

Lys Ile Gln Asp
            20

<210> SEQ ID NO 108
<211> LENGTH: 21
<212> TYPE: PRT
<213> ORGANISM: Homo sapiens

<400> SEQUENCE: 108

Lys Pro Arg Glu Gly Glu Glu Thr Leu Arg Ile Glu Asp Ile Leu Glu
1               5                   10                  15

Val Ile Glu Lys Glu
            20

<210> SEQ ID NO 109
<211> LENGTH: 21
<212> TYPE: PRT
<213> ORGANISM: Homo sapiens

<400> SEQUENCE: 109

Glu Glu Arg Gly Cys Gln Leu Thr Ile Thr Phe Ser Val Pro Asn Lys
1               5                   10                  15

Asp Val Phe Gln Glu
            20

<210> SEQ ID NO 110
<211> LENGTH: 20
<212> TYPE: PRT
<213> ORGANISM: Homo sapiens

<400> SEQUENCE: 110

Asp His Asn His Ala Ala Ser Gly Lys Asn Lys Arg Lys Ala Leu Cys
1               5                   10                  15

Pro Asp His Asp
            20

<210> SEQ ID NO 111
<211> LENGTH: 21
<212> TYPE: PRT
<213> ORGANISM: Homo sapiens

<400> SEQUENCE: 111

Glu Glu Pro Ala Met Glu Met Lys Arg Gly Pro Leu Phe Ser His Leu
1               5                   10                  15

Ser Ser Gln Asn Ile
            20

<210> SEQ ID NO 112
<211> LENGTH: 16
<212> TYPE: PRT
<213> ORGANISM: Homo sapiens

<400> SEQUENCE: 112

Gln Arg Tyr Ser Arg Glu Glu Leu Lys Asp Ala Gly Val Ala Thr Leu
```

-continued

```
1               5                  10                  15
```

<210> SEQ ID NO 113
<211> LENGTH: 22
<212> TYPE: PRT
<213> ORGANISM: Homo sapiens

<400> SEQUENCE: 113

Met Asp Ile Glu Ala Tyr Leu Glu Arg Ile Gly Tyr Lys Lys Ser Arg
1               5                   10                  15

Asn Lys Leu Asp Leu Glu
            20

<210> SEQ ID NO 114
<211> LENGTH: 22
<212> TYPE: PRT
<213> ORGANISM: Homo sapiens

<400> SEQUENCE: 114

Gln Met Trp Gln Pro Leu Glu Leu Ile Ser Gly Lys Asp Gln Pro Gln
1               5                   10                  15

Val Pro Cys Val Phe Arg
            20

<210> SEQ ID NO 115
<211> LENGTH: 20
<212> TYPE: PRT
<213> ORGANISM: Homo sapiens

<400> SEQUENCE: 115

Phe Asn Ile Ser Leu Gln Arg Lys Leu Val Pro Lys His Gly Asp Arg
1               5                   10                  15

Phe Phe Thr Ile
            20

<210> SEQ ID NO 116
<211> LENGTH: 21
<212> TYPE: PRT
<213> ORGANISM: Homo sapiens

<400> SEQUENCE: 116

Arg Gln Arg Leu Thr His Leu Ser Pro Glu Glu Lys Ala Leu Arg Arg
1               5                   10                  15

Lys Leu Lys Asn Arg
            20

<210> SEQ ID NO 117
<211> LENGTH: 20
<212> TYPE: PRT
<213> ORGANISM: Homo sapiens

<400> SEQUENCE: 117

Glu Lys Thr His Gly Leu Val Val Glu Asn Gln Glu Leu Arg Gln Arg
1               5                   10                  15

Leu Gly Met Asp
            20

<210> SEQ ID NO 118
<211> LENGTH: 20
<212> TYPE: PRT
<213> ORGANISM: Homo sapiens

<400> SEQUENCE: 118

-continued

```
Gln Pro Pro Phe Leu Cys Gln Trp Gly Arg His Gln Pro Ser Trp Lys
1               5                   10                  15

Pro Leu Met Asn
            20

<210> SEQ ID NO 119
<211> LENGTH: 16
<212> TYPE: PRT
<213> ORGANISM: Homo sapiens

<400> SEQUENCE: 119

Asn Lys Ile Thr Thr Glu Phe Phe Asp Pro Leu Phe Val Glu Gln Lys
1               5                   10                  15

<210> SEQ ID NO 120
<211> LENGTH: 18
<212> TYPE: PRT
<213> ORGANISM: Homo sapiens

<400> SEQUENCE: 120

Phe Ser Ile Ser Asp Asn Asn Lys Thr Pro Arg Tyr Thr Tyr Asn Gly
1               5                   10                  15

Ala Thr

<210> SEQ ID NO 121
<211> LENGTH: 18
<212> TYPE: PRT
<213> ORGANISM: Homo sapiens

<400> SEQUENCE: 121

Glu Asp Phe Lys Thr Thr Asn Pro Ser Lys Gln Phe Asp Lys Asn Ala
1               5                   10                  15

Tyr Val

<210> SEQ ID NO 122
<211> LENGTH: 20
<212> TYPE: PRT
<213> ORGANISM: Homo sapiens

<400> SEQUENCE: 122

Glu Gly Asp Ala Lys Gly Leu Lys Glu Gly Thr Pro Gly Asn Phe
1               5                   10                  15

Met Glu Asp Glu
            20

<210> SEQ ID NO 123
<211> LENGTH: 19
<212> TYPE: PRT
<213> ORGANISM: Homo sapiens

<400> SEQUENCE: 123

Glu Trp Cys Phe Cys Phe Trp Arg Glu Lys Pro Pro Cys Leu Ala Glu
1               5                   10                  15

Leu Glu Arg

<210> SEQ ID NO 124
<211> LENGTH: 16
<212> TYPE: PRT
<213> ORGANISM: Homo sapiens

<400> SEQUENCE: 124
```

```
Glu Glu Glu Gly Glu Ala Gly Glu Ala Asp Asp Gly Gly Tyr Ile Trp
1               5                   10                  15
```

<210> SEQ ID NO 125
<211> LENGTH: 13
<212> TYPE: PRT
<213> ORGANISM: Homo sapiens

<400> SEQUENCE: 125

```
Asp Lys Asp Pro Gln Lys Met Tyr Ala Thr Ile Tyr Glu
1               5                   10
```

<210> SEQ ID NO 126
<211> LENGTH: 15
<212> TYPE: PRT
<213> ORGANISM: Homo sapiens

<400> SEQUENCE: 126

```
Lys Lys Cys Asp Tyr Trp Ile Arg Thr Phe Val Pro Gly Cys Gln
1               5                   10                  15
```

<210> SEQ ID NO 127
<211> LENGTH: 15
<212> TYPE: PRT
<213> ORGANISM: Homo sapiens

<400> SEQUENCE: 127

```
Glu Asn Phe Ile Arg Phe Ser Lys Tyr Leu Gly Leu Pro Glu Asn
1               5                   10                  15
```

<210> SEQ ID NO 128
<211> LENGTH: 15
<212> TYPE: PRT
<213> ORGANISM: Homo sapiens

<400> SEQUENCE: 128

```
Asp Asp Ser Asp Gln Asp Ser Cys Arg Leu Ser Ile Asp Ser Gln
1               5                   10                  15
```

<210> SEQ ID NO 129
<211> LENGTH: 15
<212> TYPE: PRT
<213> ORGANISM: Homo sapiens

<400> SEQUENCE: 129

```
Arg Gln His Tyr Pro Glu Ala Tyr Ala Ser Pro Ser His Thr Lys
1               5                   10                  15
```

<210> SEQ ID NO 130
<211> LENGTH: 19
<212> TYPE: PRT
<213> ORGANISM: Homo sapiens

<400> SEQUENCE: 130

```
Asn Thr Pro Leu Gly Arg Asn Leu Ser Thr His Gln Thr Tyr Pro Val
1               5                   10                  15

Val Ala Asp
```

<210> SEQ ID NO 131
<211> LENGTH: 15
<212> TYPE: PRT
<213> ORGANISM: Homo sapiens

<400> SEQUENCE: 131

```
Arg Leu Val Ser Cys Pro Gly Pro Leu Asp Gln Asp Gln Gln Glu
1               5                   10                  15

<210> SEQ ID NO 132
<211> LENGTH: 19
<212> TYPE: PRT
<213> ORGANISM: Homo sapiens

<400> SEQUENCE: 132

Lys Met Ser Pro Glu Asp Ile Arg Lys Trp Asn Val Thr Ser Leu Glu
1               5                   10                  15

Thr Leu Lys

<210> SEQ ID NO 133
<211> LENGTH: 20
<212> TYPE: PRT
<213> ORGANISM: Homo sapiens

<400> SEQUENCE: 133

Ser Pro Glu Glu Leu Ser Ser Val Pro Pro Ser Ser Ile Trp Ala Val
1               5                   10                  15

Arg Pro Gln Asp
            20

<210> SEQ ID NO 134
<211> LENGTH: 17
<212> TYPE: PRT
<213> ORGANISM: Homo sapiens

<400> SEQUENCE: 134

Glu Glu Gln Asn Lys Leu Val His Gly Gly Pro Cys Asp Lys Thr Ser
1               5                   10                  15

His

<210> SEQ ID NO 135
<211> LENGTH: 16
<212> TYPE: PRT
<213> ORGANISM: Homo sapiens

<400> SEQUENCE: 135

Glu Leu Ile Gln Pro Leu Pro Leu Glu Arg Asp Cys Ser Ala Asn Thr
1               5                   10                  15

<210> SEQ ID NO 136
<211> LENGTH: 14
<212> TYPE: PRT
<213> ORGANISM: Homo sapiens

<400> SEQUENCE: 136

Gly Lys Thr Ala Asp Gly Asp Phe Pro Asp Thr Ile Gln Cys
1               5                   10

<210> SEQ ID NO 137
<211> LENGTH: 20
<212> TYPE: PRT
<213> ORGANISM: Homo sapiens

<400> SEQUENCE: 137

Arg Glu Gln Trp Pro Glu Arg Arg Cys His Arg Leu Glu Asn Gly
1               5                   10                  15

Cys Gly Asn Ala
            20
```

```
<210> SEQ ID NO 138
<211> LENGTH: 18
<212> TYPE: PRT
<213> ORGANISM: Homo sapiens

<400> SEQUENCE: 138

Ser Val Lys Glu Gln Val Glu Lys Ile Ile Cys Asn Leu Lys Pro Ala
1               5                   10                  15

Leu Lys

<210> SEQ ID NO 139
<211> LENGTH: 16
<212> TYPE: PRT
<213> ORGANISM: Homo sapiens

<400> SEQUENCE: 139

Lys Val Asn Ser Ala Gly Asp Ala Ile Gly Leu Gln Pro Asp Ala Arg
1               5                   10                  15

<210> SEQ ID NO 140
<211> LENGTH: 20
<212> TYPE: PRT
<213> ORGANISM: Homo sapiens

<400> SEQUENCE: 140

Gln Gln Leu Lys Val Ile Asp Asn Gln Arg Glu Leu Ser Arg Leu Ser
1               5                   10                  15

Arg Glu Leu Glu
            20

<210> SEQ ID NO 141
<211> LENGTH: 16
<212> TYPE: PRT
<213> ORGANISM: Homo sapiens

<400> SEQUENCE: 141

Arg Glu His Met Gln Ala Val Thr Arg Asn Tyr Ile Thr His Pro Arg
1               5                   10                  15

<210> SEQ ID NO 142
<211> LENGTH: 13
<212> TYPE: PRT
<213> ORGANISM: Homo sapiens

<400> SEQUENCE: 142

Lys Lys Ser Lys Ala Val Leu Asp Tyr His Asp Asp Asn
1               5                   10

<210> SEQ ID NO 143
<211> LENGTH: 19
<212> TYPE: PRT
<213> ORGANISM: Homo sapiens

<400> SEQUENCE: 143

Asp Glu Phe Tyr Ser Arg Glu Gly Arg Leu Gln Asp Leu Ala Pro Asp
1               5                   10                  15

Thr Ala Leu

<210> SEQ ID NO 144
<211> LENGTH: 18
<212> TYPE: PRT
<213> ORGANISM: Homo sapiens
```

```
<400> SEQUENCE: 144

Lys Gln Gln Asp Gly Pro Thr Lys Thr His Lys Leu Glu Lys Leu Met
1               5                   10                  15

Ile Arg

<210> SEQ ID NO 145
<211> LENGTH: 19
<212> TYPE: PRT
<213> ORGANISM: Homo sapiens

<400> SEQUENCE: 145

Glu Leu Arg Val Leu Ser Lys Ala Asn Ala Ile Val Pro Gly Leu Ser
1               5                   10                  15

Gly Gly Glu

<210> SEQ ID NO 146
<211> LENGTH: 20
<212> TYPE: PRT
<213> ORGANISM: Homo sapiens

<400> SEQUENCE: 146

Arg Arg Gly Gly Glu Gly Gly Glu Glu Asn Pro Ser Ala Ala Lys Gly
1               5                   10                  15

His Leu Met Gly
            20

<210> SEQ ID NO 147
<211> LENGTH: 14
<212> TYPE: PRT
<213> ORGANISM: Homo sapiens

<400> SEQUENCE: 147

Met Pro Glu Val Ser Ser Lys Gly Ala Thr Ile Ser Lys Lys
1               5                   10

<210> SEQ ID NO 148
<211> LENGTH: 11
<212> TYPE: PRT
<213> ORGANISM: Homo sapiens

<400> SEQUENCE: 148

Gly Phe Lys Lys Ala Val Val Lys Thr Gln Lys
1               5                   10

<210> SEQ ID NO 149
<211> LENGTH: 12
<212> TYPE: PRT
<213> ORGANISM: Homo sapiens

<400> SEQUENCE: 149

Lys Glu Gly Lys Lys Arg Lys Arg Thr Arg Lys Glu
1               5                   10

<210> SEQ ID NO 150
<211> LENGTH: 18
<212> TYPE: PRT
<213> ORGANISM: Homo sapiens

<400> SEQUENCE: 150

Arg Tyr Ala Phe Asp Phe Ala Arg Asp Lys Asp Gln Arg Ser Leu Asp
1               5                   10                  15

Ile Asp
```

```
<210> SEQ ID NO 151
<211> LENGTH: 19
<212> TYPE: PRT
<213> ORGANISM: Homo sapiens

<400> SEQUENCE: 151

Ser Val Phe Tyr Gln Tyr Leu Glu Gln Ser Lys Tyr Arg Val Met Asn
1               5                   10                  15

Lys Asp Gln

<210> SEQ ID NO 152
<211> LENGTH: 22
<212> TYPE: PRT
<213> ORGANISM: Homo sapiens

<400> SEQUENCE: 152

Glu Asp Gly Ala Trp Pro Val Leu Leu Asp Glu Phe Val Glu Trp Gln
1               5                   10                  15

Lys Val Arg Gln Thr Ser
            20

<210> SEQ ID NO 153
<211> LENGTH: 19
<212> TYPE: PRT
<213> ORGANISM: Homo sapiens

<400> SEQUENCE: 153

Ser Phe Lys Ser Pro Gln Val Tyr Leu Lys Glu Glu Glu Lys Asn
1               5                   10                  15

Glu Lys Arg

<210> SEQ ID NO 154
<211> LENGTH: 17
<212> TYPE: PRT
<213> ORGANISM: Homo sapiens

<400> SEQUENCE: 154

Arg Lys Lys Gln Gln Glu Ala Gln Gly Glu Lys Ala Ser Arg Tyr Ile
1               5                   10                  15

Glu

<210> SEQ ID NO 155
<211> LENGTH: 20
<212> TYPE: PRT
<213> ORGANISM: Homo sapiens

<400> SEQUENCE: 155

Glu Asp Ile Gly Ile Thr Val Asp Thr Val Leu Ile Leu Glu Glu Lys
1               5                   10                  15

Glu Gln Thr Asn
            20

<210> SEQ ID NO 156
<211> LENGTH: 18
<212> TYPE: PRT
<213> ORGANISM: Homo sapiens

<400> SEQUENCE: 156

Lys Ala Phe Arg Gly Ala Thr Asp Leu Lys Asn Leu Arg Leu Asp Lys
1               5                   10                  15
```

Asn Gln

<210> SEQ ID NO 157
<211> LENGTH: 18
<212> TYPE: PRT
<213> ORGANISM: Homo sapiens

<400> SEQUENCE: 157

Asp Phe Arg Cys Glu Glu Gly Gln Glu Glu Gly Gly Cys Leu Pro Arg
1               5                   10                  15

Pro Gln

<210> SEQ ID NO 158
<211> LENGTH: 21
<212> TYPE: PRT
<213> ORGANISM: Homo sapiens

<400> SEQUENCE: 158

Asp Gly Thr Ser Phe Ala Glu Glu Val Glu Lys Pro Thr Lys Cys Gly
1               5                   10                  15

Cys Ala Leu Cys Ala
            20

<210> SEQ ID NO 159
<211> LENGTH: 20
<212> TYPE: PRT
<213> ORGANISM: Homo sapiens

<400> SEQUENCE: 159

Gln Arg Ile Lys Glu Gln Ala Ser Lys Ile Ser Glu Ala Asp Lys Ser
1               5                   10                  15

Lys Pro Lys Phe
            20

<210> SEQ ID NO 160
<211> LENGTH: 21
<212> TYPE: PRT
<213> ORGANISM: Homo sapiens

<400> SEQUENCE: 160

His Ala Lys Thr Lys Glu Lys Leu Glu Val Thr Trp Glu Lys Met Ser
1               5                   10                  15

Lys Ser Lys His Asn
            20

<210> SEQ ID NO 161
<211> LENGTH: 18
<212> TYPE: PRT
<213> ORGANISM: Homo sapiens

<400> SEQUENCE: 161

Lys Ser Pro Gln Pro Gln Leu Leu Ser Asn Lys Glu Lys Ala Glu Ala
1               5                   10                  15

Arg Lys

<210> SEQ ID NO 162
<211> LENGTH: 16
<212> TYPE: PRT
<213> ORGANISM: Homo sapiens

<400> SEQUENCE: 162

Met Leu Phe Glu Gln Gly Gln Gln Ala Leu Glu Leu Pro Glu Cys Thr

```
1               5                  10                 15
```

<210> SEQ ID NO 163
<211> LENGTH: 20
<212> TYPE: PRT
<213> ORGANISM: Homo sapiens

<400> SEQUENCE: 163

```
Lys Asp Gln Lys Ala Lys Gly Ile Leu His Ser Pro Ala Ser Gln Ser
1               5                  10                 15

Pro Glu Arg Ser
            20
```

<210> SEQ ID NO 164
<211> LENGTH: 16
<212> TYPE: PRT
<213> ORGANISM: Homo sapiens

<400> SEQUENCE: 164

```
His Ser Ser Gln Gly Arg Leu Pro Glu Ala Pro Lys Leu Thr His Leu
1               5                  10                 15
```

<210> SEQ ID NO 165
<211> LENGTH: 18
<212> TYPE: PRT
<213> ORGANISM: Homo sapiens

<400> SEQUENCE: 165

```
Lys Arg Gly Ala Arg Arg Gly Gly Trp Lys Arg Lys Met Pro Ser Thr
1               5                  10                 15

Asp Leu
```

<210> SEQ ID NO 166
<211> LENGTH: 16
<212> TYPE: PRT
<213> ORGANISM: Homo sapiens

<400> SEQUENCE: 166

```
Lys Ile Val Arg Val Pro Leu Thr Lys Met Met Glu Val Asp Val Arg
1               5                  10                 15
```

<210> SEQ ID NO 167
<211> LENGTH: 19
<212> TYPE: PRT
<213> ORGANISM: Homo sapiens

<400> SEQUENCE: 167

```
Gln Phe Leu Lys Asp Ile Arg Glu Ser Val Thr Gln Ile Met Lys Asn
1               5                  10                 15

Pro Lys Ala
```

<210> SEQ ID NO 168
<211> LENGTH: 18
<212> TYPE: PRT
<213> ORGANISM: Homo sapiens

<400> SEQUENCE: 168

```
Ser Lys Gln Gly Val Val Ile Leu Asp Asp Lys Ser Lys Glu Leu Pro
1               5                  10                 15

His Trp
```

<210> SEQ ID NO 169

<211> LENGTH: 20
<212> TYPE: PRT
<213> ORGANISM: Homo sapiens

<400> SEQUENCE: 169

Val Gln Thr Phe Ser Arg Cys Ile Leu Cys Ser Lys Asp Glu Val Asp
1               5                   10                  15

Leu Asp Glu Leu
            20

<210> SEQ ID NO 170
<211> LENGTH: 16
<212> TYPE: PRT
<213> ORGANISM: Homo sapiens

<400> SEQUENCE: 170

Leu Lys Lys Pro Phe Gln Pro Phe Gln Arg Thr Arg Ser Phe Arg Met
1               5                   10                  15

<210> SEQ ID NO 171
<211> LENGTH: 19
<212> TYPE: PRT
<213> ORGANISM: Homo sapiens

<400> SEQUENCE: 171

Met Asn Leu Leu Asp Pro Phe Met Lys Met Thr Asp Glu Gln Glu Lys
1               5                   10                  15

Gly Leu Ser

<210> SEQ ID NO 172
<211> LENGTH: 18
<212> TYPE: PRT
<213> ORGANISM: Homo sapiens

<400> SEQUENCE: 172

Asn Thr Phe Pro Lys Gly Glu Pro Asp Leu Lys Lys Glu Ser Glu Glu
1               5                   10                  15

Asp Lys

<210> SEQ ID NO 173
<211> LENGTH: 19
<212> TYPE: PRT
<213> ORGANISM: Homo sapiens

<400> SEQUENCE: 173

Lys Asn Gly Gln Ala Glu Ala Glu Glu Ala Thr Glu Gly Thr His Ile
1               5                   10                  15

Ser Pro Asn

<210> SEQ ID NO 174
<211> LENGTH: 18
<212> TYPE: PRT
<213> ORGANISM: Homo sapiens

<400> SEQUENCE: 174

Gln Ala Ser Ser Leu Arg Leu Glu Pro Gly Arg Ala Asn Asp Gly Asp
1               5                   10                  15

Trp His

<210> SEQ ID NO 175
<211> LENGTH: 20
<212> TYPE: PRT

<213> ORGANISM: Homo sapiens

<400> SEQUENCE: 175

Glu Leu Lys Gly Phe Ala Glu Arg Leu Gln Arg Asn Glu Ser Gly Leu
1               5                   10                  15

Asp Ser Gly Arg
            20

<210> SEQ ID NO 176
<211> LENGTH: 17
<212> TYPE: PRT
<213> ORGANISM: Homo sapiens

<400> SEQUENCE: 176

Arg Ser Gly Lys Ser Gln Pro Ser Tyr Ile Pro Phe Leu Leu Arg Glu
1               5                   10                  15

Glu

<210> SEQ ID NO 177
<211> LENGTH: 22
<212> TYPE: PRT
<213> ORGANISM: Homo sapiens

<400> SEQUENCE: 177

Arg Arg Ser Asp Tyr Ala Lys Val Ala Lys Ile Phe Tyr Asn Leu Ser
1               5                   10                  15

Ile Gln Ser Phe Asp Asp
            20

<210> SEQ ID NO 178
<211> LENGTH: 19
<212> TYPE: PRT
<213> ORGANISM: Homo sapiens

<400> SEQUENCE: 178

Lys Asn Phe Thr Met Asn Glu Lys Leu Lys Lys Phe Phe Asn Val Leu
1               5                   10                  15

Thr Thr Asn

<210> SEQ ID NO 179
<211> LENGTH: 20
<212> TYPE: PRT
<213> ORGANISM: Homo sapiens

<400> SEQUENCE: 179

Glu Phe Phe Val Asn Glu Ala Arg Lys Asn Asn His His Phe Lys Ser
1               5                   10                  15

Glu Ser Glu Glu
            20

<210> SEQ ID NO 180
<211> LENGTH: 19
<212> TYPE: PRT
<213> ORGANISM: Homo sapiens

<400> SEQUENCE: 180

Lys Asn Thr Gln Ala Ala Glu Ala Leu Val Lys Leu Tyr Glu Thr Lys
1               5                   10                  15

Leu Cys Glu

<210> SEQ ID NO 181

-continued

<210> SEQ ID NO 181
<211> LENGTH: 17
<212> TYPE: PRT
<213> ORGANISM: Homo sapiens

<400> SEQUENCE: 181

Gln Glu Asn Gln Pro Glu Asn Ser Lys Thr Leu Ala Thr Gln Leu Asn
1               5                   10                  15

Gln

<210> SEQ ID NO 182
<211> LENGTH: 19
<212> TYPE: PRT
<213> ORGANISM: Homo sapiens

<400> SEQUENCE: 182

Lys Gln Met Glu Lys Asp Leu Ala Phe Gln Lys Gln Val Ala Glu Lys
1               5                   10                  15

Gln Leu Lys

<210> SEQ ID NO 183
<211> LENGTH: 17
<212> TYPE: PRT
<213> ORGANISM: Homo sapiens

<400> SEQUENCE: 183

Glu Phe Val Glu Gln Leu Arg Lys Glu Gly Val Phe Ala Lys Glu Val
1               5                   10                  15

Arg

<210> SEQ ID NO 184
<211> LENGTH: 18
<212> TYPE: PRT
<213> ORGANISM: Homo sapiens

<400> SEQUENCE: 184

Asp Arg His Pro Gln Ala Leu Glu Ala Ala Gln Ala Glu Leu Gln Gln
1               5                   10                  15

His Asp

<210> SEQ ID NO 185
<211> LENGTH: 20
<212> TYPE: PRT
<213> ORGANISM: Homo sapiens

<400> SEQUENCE: 185

Arg Glu Val Arg Gln Leu Thr Leu Arg Lys Leu Gln Glu Leu Ser Ser
1               5                   10                  15

Lys Ala Asp Glu
            20

<210> SEQ ID NO 186
<211> LENGTH: 20
<212> TYPE: PRT
<213> ORGANISM: Homo sapiens

<400> SEQUENCE: 186

Arg Glu Val Arg Gln Leu Thr Leu Arg Lys Leu Gln Glu Leu Ser Ser
1               5                   10                  15

Lys Ala Asp Glu
            20

<210> SEQ ID NO 187
<211> LENGTH: 19
<212> TYPE: PRT
<213> ORGANISM: Homo sapiens

<400> SEQUENCE: 187

Ala Tyr Ile Arg Glu Gly His Glu Lys Gln Ala Asp Ile Met Ile Phe
1               5                   10                  15

Phe Ala Glu

<210> SEQ ID NO 188
<211> LENGTH: 18
<212> TYPE: PRT
<213> ORGANISM: Homo sapiens

<400> SEQUENCE: 188

Asp Glu Ala Ser Leu Glu Pro Gly Tyr Pro Lys His Ile Lys Glu Leu
1               5                   10                  15

Gly Arg

<210> SEQ ID NO 189
<211> LENGTH: 16
<212> TYPE: PRT
<213> ORGANISM: Homo sapiens

<400> SEQUENCE: 189

Arg Gly Ser Phe Met Gly Ser Asp Glu Val Phe Thr Tyr Phe Tyr Lys
1               5                   10                  15

<210> SEQ ID NO 190
<211> LENGTH: 20
<212> TYPE: PRT
<213> ORGANISM: Homo sapiens

<400> SEQUENCE: 190

Met Ile Pro Gly Gly Leu Ser Glu Ala Lys Pro Ala Thr Pro Glu Ile
1               5                   10                  15

Gln Glu Ile Val
            20

<210> SEQ ID NO 191
<211> LENGTH: 15
<212> TYPE: PRT
<213> ORGANISM: Homo sapiens

<400> SEQUENCE: 191

Asn Glu Thr Tyr Gly Lys Leu Glu Ala Val Gln Tyr Lys Thr Gln
1               5                   10                  15

<210> SEQ ID NO 192
<211> LENGTH: 20
<212> TYPE: PRT
<213> ORGANISM: Homo sapiens

<400> SEQUENCE: 192

Asp Leu Val Leu Thr Gly Tyr Gln Val Asp Lys Asn Lys Asp Asp Glu
1               5                   10                  15

Leu Thr Gly Phe
            20

<210> SEQ ID NO 193
<211> LENGTH: 20
<212> TYPE: PRT

<213> ORGANISM: Homo sapiens

<400> SEQUENCE: 193

Arg Gln Glu His Cys Met Ser Glu His Phe Lys Asn Arg Pro Ala Cys
1               5                   10                  15

Leu Gly Ala Arg
            20

<210> SEQ ID NO 194
<211> LENGTH: 19
<212> TYPE: PRT
<213> ORGANISM: Homo sapiens

<400> SEQUENCE: 194

Gln Gly His Lys Trp Gly Glu Ser Pro Ser Gln Gly Thr Gln Ala Gly
1               5                   10                  15

Ala Gly Lys

<210> SEQ ID NO 195
<211> LENGTH: 21
<212> TYPE: PRT
<213> ORGANISM: Homo sapiens

<400> SEQUENCE: 195

Arg Ala Cys Gly Lys Arg Val Ser Glu Gly Asp Arg Asn Gly Ser Gly
1               5                   10                  15

Gly Gly Lys Trp Gly
            20

<210> SEQ ID NO 196
<211> LENGTH: 16
<212> TYPE: PRT
<213> ORGANISM: Homo sapiens

<400> SEQUENCE: 196

Met Val Glu Ala Phe Cys Ala Thr Trp Lys Leu Thr Asn Ser Gln Asn
1               5                   10                  15

<210> SEQ ID NO 197
<211> LENGTH: 15
<212> TYPE: PRT
<213> ORGANISM: Homo sapiens

<400> SEQUENCE: 197

Gln Val Gly Asn Val Thr Lys Pro Thr Val Ile Ile Ser Gln Glu
1               5                   10                  15

<210> SEQ ID NO 198
<211> LENGTH: 14
<212> TYPE: PRT
<213> ORGANISM: Homo sapiens

<400> SEQUENCE: 198

Lys Val Val Ile Arg Thr Leu Ser Thr Phe Lys Asn Thr Glu
1               5                   10

<210> SEQ ID NO 199
<211> LENGTH: 19
<212> TYPE: PRT
<213> ORGANISM: Homo sapiens

<400> SEQUENCE: 199

Arg Ala Val Phe Arg Glu Ala Glu Val Thr Leu Glu Ala Gly Gly Ala

```
1               5                   10                  15

Glu Gln Glu

<210> SEQ ID NO 200
<211> LENGTH: 17
<212> TYPE: PRT
<213> ORGANISM: Homo sapiens

<400> SEQUENCE: 200

Gln Glu Pro Ala Leu Phe Ser Thr Asp Asn Asp Phe Thr Val Arg
1               5                   10                  15

Asn

<210> SEQ ID NO 201
<211> LENGTH: 15
<212> TYPE: PRT
<213> ORGANISM: Homo sapiens

<400> SEQUENCE: 201

Gln Lys Tyr Glu Ala His Val Pro Glu Asn Ala Val Gly His Glu
1               5                   10                  15

<210> SEQ ID NO 202
<211> LENGTH: 14
<212> TYPE: PRT
<213> ORGANISM: Homo sapiens

<400> SEQUENCE: 202

Lys Lys Ile Ile Glu Lys Met Leu Asn Ser Asp Lys Ser Asn
1               5                   10

<210> SEQ ID NO 203
<211> LENGTH: 20
<212> TYPE: PRT
<213> ORGANISM: Homo sapiens

<400> SEQUENCE: 203

Gly Lys Pro Gly Asn Gln Asn Ser Lys Asn Glu Pro Pro Lys Lys Arg
1               5                   10                  15

Glu Arg Glu Arg
            20

<210> SEQ ID NO 204
<211> LENGTH: 14
<212> TYPE: PRT
<213> ORGANISM: Homo sapiens

<400> SEQUENCE: 204

Gln Ala Glu Ala Pro Leu Val Pro Leu Ser Arg Gln Asn Lys
1               5                   10

<210> SEQ ID NO 205
<211> LENGTH: 13
<212> TYPE: PRT
<213> ORGANISM: Homo sapiens

<400> SEQUENCE: 205

Asn Cys Phe Leu Thr Glu Arg Lys Ala Gln Pro Asp Glu
1               5                   10

<210> SEQ ID NO 206
<211> LENGTH: 15
<212> TYPE: PRT
```

<213> ORGANISM: Homo sapiens

<400> SEQUENCE: 206

Glu Phe Asp Thr Val Asp Leu Ser Ala Val Asp Val His Pro Asn
1               5                   10                  15

<210> SEQ ID NO 207
<211> LENGTH: 18
<212> TYPE: PRT
<213> ORGANISM: Homo sapiens

<400> SEQUENCE: 207

Asn Lys Glu Val Tyr His Glu Lys Asp Ile Lys Val Phe Phe Asp Lys
1               5                   10                  15

Ala Lys

<210> SEQ ID NO 208
<211> LENGTH: 15
<212> TYPE: PRT
<213> ORGANISM: Homo sapiens

<400> SEQUENCE: 208

Lys Gln Val Asp Leu Glu Asn Val Trp Leu Asp Phe Ile Arg Glu
1               5                   10                  15

<210> SEQ ID NO 209
<211> LENGTH: 18
<212> TYPE: PRT
<213> ORGANISM: Homo sapiens

<400> SEQUENCE: 209

Leu Lys Lys Pro Gln Asp Ser Gln Leu Glu Glu Gly Lys Pro Gly Tyr
1               5                   10                  15

Leu Asp

<210> SEQ ID NO 210
<211> LENGTH: 17
<212> TYPE: PRT
<213> ORGANISM: Homo sapiens

<400> SEQUENCE: 210

Lys Ala Lys Arg Leu Gln Lys Gln Pro Glu Gly Glu Glu Pro Glu Met
1               5                   10                  15

Glu

<210> SEQ ID NO 211
<211> LENGTH: 22
<212> TYPE: PRT
<213> ORGANISM: Homo sapiens

<400> SEQUENCE: 211

Lys Asp Arg Pro Ser Phe Ser Glu Ile Ala Ser Ala Leu Gly Asp Ser
1               5                   10                  15

Thr Val Asp Ser Lys Pro
            20

<210> SEQ ID NO 212
<211> LENGTH: 17
<212> TYPE: PRT
<213> ORGANISM: Homo sapiens

<400> SEQUENCE: 212

Lys Arg Gly Ile Glu Glu Arg Ile Gln Glu Glu Ser Gly Phe Leu Ile
1               5                   10                  15

Glu

<210> SEQ ID NO 213
<211> LENGTH: 17
<212> TYPE: PRT
<213> ORGANISM: Homo sapiens

<400> SEQUENCE: 213

Asp Arg Val Ile Gly Lys Asn Arg Gln Pro Lys Phe Glu Asp Arg Thr
1               5                   10                  15

Lys

<210> SEQ ID NO 214
<211> LENGTH: 16
<212> TYPE: PRT
<213> ORGANISM: Homo sapiens

<400> SEQUENCE: 214

Asn Pro Gln His Phe Leu Asp Asp Lys Gly Gln Phe Lys Lys Ser Asp
1               5                   10                  15

<210> SEQ ID NO 215
<211> LENGTH: 18
<212> TYPE: PRT
<213> ORGANISM: Homo sapiens

<400> SEQUENCE: 215

Arg His Cys Ile Leu Gly Glu Trp Leu Pro Ile Leu Ile Met Ala Val
1               5                   10                  15

Phe Asn

<210> SEQ ID NO 216
<211> LENGTH: 16
<212> TYPE: PRT
<213> ORGANISM: Homo sapiens

<400> SEQUENCE: 216

Lys Gln Arg Glu Leu Ala Gly Asn Thr Met Thr Val Ser Tyr Met Ser
1               5                   10                  15

<210> SEQ ID NO 217
<211> LENGTH: 21
<212> TYPE: PRT
<213> ORGANISM: Homo sapiens

<400> SEQUENCE: 217

Arg Asn Ala His Gly Ser Cys Leu His Ala Ser Thr Ala Asn Gly Ser
1               5                   10                  15

Ile Leu Ala Gly Leu
            20

<210> SEQ ID NO 218
<211> LENGTH: 16
<212> TYPE: PRT
<213> ORGANISM: Homo sapiens

<400> SEQUENCE: 218

Glu Leu Met Glu Lys Glu Val Glu Pro Glu Gly Ser Lys Arg Thr Asp
1               5                   10                  15

<210> SEQ ID NO 219
<211> LENGTH: 15
<212> TYPE: PRT
<213> ORGANISM: Homo sapiens

<400> SEQUENCE: 219

Lys Ala Arg Ser Phe Cys Lys Thr His Ala Arg Leu Phe Lys Lys
1               5                   10                  15

<210> SEQ ID NO 220
<211> LENGTH: 16
<212> TYPE: PRT
<213> ORGANISM: Homo sapiens

<400> SEQUENCE: 220

Lys Asn Lys Arg Leu Ser Gly Met Glu Glu Trp Ile Glu Gly Glu Lys
1               5                   10                  15

<210> SEQ ID NO 221
<211> LENGTH: 17
<212> TYPE: PRT
<213> ORGANISM: Homo sapiens

<400> SEQUENCE: 221

Glu Gly Ser Thr Asp Leu Pro Leu Ala Pro Glu Ser Arg Val Asp Pro
1               5                   10                  15

Glu

<210> SEQ ID NO 222
<211> LENGTH: 15
<212> TYPE: PRT
<213> ORGANISM: Homo sapiens

<400> SEQUENCE: 222

Lys Val Ala Gln Gln Arg His Leu Glu Lys Gln His Leu Arg
1               5                   10                  15

<210> SEQ ID NO 223
<211> LENGTH: 20
<212> TYPE: PRT
<213> ORGANISM: Homo sapiens

<400> SEQUENCE: 223

Asp His Lys His Leu Asp His Glu Val Ala Lys Pro Ala Arg Arg Lys
1               5                   10                  15

Arg Leu Pro Glu
            20

<210> SEQ ID NO 224
<211> LENGTH: 17
<212> TYPE: PRT
<213> ORGANISM: Homo sapiens

<400> SEQUENCE: 224

Lys Leu Thr Ile Glu Ser Thr Pro Phe Asn Val Ala Glu Gly Lys Glu
1               5                   10                  15

Cys

<210> SEQ ID NO 225
<211> LENGTH: 21
<212> TYPE: PRT
<213> ORGANISM: Homo sapiens

<400> SEQUENCE: 225

-continued

Lys Ser Asp Leu Val Asn Glu Glu Ala Thr Gly Gln Phe Arg Val Tyr
1               5                   10                  15

Pro Glu Leu Pro Lys
            20

<210> SEQ ID NO 226
<211> LENGTH: 18
<212> TYPE: PRT
<213> ORGANISM: Homo sapiens

<400> SEQUENCE: 226

Lys Pro Val Glu Asp Lys Asp Ala Val Ala Phe Thr Cys Glu Pro Glu
1               5                   10                  15

Ala Gln

<210> SEQ ID NO 227
<211> LENGTH: 22
<212> TYPE: PRT
<213> ORGANISM: Homo sapiens

<400> SEQUENCE: 227

Asp Glu Lys Leu Ile Ser Leu Ile Cys Arg Ala Val Lys Ala Thr Phe
1               5                   10                  15

Asn Pro Ala Gln Asp Lys
            20

<210> SEQ ID NO 228
<211> LENGTH: 19
<212> TYPE: PRT
<213> ORGANISM: Homo sapiens

<400> SEQUENCE: 228

Lys Asp Lys Trp Asp Glu Leu Lys Glu Ala Gly Val Ser Asp Met Lys
1               5                   10                  15

Leu Gly Asp

<210> SEQ ID NO 229
<211> LENGTH: 23
<212> TYPE: PRT
<213> ORGANISM: Homo sapiens

<400> SEQUENCE: 229

Asp Ser Trp Ile Val Pro Leu Asp Asn Leu Thr Lys Asp Asp Leu Asp
1               5                   10                  15

Glu Glu Glu Asp Thr His Leu
            20

<210> SEQ ID NO 230
<211> LENGTH: 21
<212> TYPE: PRT
<213> ORGANISM: Homo sapiens

<400> SEQUENCE: 230

Glu Ala Val Val Thr Asn Glu Leu Glu Asp Gly Asp Arg Gln Lys Ala
1               5                   10                  15

Met Lys Arg Leu Arg
            20

<210> SEQ ID NO 231
<211> LENGTH: 18
<212> TYPE: PRT

<213> ORGANISM: Homo sapiens

<400> SEQUENCE: 231

Arg Arg Tyr Arg Asp Thr Lys Arg Ala Phe Pro His Leu Val Asn Ala
1               5                   10                  15

Gly Lys

<210> SEQ ID NO 232
<211> LENGTH: 18
<212> TYPE: PRT
<213> ORGANISM: Homo sapiens

<400> SEQUENCE: 232

Lys Ala Arg Asp Thr Lys Val Leu Ile Glu Asp Thr Asp Asp Glu Ala
1               5                   10                  15

Asn Thr

<210> SEQ ID NO 233
<211> LENGTH: 20
<212> TYPE: PRT
<213> ORGANISM: Homo sapiens

<400> SEQUENCE: 233

Arg Lys Arg Val Leu Glu Ala Lys Glu Leu Ala Leu Gln Pro Lys Asp
1               5                   10                  15

Asp Ile Val Asp
            20

<210> SEQ ID NO 234
<211> LENGTH: 21
<212> TYPE: PRT
<213> ORGANISM: Homo sapiens

<400> SEQUENCE: 234

Arg His Gly Val Ser His Lys Val Asp Asp Ser Ser Gly Ser Ile Gly
1               5                   10                  15

Arg Arg Tyr Ala Arg
            20

<210> SEQ ID NO 235
<211> LENGTH: 20
<212> TYPE: PRT
<213> ORGANISM: Homo sapiens

<400> SEQUENCE: 235

Glu Ala Arg Tyr Pro Leu Phe Glu Gly Gln Glu Thr Gly Lys Lys Glu
1               5                   10                  15

Thr Ile Glu Glu
            20

<210> SEQ ID NO 236
<211> LENGTH: 20
<212> TYPE: PRT
<213> ORGANISM: Homo sapiens

<400> SEQUENCE: 236

Asp Leu Ala Gly His Asp Met Gly His Glu Ser Lys Arg Met His Ile
1               5                   10                  15

Glu Lys Asp Glu
            20

-continued

<210> SEQ ID NO 237
<211> LENGTH: 20
<212> TYPE: PRT
<213> ORGANISM: Homo sapiens

<400> SEQUENCE: 237

Glu Lys Gln Val Gln Leu Glu Lys Thr Glu Leu Lys Met Asp Phe Leu
1               5                   10                  15

Arg Glu Arg Glu
            20

<210> SEQ ID NO 238
<211> LENGTH: 19
<212> TYPE: PRT
<213> ORGANISM: Homo sapiens

<400> SEQUENCE: 238

Glu Ala Asp Arg Ser Gly Gly Arg Thr Asp Ala Glu Arg Thr Ile Gln
1               5                   10                  15

Asp Gly Arg

<210> SEQ ID NO 239
<211> LENGTH: 18
<212> TYPE: PRT
<213> ORGANISM: Homo sapiens

<400> SEQUENCE: 239

Glu Ala Leu Tyr Pro Gln Arg Arg Ser Tyr Thr Ser Glu Asp Glu Ala
1               5                   10                  15

Trp Lys

<210> SEQ ID NO 240
<211> LENGTH: 19
<212> TYPE: PRT
<213> ORGANISM: Homo sapiens

<400> SEQUENCE: 240

Asp Tyr Tyr Lys Val Pro Arg Glu Arg Arg Ser Ser Thr Ala Lys Pro
1               5                   10                  15

Glu Val Glu

<210> SEQ ID NO 241
<211> LENGTH: 19
<212> TYPE: PRT
<213> ORGANISM: Homo sapiens

<400> SEQUENCE: 241

Asp Lys Tyr Asp Val Pro His Asp Lys Ile Gly Lys Ile Phe Lys Lys
1               5                   10                  15

Cys Lys Lys

<210> SEQ ID NO 242
<211> LENGTH: 21
<212> TYPE: PRT
<213> ORGANISM: Homo sapiens

<400> SEQUENCE: 242

Asp Pro Asp Gln Tyr Asn Phe Ser Ser Ser Glu Leu Gly Gly Asp Phe
1               5                   10                  15

Glu Phe Met Asp Asp
            20

-continued

<210> SEQ ID NO 243
<211> LENGTH: 15
<212> TYPE: PRT
<213> ORGANISM: Homo sapiens

<400> SEQUENCE: 243

Glu Tyr Ile Arg Gln Leu Pro Pro Asn Phe Pro Tyr Arg Asp Asp
1               5                   10                  15

<210> SEQ ID NO 244
<211> LENGTH: 20
<212> TYPE: PRT
<213> ORGANISM: Homo sapiens

<400> SEQUENCE: 244

Asp Thr Thr Val Leu Leu Pro Pro Tyr Asp Asp Ala Thr Val Asn Gly
1               5                   10                  15

Ala Ala Lys Glu
            20

<210> SEQ ID NO 245
<211> LENGTH: 14
<212> TYPE: PRT
<213> ORGANISM: Homo sapiens

<400> SEQUENCE: 245

Arg Arg Glu Glu Val Thr Lys Lys His Gln Tyr Glu Ile Arg
1               5                   10

<210> SEQ ID NO 246
<211> LENGTH: 19
<212> TYPE: PRT
<213> ORGANISM: Homo sapiens

<400> SEQUENCE: 246

Lys Glu Ser Arg Tyr Val His Asp Lys His Phe Glu Val Leu His Ser
1               5                   10                  15

Asp Leu Glu

<210> SEQ ID NO 247
<211> LENGTH: 15
<212> TYPE: PRT
<213> ORGANISM: Homo sapiens

<400> SEQUENCE: 247

Asp Phe Phe Asp Arg Phe Met Leu Thr Gln Lys Asp Ile Asn Lys
1               5                   10                  15

<210> SEQ ID NO 248
<211> LENGTH: 19
<212> TYPE: PRT
<213> ORGANISM: Homo sapiens

<400> SEQUENCE: 248

Glu Ser Lys His Phe Thr Arg Asp Leu Met Glu Lys Leu Lys Gly Arg
1               5                   10                  15

Thr Ser Arg

<210> SEQ ID NO 249
<211> LENGTH: 17
<212> TYPE: PRT
<213> ORGANISM: Homo sapiens -continued

```
<400> SEQUENCE: 249

Glu Thr Asp Arg Leu Pro Arg Cys Val Arg Ser Thr Ala Arg Leu Ala
1               5                   10                  15
Arg

<210> SEQ ID NO 250
<211> LENGTH: 20
<212> TYPE: PRT
<213> ORGANISM: Homo sapiens

<400> SEQUENCE: 250

Glu Ser Arg Trp Lys Asp Ile Arg Ala Arg Ile Phe Leu Ile Ala Ser
1               5                   10                  15
Lys Glu Leu Glu
            20

<210> SEQ ID NO 251
<211> LENGTH: 23
<212> TYPE: PRT
<213> ORGANISM: Homo sapiens

<400> SEQUENCE: 251

Lys Val Thr Leu Gly Leu Leu Val Phe Leu Ala Gly Phe Pro Val Leu
1               5                   10                  15
Asp Ala Asn Asp Leu Glu Asp
            20

<210> SEQ ID NO 252
<211> LENGTH: 12
<212> TYPE: PRT
<213> ORGANISM: Homo sapiens

<400> SEQUENCE: 252

Ser Glu Trp Arg Ser Ser Gly Glu Gln Ala Gly Arg
1               5                   10

<210> SEQ ID NO 253
<211> LENGTH: 16
<212> TYPE: PRT
<213> ORGANISM: Homo sapiens

<400> SEQUENCE: 253

Lys Cys Lys Cys Lys Phe Gly Gln Lys Ser Gly His His Pro Gly Glu
1               5                   10                  15

<210> SEQ ID NO 254
<211> LENGTH: 21
<212> TYPE: PRT
<213> ORGANISM: Homo sapiens

<400> SEQUENCE: 254

Lys Val Ala Lys Glu Ser Asp Ser Val Phe Val Leu Lys Ile Tyr His
1               5                   10                  15
Leu Arg Gln Glu Asp
            20

<210> SEQ ID NO 255
<211> LENGTH: 19
<212> TYPE: PRT
<213> ORGANISM: Homo sapiens

<400> SEQUENCE: 255
```

Glu Arg Glu Lys Thr Val Thr Gly Glu Phe Ile Asp Lys Glu Ser Lys
1               5                   10                  15

Arg Pro Lys

<210> SEQ ID NO 256
<211> LENGTH: 18
<212> TYPE: PRT
<213> ORGANISM: Homo sapiens

<400> SEQUENCE: 256

Lys Arg Ala Glu Asp Thr Ala Gly Gln Thr Ala Leu Thr Val Met Arg
1               5                   10                  15

Pro Asp

<210> SEQ ID NO 257
<211> LENGTH: 19
<212> TYPE: PRT
<213> ORGANISM: Homo sapiens

<400> SEQUENCE: 257

Lys Val Ala Arg Lys Val Arg Ala Leu Tyr Asp Phe Glu Ala Val Glu
1               5                   10                  15

Asp Asn Glu

<210> SEQ ID NO 258
<211> LENGTH: 18
<212> TYPE: PRT
<213> ORGANISM: Homo sapiens

<400> SEQUENCE: 258

Glu Thr Glu Val Ala Ala Val Asp Lys Leu Asn Val Ile Asp Asp
1               5                   10                  15

Val Glu

<210> SEQ ID NO 259
<211> LENGTH: 19
<212> TYPE: PRT
<213> ORGANISM: Homo sapiens

<400> SEQUENCE: 259

Glu Ile Lys Lys Ser Glu Pro Glu Pro Val Tyr Ile Asp Glu Asp Lys
1               5                   10                  15

Met Asp Arg

<210> SEQ ID NO 260
<211> LENGTH: 18
<212> TYPE: PRT
<213> ORGANISM: Homo sapiens

<400> SEQUENCE: 260

Asp Glu Glu Cys Gly Thr Asp Glu Tyr Cys Ala Ser Pro Thr Arg Gly
1               5                   10                  15

Gly Asp

<210> SEQ ID NO 261
<211> LENGTH: 20
<212> TYPE: PRT
<213> ORGANISM: Homo sapiens

<400> SEQUENCE: 261

Arg Gly Glu Ile Glu Glu Thr Ile Thr Glu Ser Phe Gly Asn Asp His

```
1               5                   10                  15
```

Ser Thr Leu Asp
            20

<210> SEQ ID NO 262
<211> LENGTH: 22
<212> TYPE: PRT
<213> ORGANISM: Homo sapiens

<400> SEQUENCE: 262

Met Asp Leu Arg Arg Arg Asp Tyr His Met Glu Arg Pro Leu Leu Asn
1               5                   10                  15

Gln Glu His Leu Glu Glu
            20

<210> SEQ ID NO 263
<211> LENGTH: 16
<212> TYPE: PRT
<213> ORGANISM: Homo sapiens

<400> SEQUENCE: 263

Asp Thr Asp Ile Tyr Arg Asp Val Ala Glu Tyr Ser Glu Ala Lys Glu
1               5                   10                  15

<210> SEQ ID NO 264
<211> LENGTH: 24
<212> TYPE: PRT
<213> ORGANISM: Homo sapiens

<400> SEQUENCE: 264

Glu Phe Tyr Ser Asp Ala Leu Lys Gln Arg Cys Gly Val Asp Val Asp
1               5                   10                  15

Phe Leu Ile Ser Gln Lys Lys Lys
            20

<210> SEQ ID NO 265
<211> LENGTH: 20
<212> TYPE: PRT
<213> ORGANISM: Homo sapiens

<400> SEQUENCE: 265

Asp Ala His Gln Ala Arg Val Leu Ile Gly Phe Glu Glu Asp Ile Leu
1               5                   10                  15

Ile Val Ser Glu
            20

<210> SEQ ID NO 266
<211> LENGTH: 18
<212> TYPE: PRT
<213> ORGANISM: Homo sapiens

<400> SEQUENCE: 266

Glu Arg Arg Ile Cys Glu Cys Pro Asp Gly Phe His Gly Pro His Cys
1               5                   10                  15

Glu Lys

<210> SEQ ID NO 267
<211> LENGTH: 19
<212> TYPE: PRT
<213> ORGANISM: Homo sapiens

<400> SEQUENCE: 267

-continued

Lys Arg Tyr Glu Ala Ser Leu Ile His Ala Leu Arg Pro Ala Gly Ala
1               5                   10                  15

Gln Leu Arg

<210> SEQ ID NO 268
<211> LENGTH: 19
<212> TYPE: PRT
<213> ORGANISM: Homo sapiens

<400> SEQUENCE: 268

Lys Arg Lys Val Asp Gly Leu Ser Thr Glu Ala Glu Gln Pro Phe Ile
1               5                   10                  15

Pro Val Glu

<210> SEQ ID NO 269
<211> LENGTH: 20
<212> TYPE: PRT
<213> ORGANISM: Homo sapiens

<400> SEQUENCE: 269

Lys Glu Gly Ala Cys Asp Glu Leu Phe Ser Tyr Leu Ile Glu Lys Val
1               5                   10                  15

Lys Arg Lys Lys
            20

<210> SEQ ID NO 270
<211> LENGTH: 18
<212> TYPE: PRT
<213> ORGANISM: Homo sapiens

<400> SEQUENCE: 270

Asp Ile Lys Met Ile Leu Lys Met Val Gln Leu Asp Ser Ile Glu Asp
1               5                   10                  15

Leu Glu

<210> SEQ ID NO 271
<211> LENGTH: 15
<212> TYPE: PRT
<213> ORGANISM: Homo sapiens

<400> SEQUENCE: 271

Arg Leu Arg Lys Lys Ala Phe Ala Asn Pro Glu Asp Ala Leu Arg
1               5                   10                  15

<210> SEQ ID NO 272
<211> LENGTH: 16
<212> TYPE: PRT
<213> ORGANISM: Homo sapiens

<400> SEQUENCE: 272

Arg Ser Asp Pro Asp Val Glu Arg Cys Leu Arg Ala His Arg Asn Asp
1               5                   10                  15

<210> SEQ ID NO 273
<211> LENGTH: 17
<212> TYPE: PRT
<213> ORGANISM: Homo sapiens

<400> SEQUENCE: 273

Arg Val Ala His Thr Val Ala Tyr Leu Gly Lys Leu Arg Ala Pro Ile
1               5                   10                  15

Arg

```
<210> SEQ ID NO 274
<211> LENGTH: 13
<212> TYPE: PRT
<213> ORGANISM: Homo sapiens

<400> SEQUENCE: 274

Lys Arg Arg Ala Leu Ala Ala Pro Ala Ala Glu Glu Lys
1               5                   10

<210> SEQ ID NO 275
<211> LENGTH: 20
<212> TYPE: PRT
<213> ORGANISM: Homo sapiens

<400> SEQUENCE: 275

Glu Ala Arg Glu Lys Met Leu Ala Ala Lys Ser Ala Asp Gly Ser Ala
1               5                   10                  15

Pro Ala Gly Glu
            20

<210> SEQ ID NO 276
<211> LENGTH: 16
<212> TYPE: PRT
<213> ORGANISM: Homo sapiens

<400> SEQUENCE: 276

Met Ile Trp Leu Arg His Arg Lys Pro Glu Leu Glu Arg Pro Ile Lys
1               5                   10                  15

<210> SEQ ID NO 277
<211> LENGTH: 13
<212> TYPE: PRT
<213> ORGANISM: Homo sapiens

<400> SEQUENCE: 277

Lys Arg Arg Ala Leu Ala Ala Pro Ala Ala Glu Glu Lys
1               5                   10

<210> SEQ ID NO 278
<211> LENGTH: 14
<212> TYPE: PRT
<213> ORGANISM: Homo sapiens

<400> SEQUENCE: 278

Lys Pro Asn Lys Ala Leu Lys Val Lys Lys Glu Ala Gly Glu
1               5                   10

<210> SEQ ID NO 279
<211> LENGTH: 22
<212> TYPE: PRT
<213> ORGANISM: Homo sapiens

<400> SEQUENCE: 279

Lys Arg Val Thr Gln Lys Glu Glu Leu Glu Arg Gln Arg Val Glu Leu
1               5                   10                  15

Gln Gln Glu Val Glu Lys
            20

<210> SEQ ID NO 280
<211> LENGTH: 12
<212> TYPE: PRT
<213> ORGANISM: Homo sapiens
```

```
<400> SEQUENCE: 280

Arg Leu Glu Leu Asp Ala Leu Arg Ser Lys Tyr Glu
1               5                   10

<210> SEQ ID NO 281
<211> LENGTH: 21
<212> TYPE: PRT
<213> ORGANISM: Homo sapiens

<400> SEQUENCE: 281

Lys Met His Thr Asp Gly Arg Ser Cys Leu Glu Arg Glu Asp Thr Val
1               5                   10                  15

Leu Glu Val Thr Glu
            20

<210> SEQ ID NO 282
<211> LENGTH: 18
<212> TYPE: PRT
<213> ORGANISM: Homo sapiens

<400> SEQUENCE: 282

Lys Lys Gly Phe Lys Leu Leu Thr Asp Glu Lys Ser Cys Gln Asp Val
1               5                   10                  15

Asp Glu

<210> SEQ ID NO 283
<211> LENGTH: 21
<212> TYPE: PRT
<213> ORGANISM: Homo sapiens

<400> SEQUENCE: 283

Lys Arg Thr Glu Lys Arg Leu Arg Lys Ala Ile Arg Thr Leu Arg Lys
1               5                   10                  15

Ala Val His Arg Glu
            20

<210> SEQ ID NO 284
<211> LENGTH: 17
<212> TYPE: PRT
<213> ORGANISM: Homo sapiens

<400> SEQUENCE: 284

Arg Val Glu Gly Pro Gln Thr Glu Ser Lys Asn Glu Ala Ser Ser Arg
1               5                   10                  15

Asp

<210> SEQ ID NO 285
<211> LENGTH: 19
<212> TYPE: PRT
<213> ORGANISM: Homo sapiens

<400> SEQUENCE: 285

Glu Glu Thr Lys Ser Thr Glu Thr Gly Ser Arg Val Gly Lys
1               5                   10                  15

Leu Pro Glu

<210> SEQ ID NO 286
<211> LENGTH: 21
<212> TYPE: PRT
<213> ORGANISM: Homo sapiens

<400> SEQUENCE: 286
```

```
Lys Trp Glu Asn Phe Lys Leu Glu Ile Asn Glu Lys Asn Ser Trp Lys
1               5                   10                  15

Leu Phe Gln Phe Asp
            20

<210> SEQ ID NO 287
<211> LENGTH: 17
<212> TYPE: PRT
<213> ORGANISM: Homo sapiens

<400> SEQUENCE: 287

Asp Lys Gly Tyr Leu Thr Lys Glu Asp Leu Arg Val Leu Met Glu Lys
1               5                   10                  15

Glu

<210> SEQ ID NO 288
<211> LENGTH: 20
<212> TYPE: PRT
<213> ORGANISM: Homo sapiens

<400> SEQUENCE: 288

Lys Asp Pro Leu Ala Val Asp Lys Ile Met Lys Asp Leu Asp Gln Cys
1               5                   10                  15

Arg Asp Gly Lys
            20

<210> SEQ ID NO 289
<211> LENGTH: 21
<212> TYPE: PRT
<213> ORGANISM: Homo sapiens

<400> SEQUENCE: 289

Met Ser Arg Arg Thr Arg Cys Glu Asp Leu Asp Glu Leu His Tyr Gln
1               5                   10                  15

Asp Thr Asp Ser Asp
            20

<210> SEQ ID NO 290
<211> LENGTH: 23
<212> TYPE: PRT
<213> ORGANISM: Homo sapiens

<400> SEQUENCE: 290

Glu Glu Asp Leu Lys Glu Val Leu Arg Ser Glu Ala Gly Ile Glu Leu
1               5                   10                  15

Ile Ile Glu Asp Asp Ile Arg
            20

<210> SEQ ID NO 291
<211> LENGTH: 20
<212> TYPE: PRT
<213> ORGANISM: Homo sapiens

<400> SEQUENCE: 291

Arg Arg Ser Pro Ile Lys Lys Val Arg Lys Ser Leu Ala Leu Asp Ile
1               5                   10                  15

Val Asp Glu Asp
            20

<210> SEQ ID NO 292
<211> LENGTH: 17
```

```
<212> TYPE: PRT
<213> ORGANISM: Homo sapiens

<400> SEQUENCE: 292

Glu Asp Tyr Lys Asn Thr Ala Glu Trp Leu Leu Ser His Thr Lys His
1               5                   10                  15
Arg

<210> SEQ ID NO 293
<211> LENGTH: 22
<212> TYPE: PRT
<213> ORGANISM: Homo sapiens

<400> SEQUENCE: 293

Asp Glu Arg Phe Gly Asp Arg Phe Pro Ala Met Ser Asp Ala Tyr Asp
1               5                   10                  15
Arg Thr Met Arg Gln Arg
            20

<210> SEQ ID NO 294
<211> LENGTH: 16
<212> TYPE: PRT
<213> ORGANISM: Homo sapiens

<400> SEQUENCE: 294

Lys Val Ile Met Asp Tyr Glu Ser Leu Glu Lys Ala Asn His Glu Glu
1               5                   10                  15

<210> SEQ ID NO 295
<211> LENGTH: 22
<212> TYPE: PRT
<213> ORGANISM: Homo sapiens

<400> SEQUENCE: 295

Asp Gln Asp Arg Lys Ser Arg Leu Met Gly Leu Glu Ala Leu Lys Ser
1               5                   10                  15
His Ile Met Ala Ala Lys
            20

<210> SEQ ID NO 296
<211> LENGTH: 20
<212> TYPE: PRT
<213> ORGANISM: Homo sapiens

<400> SEQUENCE: 296

Lys Gly Val Ile Val Asp Lys Asp Phe Ser His Pro Gln Met Pro Lys
1               5                   10                  15
Lys Val Glu Asp
            20

<210> SEQ ID NO 297
<211> LENGTH: 17
<212> TYPE: PRT
<213> ORGANISM: Homo sapiens

<400> SEQUENCE: 297

Arg Met Ile Leu Lys Ile Asp Asp Ile Arg Lys Pro Gly Glu Ser Glu
1               5                   10                  15
Glu

<210> SEQ ID NO 298
<211> LENGTH: 20
```

```
<212> TYPE: PRT
<213> ORGANISM: Homo sapiens

<400> SEQUENCE: 298

Arg Leu Gln Pro Glu Phe Lys Pro Lys Gln Leu Glu Gly Thr Met Ala
1               5                   10                  15

Asn Cys Glu Arg
            20

<210> SEQ ID NO 299
<211> LENGTH: 20
<212> TYPE: PRT
<213> ORGANISM: Homo sapiens

<400> SEQUENCE: 299

Lys Phe Met Gln Ala Ser Glu Asp Leu Leu Lys Glu His Tyr Val Asp
1               5                   10                  15

Leu Lys Asp Arg
            20

<210> SEQ ID NO 300
<211> LENGTH: 21
<212> TYPE: PRT
<213> ORGANISM: Homo sapiens

<400> SEQUENCE: 300

Asp Ser Val Glu Ser Ala Glu Lys Glu Ile Gly Leu Trp Phe His Pro
1               5                   10                  15

Glu Glu Leu Val Asp
            20

<210> SEQ ID NO 301
<211> LENGTH: 18
<212> TYPE: PRT
<213> ORGANISM: Homo sapiens

<400> SEQUENCE: 301

Lys Ser Pro Pro Glu Ser Glu Asn Lys Glu Gln Leu Glu Ala Arg Arg
1               5                   10                  15

Arg Arg

<210> SEQ ID NO 302
<211> LENGTH: 18
<212> TYPE: PRT
<213> ORGANISM: Homo sapiens

<400> SEQUENCE: 302

Arg Asp Gly Arg Lys Val Thr Val Ile Glu Arg Asp Leu Lys Glu Pro
1               5                   10                  15

Asp Arg

<210> SEQ ID NO 303
<211> LENGTH: 17
<212> TYPE: PRT
<213> ORGANISM: Homo sapiens

<400> SEQUENCE: 303

Asp His Leu Lys Glu Pro Phe Leu Glu Ala Thr Asp Asn Ser His Leu
1               5                   10                  15

Arg
```

<210> SEQ ID NO 304
<211> LENGTH: 19
<212> TYPE: PRT
<213> ORGANISM: Homo sapiens

<400> SEQUENCE: 304

Asp Leu Glu Val Lys Asp Trp Met Gln Lys Arg Arg Gly Leu Arg
1               5                   10                  15

Asn Ser Arg

<210> SEQ ID NO 305
<211> LENGTH: 24
<212> TYPE: PRT
<213> ORGANISM: Homo sapiens

<400> SEQUENCE: 305

Glu Tyr His Lys Val His Gln Met Met Arg Glu Gln Ser Ile Leu Ser
1               5                   10                  15

Pro Ser Pro Tyr Glu Gly Tyr Arg
            20

<210> SEQ ID NO 306
<211> LENGTH: 23
<212> TYPE: PRT
<213> ORGANISM: Homo sapiens

<400> SEQUENCE: 306

Arg His Gln Leu Leu Cys Phe Lys Glu Asp Cys Gln Ala Val Phe Gln
1               5                   10                  15

Asp Leu Glu Gly Val Glu Lys
            20

<210> SEQ ID NO 307
<211> LENGTH: 16
<212> TYPE: PRT
<213> ORGANISM: Homo sapiens

<400> SEQUENCE: 307

Gly Pro Asp Ile Leu Arg Thr Tyr Ser Gly Ala Phe Val Cys Leu Glu
1               5                   10                  15

<210> SEQ ID NO 308
<211> LENGTH: 12
<212> TYPE: PRT
<213> ORGANISM: Homo sapiens

<400> SEQUENCE: 308

Cys Ser Leu Gly Leu Ala Leu Arg Arg Trp Arg Pro
1               5                   10

<210> SEQ ID NO 309
<211> LENGTH: 20
<212> TYPE: PRT
<213> ORGANISM: Homo sapiens

<400> SEQUENCE: 309

Arg Tyr Leu Thr Leu Asp Ile Phe Ala Gly Pro Pro Asn Tyr Pro Phe
1               5                   10                  15

Ser Asp Glu Tyr
            20

<210> SEQ ID NO 310
<211> LENGTH: 20

```
<212> TYPE: PRT
<213> ORGANISM: Homo sapiens

<400> SEQUENCE: 310

Arg Tyr Leu Thr Leu Asp Ile Phe Ala Gly Pro Pro Asn Tyr Pro Phe
1               5                   10                  15

Ser Asp Glu Tyr
            20

<210> SEQ ID NO 311
<211> LENGTH: 20
<212> TYPE: PRT
<213> ORGANISM: Homo sapiens

<400> SEQUENCE: 311

His Tyr Phe Asn Ser Asp Ser Phe Ala Ser His Pro Asn Tyr Pro Tyr
1               5                   10                  15

Ser Asp Glu Tyr
            20

<210> SEQ ID NO 312
<211> LENGTH: 20
<212> TYPE: PRT
<213> ORGANISM: Homo sapiens

<400> SEQUENCE: 312

His Tyr Phe Asn Ser Asp Ser Phe Ala Ser His Pro Asn Tyr Pro Tyr
1               5                   10                  15

Ser Asp Glu Tyr
            20

<210> SEQ ID NO 313
<211> LENGTH: 20
<212> TYPE: PRT
<213> ORGANISM: Homo sapiens

<400> SEQUENCE: 313

Arg Tyr Val Val Met Asp Phe Leu Met Asp His Pro Asp Tyr Pro Phe
1               5                   10                  15

Ser Asp Glu Tyr
            20

<210> SEQ ID NO 314
<211> LENGTH: 20
<212> TYPE: PRT
<213> ORGANISM: Homo sapiens

<400> SEQUENCE: 314

Arg Tyr Val Val Met Asp Phe Leu Met Asp His Pro Asp Tyr Pro Phe
1               5                   10                  15

Ser Asp Glu Tyr
            20

<210> SEQ ID NO 315
<211> LENGTH: 17
<212> TYPE: PRT
<213> ORGANISM: Homo sapiens

<400> SEQUENCE: 315

Asp Pro Ala Lys Val Gln Ser Leu Val Asp Thr Ile Arg Glu Asp Pro
1               5                   10                  15

Asp
```

```
<210> SEQ ID NO 316
<211> LENGTH: 17
<212> TYPE: PRT
<213> ORGANISM: Homo sapiens

<400> SEQUENCE: 316

Arg Glu Thr Ile Pro Ala Lys Leu Val Gln Ser Thr Leu Ser Asp Leu
1               5                   10                  15

Arg

<210> SEQ ID NO 317
<211> LENGTH: 17
<212> TYPE: PRT
<213> ORGANISM: Homo sapiens

<400> SEQUENCE: 317

Ser Asp Thr Thr Glu Glu Leu Thr Val Ile Lys Ser Ser Leu Lys Asp
1               5                   10                  15

Glu

<210> SEQ ID NO 318
<211> LENGTH: 16
<212> TYPE: PRT
<213> ORGANISM: Homo sapiens

<400> SEQUENCE: 318

His Ser Arg Ser Ser Leu Met Pro Leu Arg Asn Asp Val Asp Lys Arg
1               5                   10                  15

<210> SEQ ID NO 319
<211> LENGTH: 20
<212> TYPE: PRT
<213> ORGANISM: Homo sapiens

<400> SEQUENCE: 319

Tyr Arg Asn Pro Tyr Val Glu Ala Glu Tyr Phe Pro Thr Lys Pro Met
1               5                   10                  15

Phe Val Ile Ala
            20

<210> SEQ ID NO 320
<211> LENGTH: 20
<212> TYPE: PRT
<213> ORGANISM: Homo sapiens

<400> SEQUENCE: 320

Lys Lys Phe Pro Arg Phe Arg Asn Arg Glu Leu Glu Ala Thr Arg Arg
1               5                   10                  15

Gln Arg Met Asp
            20

<210> SEQ ID NO 321
<211> LENGTH: 14
<212> TYPE: PRT
<213> ORGANISM: Homo sapiens

<400> SEQUENCE: 321

Ser Gly Asn Thr Ala Ile Asn Tyr Lys His Ser Ser Ile Pro
1               5                   10

<210> SEQ ID NO 322
```

```
<211> LENGTH: 20
<212> TYPE: PRT
<213> ORGANISM: Homo sapiens

<400> SEQUENCE: 322

Asp Ala Asn Thr Cys Gly Glu Asp Lys Gly Ser Arg Arg Lys Phe Leu
1               5                   10                  15

Asp Gly Asp Glu
            20

<210> SEQ ID NO 323
<211> LENGTH: 20
<212> TYPE: PRT
<213> ORGANISM: Homo sapiens

<400> SEQUENCE: 323

Gln Leu Glu Glu Met Thr Glu Leu Glu Ser Pro Lys Cys Lys Arg Gln
1               5                   10                  15

Glu Asn Glu Gln
            20

<210> SEQ ID NO 324
<211> LENGTH: 20
<212> TYPE: PRT
<213> ORGANISM: Homo sapiens

<400> SEQUENCE: 324

Gln Ala Asp Gly Ala Ala Ser Ala Pro Thr Glu Glu Glu Glu Glu Val
1               5                   10                  15

Val Lys Asp Arg
            20

<210> SEQ ID NO 325
<211> LENGTH: 20
<212> TYPE: PRT
<213> ORGANISM: Homo sapiens

<400> SEQUENCE: 325

Ser Gly Asp Ser Leu Glu Thr Lys Glu Asp Gln Lys Met Ser Pro Lys
1               5                   10                  15

Ala Thr Glu Glu
            20

<210> SEQ ID NO 326
<211> LENGTH: 20
<212> TYPE: PRT
<213> ORGANISM: Homo sapiens

<400> SEQUENCE: 326

Arg Lys Ser Val Lys Arg Met Lys Glu Ser Arg Leu Glu Asp Thr Gln
1               5                   10                  15

Lys His Arg Val
            20

<210> SEQ ID NO 327
<211> LENGTH: 20
<212> TYPE: PRT
<213> ORGANISM: Homo sapiens

<400> SEQUENCE: 327

Lys Ile Arg Leu Pro Glu Arg Glu Lys Pro Asp Arg Glu Arg Asn Ala
1               5                   10                  15
```

Arg Arg Glu Pro
            20

<210> SEQ ID NO 328
<211> LENGTH: 20
<212> TYPE: PRT
<213> ORGANISM: Homo sapiens

<400> SEQUENCE: 328

Arg Gly Thr Lys Cys Leu Arg Arg Glu Ala Pro Arg Trp Asp Ala Pro
1               5                   10                  15

Leu Arg Asp Pro
            20

<210> SEQ ID NO 329
<211> LENGTH: 20
<212> TYPE: PRT
<213> ORGANISM: Homo sapiens

<400> SEQUENCE: 329

Gly Thr Arg Ser Arg Ser His Thr Ser Glu Gly Arg Thr Ser Arg Ser
1               5                   10                  15

His Thr Ser Glu
            20

<210> SEQ ID NO 330
<211> LENGTH: 18
<212> TYPE: PRT
<213> ORGANISM: Homo sapiens

<400> SEQUENCE: 330

Glu Glu Thr Thr Ala Asp Gly Arg Lys Thr Gln Thr Val Cys Asn Phe
1               5                   10                  15

Thr Asp

<210> SEQ ID NO 331
<211> LENGTH: 16
<212> TYPE: PRT
<213> ORGANISM: Homo sapiens

<400> SEQUENCE: 331

Ala Lys Arg Lys Arg Ser Ala Pro Glu Lys Ser Ser Gly Asp Val Pro
1               5                   10                  15

<210> SEQ ID NO 332
<211> LENGTH: 20
<212> TYPE: PRT
<213> ORGANISM: Homo sapiens

<400> SEQUENCE: 332

Arg Val Asp Arg Pro Gly Ser Arg Tyr Asp Val Ser Arg Leu Gly Arg
1               5                   10                  15

Gly Lys Arg Ser
            20

<210> SEQ ID NO 333
<211> LENGTH: 17
<212> TYPE: PRT
<213> ORGANISM: Homo sapiens

<400> SEQUENCE: 333

Glu Thr Val Asp Lys Leu Leu Lys Gly Tyr Asp Ile Arg Leu Arg Pro
1               5                   10                  15

Asp

<210> SEQ ID NO 334
<211> LENGTH: 20
<212> TYPE: PRT
<213> ORGANISM: Homo sapiens

<400> SEQUENCE: 334

Ala Pro Gly Gly Ala Glu Asp Leu Glu Asp Thr Gln Phe Pro Ser Glu
1               5                   10                  15

Glu Ala Arg Glu
            20

<210> SEQ ID NO 335
<211> LENGTH: 20
<212> TYPE: PRT
<213> ORGANISM: Homo sapiens

<400> SEQUENCE: 335

Arg Lys Ser Ser Arg Thr Leu Lys Lys Gly Pro Arg Gln Asp Pro Ser
1               5                   10                  15

Ala Ile Val Glu
            20

<210> SEQ ID NO 336
<211> LENGTH: 20
<212> TYPE: PRT
<213> ORGANISM: Homo sapiens

<400> SEQUENCE: 336

Gly Ser Glu Ser Gly Asp Ser Asp Glu Ser Glu Ser Lys Ser Glu Gln
1               5                   10                  15

Arg Thr Lys Arg
            20

<210> SEQ ID NO 337
<211> LENGTH: 20
<212> TYPE: PRT
<213> ORGANISM: Homo sapiens

<400> SEQUENCE: 337

Glu Ala Asp Ser Gly Asp Ala Arg Arg Leu Pro Arg Ala Arg Gly Glu
1               5                   10                  15

Arg Arg Arg His
            20

<210> SEQ ID NO 338
<211> LENGTH: 19
<212> TYPE: PRT
<213> ORGANISM: Homo sapiens

<400> SEQUENCE: 338

Arg Leu Glu Arg Pro Gln Asp Arg Asp Thr Pro Val Gln Asn Lys Arg
1               5                   10                  15

Arg Arg Ser

<210> SEQ ID NO 339
<211> LENGTH: 19
<212> TYPE: PRT
<213> ORGANISM: Homo sapiens

<400> SEQUENCE: 339

-continued

Asp Arg Val Glu Asp Val Met Met Glu Arg Glu Ser Gln Phe Lys Glu
1               5                   10                  15

Lys Gln Glu

<210> SEQ ID NO 340
<211> LENGTH: 17
<212> TYPE: PRT
<213> ORGANISM: Homo sapiens

<400> SEQUENCE: 340

Asp Glu Ala Phe Lys Arg Leu Gln Gly Lys Arg Asn Arg Gly Arg Glu
1               5                   10                  15

Glu

<210> SEQ ID NO 341
<211> LENGTH: 15
<212> TYPE: PRT
<213> ORGANISM: Homo sapiens

<400> SEQUENCE: 341

Arg Phe Gln Glu Glu Ile Lys Glu Asn Thr Lys Asn Asp Lys Gln
1               5                   10                  15

<210> SEQ ID NO 342
<211> LENGTH: 19
<212> TYPE: PRT
<213> ORGANISM: Homo sapiens

<400> SEQUENCE: 342

Lys Arg Asp Lys Glu Gly Val Arg Trp Thr Lys Cys Asn Lys Lys Thr
1               5                   10                  15

Leu Thr Asp

<210> SEQ ID NO 343
<211> LENGTH: 19
<212> TYPE: PRT
<213> ORGANISM: Homo sapiens

<400> SEQUENCE: 343

Lys Glu Gly Ser Leu Leu Ser Lys Gln Glu Glu Ser Lys Ala Ala Phe
1               5                   10                  15

Gly Glu Glu

<210> SEQ ID NO 344
<211> LENGTH: 19
<212> TYPE: PRT
<213> ORGANISM: Homo sapiens

<400> SEQUENCE: 344

Glu Ser Asp Ala Gly Lys Glu Lys Leu Pro Lys Met Arg Leu Pro Thr
1               5                   10                  15

Arg Ser Asp

<210> SEQ ID NO 345
<211> LENGTH: 19
<212> TYPE: PRT
<213> ORGANISM: Homo sapiens

<400> SEQUENCE: 345

Glu Arg Asp Lys Gly Lys Thr Val Glu Val Gly Arg Ala Tyr Phe Glu
1               5                   10                  15

Thr Glu Lys

<210> SEQ ID NO 346
<211> LENGTH: 15
<212> TYPE: PRT
<213> ORGANISM: Homo sapiens

<400> SEQUENCE: 346

Glu Lys Phe Arg Val Glu Lys Asp Lys Leu Val Pro Glu Lys Arg
1               5                   10                  15

<210> SEQ ID NO 347
<211> LENGTH: 19
<212> TYPE: PRT
<213> ORGANISM: Homo sapiens

<400> SEQUENCE: 347

Glu Val Ala Glu Lys Arg Arg Lys Ala Leu Tyr Glu Ala Leu Lys Glu
1               5                   10                  15

Asn Glu Lys

<210> SEQ ID NO 348
<211> LENGTH: 18
<212> TYPE: PRT
<213> ORGANISM: Homo sapiens

<400> SEQUENCE: 348

Glu Asn Tyr Glu Asp Asp Asp Leu Val Asn Ser Asp Glu Val Met Lys
1               5                   10                  15

Lys Pro

<210> SEQ ID NO 349
<211> LENGTH: 17
<212> TYPE: PRT
<213> ORGANISM: Homo sapiens

<400> SEQUENCE: 349

Pro Lys Ala Asp Glu Ile Arg Thr Leu Val Lys Asp Met Trp Asp Thr
1               5                   10                  15

Arg

<210> SEQ ID NO 350
<211> LENGTH: 19
<212> TYPE: PRT
<213> ORGANISM: Homo sapiens

<400> SEQUENCE: 350

Arg Lys Arg Cys Leu Glu Asp Ser Glu Asp Phe Gly Val Lys Lys Ala
1               5                   10                  15

Arg Thr Glu

<210> SEQ ID NO 351
<211> LENGTH: 19
<212> TYPE: PRT
<213> ORGANISM: Homo sapiens

<400> SEQUENCE: 351

Glu Pro Lys Ser Phe Leu Cys Arg Leu Cys Cys Gln Glu Asp Pro Glu
1               5                   10                  15

Leu Asp Ser

<210> SEQ ID NO 352
<211> LENGTH: 18
<212> TYPE: PRT
<213> ORGANISM: Homo sapiens

<400> SEQUENCE: 352

Glu Glu Tyr Asp Arg Glu Ser Lys Ser Ser Asp Asp Val Asp Tyr Arg
1               5                   10                  15

Gly Ser

<210> SEQ ID NO 353
<211> LENGTH: 18
<212> TYPE: PRT
<213> ORGANISM: Homo sapiens

<400> SEQUENCE: 353

Cys Val Asn Gly Glu Ile Glu Gly Leu Asn Asp Thr Phe Lys Glu Leu
1               5                   10                  15

Glu Phe

<210> SEQ ID NO 354
<211> LENGTH: 16
<212> TYPE: PRT
<213> ORGANISM: Homo sapiens

<400> SEQUENCE: 354

Glu Gln Arg Ala Arg Trp Glu Arg Lys Arg Ala Cys Thr Ala Arg Glu
1               5                   10                  15

<210> SEQ ID NO 355
<211> LENGTH: 17
<212> TYPE: PRT
<213> ORGANISM: Homo sapiens

<400> SEQUENCE: 355

Glu Arg Lys Gln Leu Glu Cys Glu Gln Val Leu Gln Lys Leu Ala Lys
1               5                   10                  15

Glu

<210> SEQ ID NO 356
<211> LENGTH: 19
<212> TYPE: PRT
<213> ORGANISM: Homo sapiens

<400> SEQUENCE: 356

Arg Asn Ser Glu Thr Lys Val Arg Arg Ser Thr Arg Leu Gln Lys Asp
1               5                   10                  15

Leu Glu Asn

<210> SEQ ID NO 357
<211> LENGTH: 16
<212> TYPE: PRT
<213> ORGANISM: Homo sapiens

<400> SEQUENCE: 357

Ser Asp Tyr Gln Val Ile Ser Asp Arg Gln Thr Pro Lys Lys Asp Glu
1               5                   10                  15

<210> SEQ ID NO 358
<211> LENGTH: 15
<212> TYPE: PRT
<213> ORGANISM: Homo sapiens

<400> SEQUENCE: 358

Asp Ile Glu Gly Lys Leu Pro Gln Thr Glu Gln Glu Leu Lys Glu
1               5                   10                  15

<210> SEQ ID NO 359
<211> LENGTH: 19
<212> TYPE: PRT
<213> ORGANISM: Homo sapiens

<400> SEQUENCE: 359

Asp Asp Val Asn Tyr Lys Met His Phe Arg Met Ile Asn Glu Gln Gln
1               5                   10                  15

Val Glu Asp

<210> SEQ ID NO 360
<211> LENGTH: 17
<212> TYPE: PRT
<213> ORGANISM: Homo sapiens

<400> SEQUENCE: 360

Glu Asn Pro Leu Pro Glu Arg Pro Arg Glu Lys Glu Glu Pro Val Val
1               5                   10                  15

Arg

<210> SEQ ID NO 361
<211> LENGTH: 19
<212> TYPE: PRT
<213> ORGANISM: Homo sapiens

<400> SEQUENCE: 361

Arg Glu Gln Ser Glu Gly Val Gly Ala Arg Val Arg Arg Ser Ile Gly
1               5                   10                  15

Arg Pro Glu

<210> SEQ ID NO 362
<211> LENGTH: 19
<212> TYPE: PRT
<213> ORGANISM: Homo sapiens

<400> SEQUENCE: 362

Pro Arg Ala Val Ala Gly Lys Glu Glu Asp Ser Asp Pro Glu Lys
1               5                   10                  15

Ala Leu Arg

<210> SEQ ID NO 363
<211> LENGTH: 17
<212> TYPE: PRT
<213> ORGANISM: Homo sapiens

<400> SEQUENCE: 363

Glu Lys Ala Asp Thr Asp Met Glu Gly Ser Val Asp Thr Arg Gln Glu
1               5                   10                  15

Lys

<210> SEQ ID NO 364
<211> LENGTH: 19
<212> TYPE: PRT
<213> ORGANISM: Homo sapiens

<400> SEQUENCE: 364

```
Arg Val Gln Asn His Asp Asn Pro Lys Trp Glu Ala Lys Lys Glu Asn
1               5                   10                  15

Ile Ser Lys

<210> SEQ ID NO 365
<211> LENGTH: 19
<212> TYPE: PRT
<213> ORGANISM: Homo sapiens

<400> SEQUENCE: 365

Arg Ser Pro Pro Ala Lys Gly Ala Thr Gly Pro Glu Glu Gln Ser Asp
1               5                   10                  15

Ser Leu Lys

<210> SEQ ID NO 366
<211> LENGTH: 19
<212> TYPE: PRT
<213> ORGANISM: Homo sapiens

<400> SEQUENCE: 366

Arg Glu Glu Asp Phe Lys Ala Thr Glu Ile Ile Glu Pro Ser Lys Gln
1               5                   10                  15

Asp Lys Pro

<210> SEQ ID NO 367
<211> LENGTH: 15
<212> TYPE: PRT
<213> ORGANISM: Homo sapiens

<400> SEQUENCE: 367

Asp Lys Thr Cys Met Lys Trp Ser Thr Asn Ser Cys Gly Ala Gln
1               5                   10                  15

<210> SEQ ID NO 368
<211> LENGTH: 14
<212> TYPE: PRT
<213> ORGANISM: Homo sapiens

<400> SEQUENCE: 368

Asp Ala Asn Leu Ser Lys Asn Gly Gly Leu Glu Val Trp Leu
1               5                   10

<210> SEQ ID NO 369
<211> LENGTH: 10
<212> TYPE: PRT
<213> ORGANISM: Homo sapiens

<400> SEQUENCE: 369

Glu Pro Phe Leu Pro Lys Leu Leu Thr Lys
1               5                   10

<210> SEQ ID NO 370
<211> LENGTH: 19
<212> TYPE: PRT
<213> ORGANISM: Homo sapiens

<400> SEQUENCE: 370

Arg Lys Ser Glu Ala Gly Ser Gly Ala Ala Ser Ser Ser Gly Glu Asp
1               5                   10                  15

Lys Glu Asn

<210> SEQ ID NO 371
```

-continued

<210> SEQ ID NO 371 (continued)
<211> LENGTH: 19
<212> TYPE: PRT
<213> ORGANISM: Homo sapiens

<400> SEQUENCE: 371

Asp Asp Ile Tyr Asp Pro Thr Tyr Lys Asp Lys Glu Gly Pro Ser Pro
1               5                   10                  15

Lys Val Glu

<210> SEQ ID NO 372
<211> LENGTH: 19
<212> TYPE: PRT
<213> ORGANISM: Homo sapiens

<400> SEQUENCE: 372

Gln Ser Asp Glu Ala Lys Asn Asn Met Lys Gly Leu Pro Glu Leu Glu
1               5                   10                  15

Lys Lys Asp

<210> SEQ ID NO 373
<211> LENGTH: 19
<212> TYPE: PRT
<213> ORGANISM: Homo sapiens

<400> SEQUENCE: 373

Ser Arg Pro Gln Gly Leu Thr Glu Ala Glu Gln Arg Glu Leu Glu Gln
1               5                   10                  15

Glu Ala Lys

<210> SEQ ID NO 374
<211> LENGTH: 14
<212> TYPE: PRT
<213> ORGANISM: Homo sapiens

<400> SEQUENCE: 374

Arg Val Gln Gln Lys Gly Thr Ser Glu Thr Asp Thr Ile Cys
1               5                   10

<210> SEQ ID NO 375
<211> LENGTH: 16
<212> TYPE: PRT
<213> ORGANISM: Homo sapiens

<400> SEQUENCE: 375

Val Arg Leu Ser Pro Leu Ala Glu Arg Gln Leu Gln Val Gln Trp Glu
1               5                   10                  15

<210> SEQ ID NO 376
<211> LENGTH: 19
<212> TYPE: PRT
<213> ORGANISM: Homo sapiens

<400> SEQUENCE: 376

Arg Arg Ser Leu Gly Val Ser Val Arg Ser Trp Asp Glu Leu Pro Asp
1               5                   10                  15

Glu Lys Arg

<210> SEQ ID NO 377
<211> LENGTH: 17
<212> TYPE: PRT
<213> ORGANISM: Homo sapiens

<400> SEQUENCE: 377

```
Asp Gly Leu Gly Pro Asp Pro Pro His Arg Asp Arg Leu Arg Ser
1               5                   10                  15

Lys

<210> SEQ ID NO 378
<211> LENGTH: 18
<212> TYPE: PRT
<213> ORGANISM: Homo sapiens

<400> SEQUENCE: 378

Ser Gly Lys Arg Ser Ser Asp Gly Ser Leu Ser His Glu Glu Asp Leu
1               5                   10                  15

Ala Lys

<210> SEQ ID NO 379
<211> LENGTH: 19
<212> TYPE: PRT
<213> ORGANISM: Homo sapiens

<400> SEQUENCE: 379

Ser Gln Glu Arg Ser Asp Ser Pro Glu Ile Cys His Tyr Glu Lys Ser
1               5                   10                  15

Phe His Lys

<210> SEQ ID NO 380
<211> LENGTH: 17
<212> TYPE: PRT
<213> ORGANISM: Homo sapiens

<400> SEQUENCE: 380

Lys Val Asn Pro Glu Pro Thr His Glu Ile Arg Cys Asn Ser Glu Val
1               5                   10                  15

Lys

<210> SEQ ID NO 381
<211> LENGTH: 17
<212> TYPE: PRT
<213> ORGANISM: Homo sapiens

<400> SEQUENCE: 381

Arg Glu Leu Arg Glu Val Leu Arg Thr Val Glu Thr Lys Ala Thr Gln
1               5                   10                  15

Asn

<210> SEQ ID NO 382
<211> LENGTH: 18
<212> TYPE: PRT
<213> ORGANISM: Homo sapiens

<400> SEQUENCE: 382

Arg Asp Thr Glu Asp Gln Glu Asp Gln Val Asp Pro Arg Leu Ile Asp
1               5                   10                  15

Gly Lys

<210> SEQ ID NO 383
<211> LENGTH: 16
<212> TYPE: PRT
<213> ORGANISM: Homo sapiens

<400> SEQUENCE: 383
```

```
Lys Asn His His Glu Leu Asp His Arg Glu Arg Glu Ser Ser Ala Asn
1               5                   10                  15
```

<210> SEQ ID NO 384
<211> LENGTH: 16
<212> TYPE: PRT
<213> ORGANISM: Homo sapiens

<400> SEQUENCE: 384

```
Ser Asp Gly Arg Gly Arg Pro Ala Phe Pro Phe Ser Cys Pro Arg Gln
1               5                   10                  15
```

<210> SEQ ID NO 385
<211> LENGTH: 15
<212> TYPE: PRT
<213> ORGANISM: Homo sapiens

<400> SEQUENCE: 385

```
Gly Ser Lys Glu Asp Phe Asp Ser Leu Leu Gln Ser Ala Lys Lys
1               5                   10                  15
```

<210> SEQ ID NO 386
<211> LENGTH: 15
<212> TYPE: PRT
<213> ORGANISM: Homo sapiens

<400> SEQUENCE: 386

```
Glu Tyr Arg Asn Gln Thr Asn Leu Pro Thr Glu Asn Val Asp Lys
1               5                   10                  15
```

<210> SEQ ID NO 387
<211> LENGTH: 18
<212> TYPE: PRT
<213> ORGANISM: Homo sapiens

<400> SEQUENCE: 387

```
Gln Lys Glu Glu Lys Thr Trp His Glu Ala Leu Arg Ser Cys Gln Ala
1               5                   10                  15

Asp Asn
```

<210> SEQ ID NO 388
<211> LENGTH: 17
<212> TYPE: PRT
<213> ORGANISM: Homo sapiens

<400> SEQUENCE: 388

```
Glu Lys Ala Glu Glu Gly Pro Arg Lys Arg Glu Pro Ala Pro Leu Asp
1               5                   10                  15

Lys
```

<210> SEQ ID NO 389
<211> LENGTH: 14
<212> TYPE: PRT
<213> ORGANISM: Homo sapiens

<400> SEQUENCE: 389

```
Glu Gln Asn Arg Asp Arg Ile Leu Thr Pro Glu Asn Arg Lys
1               5                   10
```

<210> SEQ ID NO 390
<211> LENGTH: 14
<212> TYPE: PRT
<213> ORGANISM: Homo sapiens -continued

```
<400> SEQUENCE: 390

Arg Asp Trp Tyr Ile Gly Leu Val Ser Asp Glu Lys Trp Lys
1               5                   10

<210> SEQ ID NO 391
<211> LENGTH: 17
<212> TYPE: PRT
<213> ORGANISM: Homo sapiens

<400> SEQUENCE: 391

Asp Ser Tyr Leu Lys Thr Arg Ser Pro Val Thr Phe Leu Ser Asp Leu
1               5                   10                  15

Arg

<210> SEQ ID NO 392
<211> LENGTH: 17
<212> TYPE: PRT
<213> ORGANISM: Homo sapiens

<400> SEQUENCE: 392

Lys Cys Arg Gly Glu Thr Val Ala Lys Glu Ile Ser Glu Ala Met Lys
1               5                   10                  15

Ser

<210> SEQ ID NO 393
<211> LENGTH: 16
<212> TYPE: PRT
<213> ORGANISM: Homo sapiens

<400> SEQUENCE: 393

Gln Arg Gly Ser Gln Ile Gly Arg Glu Pro Ile Gly Leu Ser Gly Asp
1               5                   10                  15

<210> SEQ ID NO 394
<211> LENGTH: 17
<212> TYPE: PRT
<213> ORGANISM: Homo sapiens

<400> SEQUENCE: 394

Lys Pro Pro Gln Glu Thr Glu Lys Gly His Ser Ala Cys Glu Pro Glu
1               5                   10                  15

Asn

<210> SEQ ID NO 395
<211> LENGTH: 14
<212> TYPE: PRT
<213> ORGANISM: Homo sapiens

<400> SEQUENCE: 395

Glu Arg Arg Ala Gly Ser Gly Ala Arg Asp Ala Glu Arg Glu
1               5                   10

<210> SEQ ID NO 396
<211> LENGTH: 16
<212> TYPE: PRT
<213> ORGANISM: Homo sapiens

<400> SEQUENCE: 396

Ser Glu Gln Lys Ala Asp Pro Pro Ala Thr Glu Lys Thr Leu Leu Glu
1               5                   10                  15

<210> SEQ ID NO 397
```

```
<211> LENGTH: 19
<212> TYPE: PRT
<213> ORGANISM: Homo sapiens

<400> SEQUENCE: 397

Glu Ala Glu Trp Ser Gln Gly Val Gln Gly Thr Leu Arg Ile Lys Lys
1               5                   10                  15
Tyr Leu Thr

<210> SEQ ID NO 398
<211> LENGTH: 17
<212> TYPE: PRT
<213> ORGANISM: Homo sapiens

<400> SEQUENCE: 398

Glu Glu Ser Lys Ser Ile Thr Glu Gly Leu Leu Thr Gln Lys Gln Tyr
1               5                   10                  15
Glu

<210> SEQ ID NO 399
<211> LENGTH: 16
<212> TYPE: PRT
<213> ORGANISM: Homo sapiens

<400> SEQUENCE: 399

Gln Asn Phe Lys Asp Ala Phe Ser Gly Arg Asp Ser Ser Ile Thr Arg
1               5                   10                  15

<210> SEQ ID NO 400
<211> LENGTH: 16
<212> TYPE: PRT
<213> ORGANISM: Homo sapiens

<400> SEQUENCE: 400

Glu Lys Ile His Leu Asp Asp Ala Asn Glu Ser Asp His Phe Glu Asn
1               5                   10                  15

<210> SEQ ID NO 401
<211> LENGTH: 15
<212> TYPE: PRT
<213> ORGANISM: Homo sapiens

<400> SEQUENCE: 401

Thr Glu Asp Val Asp Glu Phe Arg Asn Lys Leu Gln Gly Glu Arg
1               5                   10                  15

<210> SEQ ID NO 402
<211> LENGTH: 20
<212> TYPE: PRT
<213> ORGANISM: Homo sapiens

<400> SEQUENCE: 402

Lys Gly Asp Val Ser Asn Leu Asp Pro Asn Phe Ser Phe Glu Gly Thr
1               5                   10                  15
Lys Leu Asp Val
            20

<210> SEQ ID NO 403
<211> LENGTH: 16
<212> TYPE: PRT
<213> ORGANISM: Homo sapiens

<400> SEQUENCE: 403
```

```
Lys Ala Arg Ala Ala Val Ser Pro Gln Lys Arg Lys Ser Asp Gly Pro
1               5                   10                  15

<210> SEQ ID NO 404
<211> LENGTH: 17
<212> TYPE: PRT
<213> ORGANISM: Homo sapiens

<400> SEQUENCE: 404

Arg Gln Ile Pro Ala Pro Gln Gly Ala Val Leu Val Gln Arg Glu Lys
1               5                   10                  15

Asp
```

US 7,754,431 B2

TLE3 AS A MARKER FOR CHEMOTHERAPY

CROSS REFERENCE TO RELATED APPLICATION

This application is a continuation of U.S. patent application Ser. No. 12/277,920, filed Nov. 25, 2008, which claims priority to U.S. Provisional Patent Application Ser. No. 60/991,487, filed Nov. 30, 2007, both of which are hereby incorporated herein by reference in their entireties.

SEQUENCE LISTING

In accordance with 37 C.F.R. §1.52(e)(5), a Sequence Listing in the form of a text file (entitled "Sequence Listing.txt," created on Oct. 13, 2009, and 90 kilobytes) is incorporated herein by reference in its entirety.

BACKGROUND OF THE INVENTION

A major challenge of cancer treatment is the selection of chemotherapies that maximize efficacy and minimize toxicity for a given patient. Assays for cell surface markers, e.g., using immunohistochemistry (IHC), have provided means for dividing certain cancers into subclasses. For example, one factor considered in prognosis and treatment decisions for breast cancer is the presence or absence of the estrogen receptor (ER). ER-positive breast cancers typically respond much more readily to hormonal therapies such as tamoxifen, which acts as an anti-estrogen in breast tissue, than ER-negative cancers. Though useful, these analyses only in part predict the clinical behavior of breast cancers. There is phenotypic diversity present in cancers that current diagnostic tools fail to detect. As a consequence, there is still much controversy over how to stratify patients amongst potential treatments in order to optimize outcome (e.g., for breast cancer see "NIH Consensus Development Conference Statement: Adjuvant Therapy for Breast Cancer, Nov. 1-3, 2000", *J. Nat. Cancer Inst. Monographs,* 30:5-15, 2001 and Di Leo et al., *Int. J. Clin. Oncol.* 7:245-253, 2002). In particular, there is currently no tool for predicting a patient's likely response to treatment with paclitaxel, a chemotherapeutic with particularly adverse side-effects. There clearly exists a need for improved methods and reagents for classifying cancers and thereby selecting therapeutic regimens that maximize efficacy and minimize toxicity for a given patient.

SUMMARY OF THE INVENTION

We have identified a correlation between the expression of TLE3 (transducin-like enhancer of split 3, Entrez Gene ID 7090) and a cancer's response to chemotherapy. This correlation has been demonstrated using TLE3 antibodies and samples from breast cancer cohorts which include both treated and untreated patients with known outcome. The inventors have also observed that binding of TLE3 antibodies in samples from treated ovarian cancer patients correlates with improved prognosis. In one aspect, the present invention therefore provides methods of using TLE3 as a marker for predicting the likelihood that a patient's cancer will respond to chemotherapy. In another aspect, the present invention provides methods of using TLE3 as a marker for deciding whether to administer chemotherapy to a cancer patient. In yet another aspect, the present invention provides methods of using TLE3 as a marker for selecting a chemotherapy for a cancer patient.

Expression of TLE3 can be detected using any known method. Thus, while the inventive methods have been exemplified by detecting TLE3 polypeptides using antibodies, in certain embodiments TLE3 polynucleotides may be detected using one or more primers as is well known in the art.

In general, TLE3 can be used in conjunction with other markers or clinical factors (e.g., stage, tumor size, node characteristics, age, etc.) to further improve the predictive power of the inventive methods.

BRIEF DESCRIPTION OF THE APPENDIX

This patent application refers to material comprising a table and data presented as Appendix A immediately after the section entitled "Exemplification" and immediately before the section entitled "Other Embodiments." Specifically, Appendix A is a table that lists a variety of markers that could be used in a panel in conjunction with the TLE3 marker in an inventive method. The table includes the antibody ID, parent gene name, Entrez Gene ID, known aliases for the parent gene, peptides that may be used in preparing antibodies and exemplary antibody titers for staining Using the parent gene name, Entrez Gene ID and/or known aliases for the parent gene, a skilled person can readily obtain the nucleotide (and corresponding amino acid) sequences for each and every one of the parent genes that are listed in Appendix A from a public database (e.g., GenBank, Swiss-Prot or any future derivative of these). The nucleotide and corresponding amino acid sequences for each and every one of the parent genes that are listed in Appendix A are hereby incorporated by reference from these public databases. Antibodies with IDs that begin with S5 or S6 may be obtained from commercial sources as indicated.

DEFINITIONS

Figure 1:
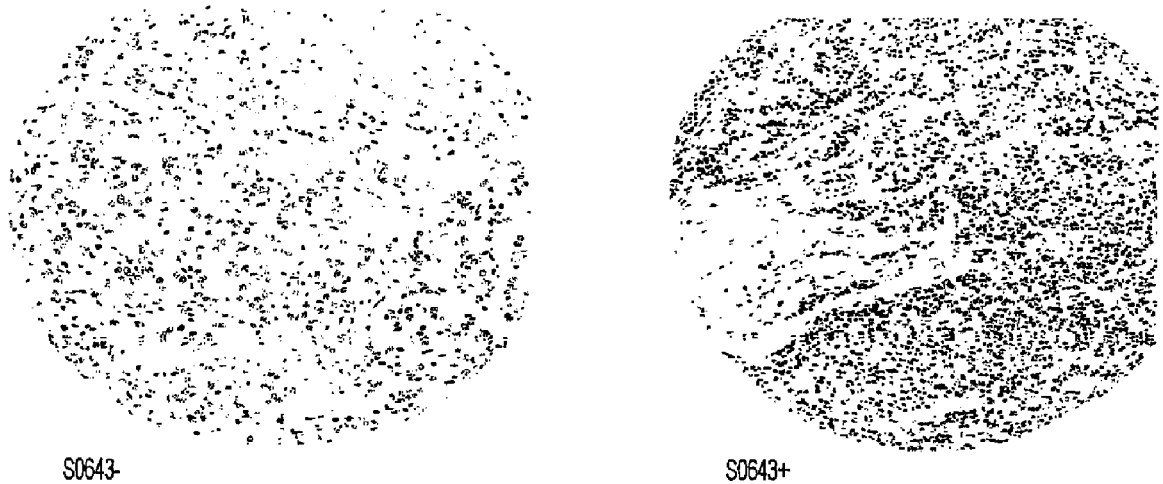
FIG. 1 compares IHC images of TLE3-negative (S0643−) and TLE3-positive (S0643+) samples from breast cancer patients.

Binds—When an interaction partner "binds" a marker they are linked by direct non-covalent interactions.

Cancer markers—"Cancer markers" or "markers" are molecular entities that are detectable in cancer samples. Generally, markers may be polypeptides (e.g., TLE3 protein) or polynucleotides (e.g., TLE3 mRNA) that are indicative of the expression of a gene (e.g., TLE3 gene) and present within the cancer sample, e.g., within the cytoplasm or membranes of cancerous cells and/or secreted from such cells.

Cancer sample—As used herein, the term "cancer sample" or "sample" is taken broadly to include cell or tissue samples removed from a cancer patient (e.g., from a tumor, from the bloodstream, etc.), cells derived from a tumor that may be located elsewhere in the body (e.g., cells in the bloodstream or at a site of metastasis), or any material derived from such a sample. Derived material may include, for example, nucleic acids or proteins extracted from the sample, cell progeny, etc. In one embodiment, a cancer sample may be a tumor sample.

Correlation—"Correlation" refers to the degree to which one variable can be predicted from another variable, e.g., the degree to which a cancer's response to therapy can be predicted from the expression of a marker in a cancer sample. A variety of statistical methods may be used to measure correlation between two variables, e.g., without limitation the student t-test, the Fisher exact test, the Pearson correlation coefficient, the Spearman correlation coefficient, the Chi squared test, etc. Results are traditionally given as a measured correlation coefficient with a p-value that provides a measure of the likelihood that the correlation arose by chance. A correlation with a p-value that is less than 0.05 is generally considered to be statistically significant. Preferred correlations have p-values that are less than 0.01, especially less than 0.001.

Hybridized—When a primer and a marker are physically "hybridized" with one another as described herein, they are non-covalently linked by base pair interactions.

Interaction partner—An "interaction partner" is an entity that binds a polypeptide marker. For example and without limitation, an interaction partner may be an antibody or a fragment thereof that binds a marker. In general, an interaction partner is said to "bind specifically" with a marker if it binds at a detectable level with the marker and does not bind detectably with unrelated molecular entities (e.g., other markers) under similar conditions. Specific association between a marker and an interaction partner will typically be dependent upon the presence of a particular structural feature of the target marker such as an antigenic determinant or epitope recognized by the interaction partner. In general, it is to be understood that specificity need not be absolute. For example, it is well known in the art that antibodies frequently cross-react with other epitopes in addition to the target epitope. Such cross-reactivity may be acceptable depending upon the application for which the interaction partner is to be used. Thus the degree of specificity of an interaction partner will depend on the context in which it is being used. In general, an interaction partner exhibits specificity for a particular marker if it favors binding with that partner above binding with other potential partners, e.g., other markers. One of ordinary skill in the art will be able to select interaction partners having a sufficient degree of specificity to perform appropriately in any given application (e.g., for detection of a target marker, for therapeutic purposes, etc.). It is also to be understood that specificity may be evaluated in the context of additional factors such as the affinity of the interaction partner for the target marker versus the affinity of the interaction partner for other potential partners, e.g., other markers. If an interaction partner exhibits a high affinity for a target marker and low affinity for non-target molecules, the interaction partner will likely be an acceptable reagent for diagnostic purposes even if it lacks specificity.

Primer—A "primer" is an oligonucleotide entity that physically hybridizes with a polynucleotide marker. In general, a primer is said to "hybridize specifically" with a marker if it hybridizes at a detectable level with the marker and does not hybridize detectably with unrelated molecular entities (e.g., other markers) under similar conditions. Specific hybridization between a marker and a primer will typically be dependent upon the presence of a particular nucleotide sequence of the target marker which is complementary to the nucleotide sequence of the primer. In general, it is to be understood that specificity need not be absolute. The degree of specificity of a primer will depend on the context in which it is being used. In general, a primer exhibits specificity for a particular marker if it favors hybridization with that partner above hybridization with other potential partners, e.g., other markers. One of ordinary skill in the art will be able to select primers having a sufficient degree of specificity to perform appropriately in any given application. It is also to be understood that specificity may be evaluated in the context of additional factors such as the affinity of the primer for the target marker versus the affinity of the primer for other potential partners, e.g., other markers. If a primer exhibits a high affinity for a target marker and low affinity for non-target molecules, the primer will likely be an acceptable reagent for diagnostic purposes even if it lacks specificity.

Response—The "response" of a cancer to therapy may represent any detectable change, for example at the molecular, cellular, organellar, or organismal level. For instance, tumor size, patient life expectancy, recurrence, or the length of time the patient survives, etc., are all responses. Responses can be measured in any of a variety of ways, including for example non-invasive measuring of tumor size (e.g., CT scan, image-enhanced visualization, etc.), invasive measuring of tumor size (e.g., residual tumor resection, etc.), surrogate marker measurement (e.g., serum PSA, etc.), clinical course variance (e.g., measurement of patient quality of life, time to relapse, survival time, etc.).

Small molecule—A "small molecule" is a non-polymeric molecule. A small molecule can be synthesized in a laboratory (e.g., by combinatorial synthesis) or found in nature (e.g., a natural product). A small molecule is typically characterized in that it contains several carbon-carbon bonds and has a molecular weight of less than about 1500 Da, although this characterization is not intended to be limiting for the purposes of the present invention.

DETAILED DESCRIPTION OF CERTAIN PREFERRED EMBODIMENTS OF THE INVENTION

As noted above, we have identified a correlation between the expression of TLE3 (transducin-like enhancer of split 3, Entrez Gene ID 7090) in a cancer sample and a cancer's response to chemotherapy. As described in the Examples, this correlation has been demonstrated using TLE3 antibodies and samples from two breast cancer cohorts which include both treated and untreated patients with known outcome. We have also shown that this predictive model is consistent when applied to samples from a cohort of treated ovarian cancer patients. We have also demonstrated the utility of TLE3 for predicting response to specific types of chemotherapies including treatments which involve the administration of cell cycle specific chemotherapeutics, e.g., methotrexate and taxanes. Since these chemotherapeutics have known utility across different cancer types, these results suggest that the inventive methods will also be useful in predicting their efficacy across different cancer types.

Predicting Response to Chemotherapy and Selecting Chemotherapy

In one aspect, the present invention provides methods of using TLE3 as a marker for predicting the likelihood that a patient's cancer will respond to chemotherapy. In general, these methods involve providing a cancer sample from a cancer patient, determining whether TLE3 is expressed in the cancer sample, and predicting the likelihood that the patient's cancer will respond to chemotherapy based upon a result of the step of determining. In one embodiment, the step of predicting comprises predicting that the patient's cancer is likely to respond to chemotherapy based upon the presence of TLE3 expression in the cancer sample. In one embodiment, the step of predicting comprises predicting that the patient's cancer is unlikely to respond to chemotherapy based upon the absence of TLE3 expression in the cancer sample.

In certain embodiments, a negative control sample is provided and the step of determining comprises detecting a level of TLE3 expression in the cancer sample and the negative control sample and comparing the level of expression of TLE3 in the cancer sample and the negative control sample. In general, the negative control sample can be any sample that does not reproducibly express TLE3. In one embodiment, the negative control sample can be a sample that does not reproducibly bind TLE3 antibodies. In one embodiment, the negative control sample can be a sample that does not reproducibly produce a detectable level of TLE3 mRNA. In one embodiment, the negative control sample can be from a patient with a TLE3-negative cancer. In one embodiment, the negative control sample can be from a patient without cancer. In certain embodiments the negative control sample may originate from the same tissue type as the cancer in question (e.g., breast tissue when considering breast cancer). In other embodiments, the negative control sample may originate from a different tissue type or even a different organism, or a cell line.

Additionally or alternatively, in certain embodiments, a positive control sample is provided and the step of determining comprises detecting a level of TLE3 expression in the cancer sample and the positive control sample and comparing the level of expression of TLE3 in the cancer sample and the positive control sample. In general, the positive control sample can be any sample that reproducibly expresses TLE3. In one embodiment, the negative control sample can be a sample that reproducibly bind TLE3 antibodies. In one embodiment, the negative control sample can be a sample that reproducibly produces a detectable level of TLE3 mRNA. In one embodiment, the positive control sample can be from a patient with a TLE3-positive cancer. In certain embodiments the positive control sample may originate from the same tissue type as the cancer in question (e.g., breast tissue when considering breast cancer). In other embodiments, the positive control sample may originate from a different tissue type or even a different organism, or cell line.

Expression of TLE3 can be determined using any known method.

In one embodiment, TLE3 polypeptides may be detected using an interaction partner that binds a TLE3 polypeptide (e.g., TLE3 protein or an antigenic fragment thereof). For example, as described below one may use a TLE3 antibody as an interaction partner and detect TLE3 expression by contacting the cancer sample with the TLE3 antibody. In such embodiments, the inventive methods may involve providing a cancer sample from a cancer patient, contacting the cancer sample with an antibody directed to TLE3, and predicting the likelihood that the patient's cancer will respond to chemotherapy based upon binding of the antibody to the cancer sample. In one embodiment, the step of predicting may comprise predicting that the patient's cancer is likely to respond to chemotherapy based upon binding of the antibody to the cancer sample. In another embodiment, the step of predicting may comprise predicting that the patient's cancer is unlikely to respond to chemotherapy based upon lack of binding of the antibody to the cancer sample.

In another embodiment, TLE3 polynucleotides may be detected using one or more primers that hybridize with a TLE3 polynucleotide (e.g., a TLE3 mRNA, cDNA or RNA). In such embodiments, the inventive methods may involve providing a cancer sample from a cancer patient, contacting the cancer sample with one or more primers that hybridize with TLE3, and predicting the likelihood that the patient's cancer will respond to chemotherapy based upon hybridization of the one or more primers to the cancer sample. In one embodiment, the step of predicting may comprise predicting that the patient's cancer is likely to respond to chemotherapy based upon hybridization of the one or more primers to the cancer sample. In another embodiment, the step of predicting may comprise predicting that the patient's cancer is unlikely to respond to chemotherapy based upon lack of hybridization of the one or more primers to the cancer sample.

In another aspect, the present invention provides methods for deciding whether to administer chemotherapy to the cancer patient based upon the likelihood that the patient's cancer will respond to chemotherapy. In one embodiment, the step of deciding comprises deciding to administer chemotherapy to the cancer patient based upon the presence of TLE3 expression in the cancer sample. In one embodiment, the step of deciding comprises deciding not to administer chemotherapy to the cancer patient based upon the absence of TLE3 expression in the cancer sample.

In yet another aspect, the present invention provides methods for selecting a chemotherapy for a cancer patient. In general, these methods comprise providing a cancer sample from a cancer patient, determining whether TLE3 is expressed in the cancer sample, and selecting a chemotherapy for the cancer patient based upon the results of the step of determining. In one embodiment, the step of selecting comprises selecting a chemotherapy based upon the presence of TLE3 expression in the cancer sample.

Figure 10:
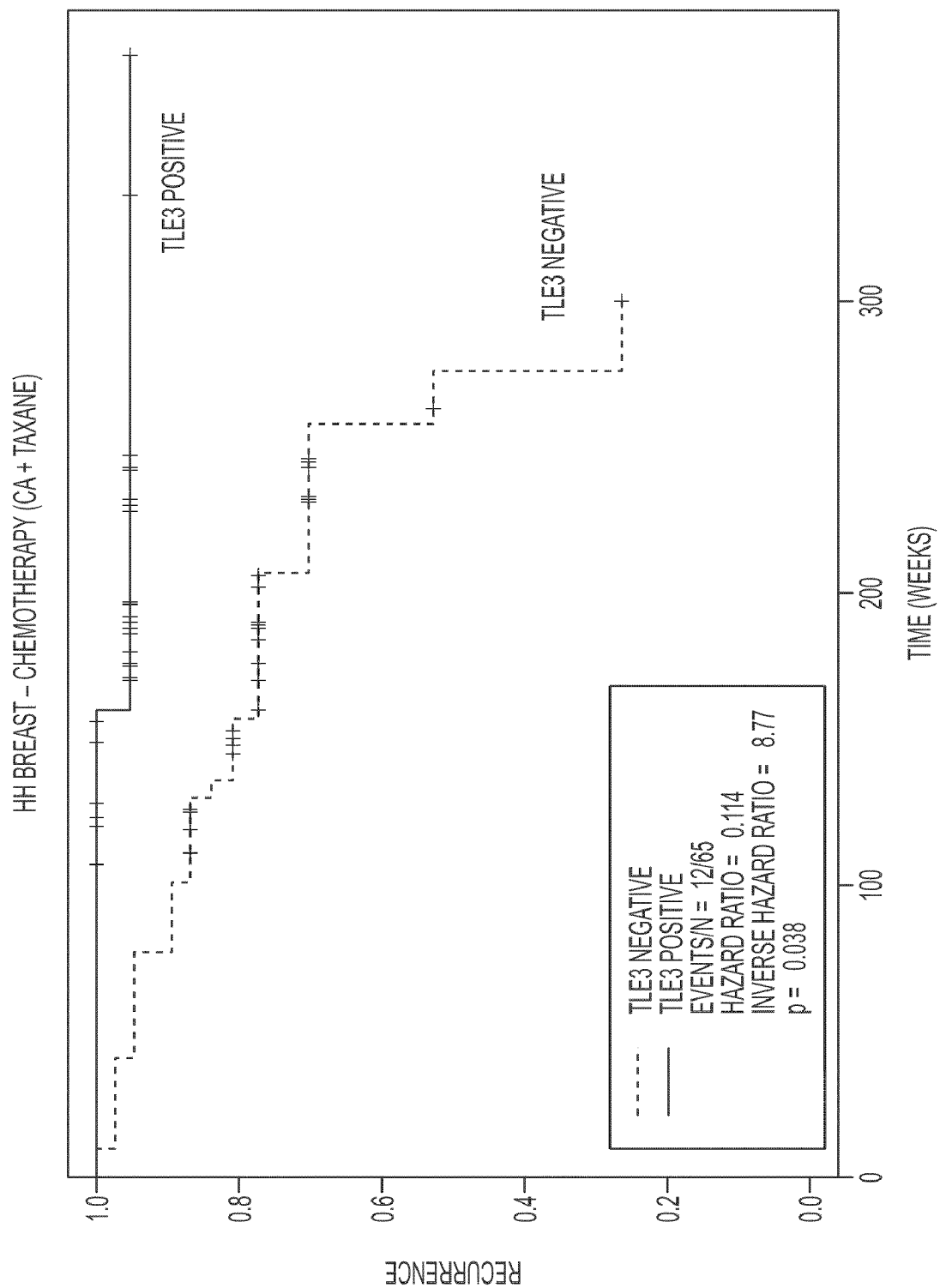
FIG. 10 shows Kaplan-Meier recurrence curves that were generated using patients in the HH breast cancer cohort of FIG. 8 that received CA or CAF in combination with a taxane. Recurrence data from TLE3-positive and TLE3-negative patients in this subset were used to generate the top and bottom curves, respectively. As shown in the Figure, the correlation between antibody binding to the TLE3 marker and prognosis was restored in this subset of treated patients (HR=0.114, p=0.038).
Figure 12:
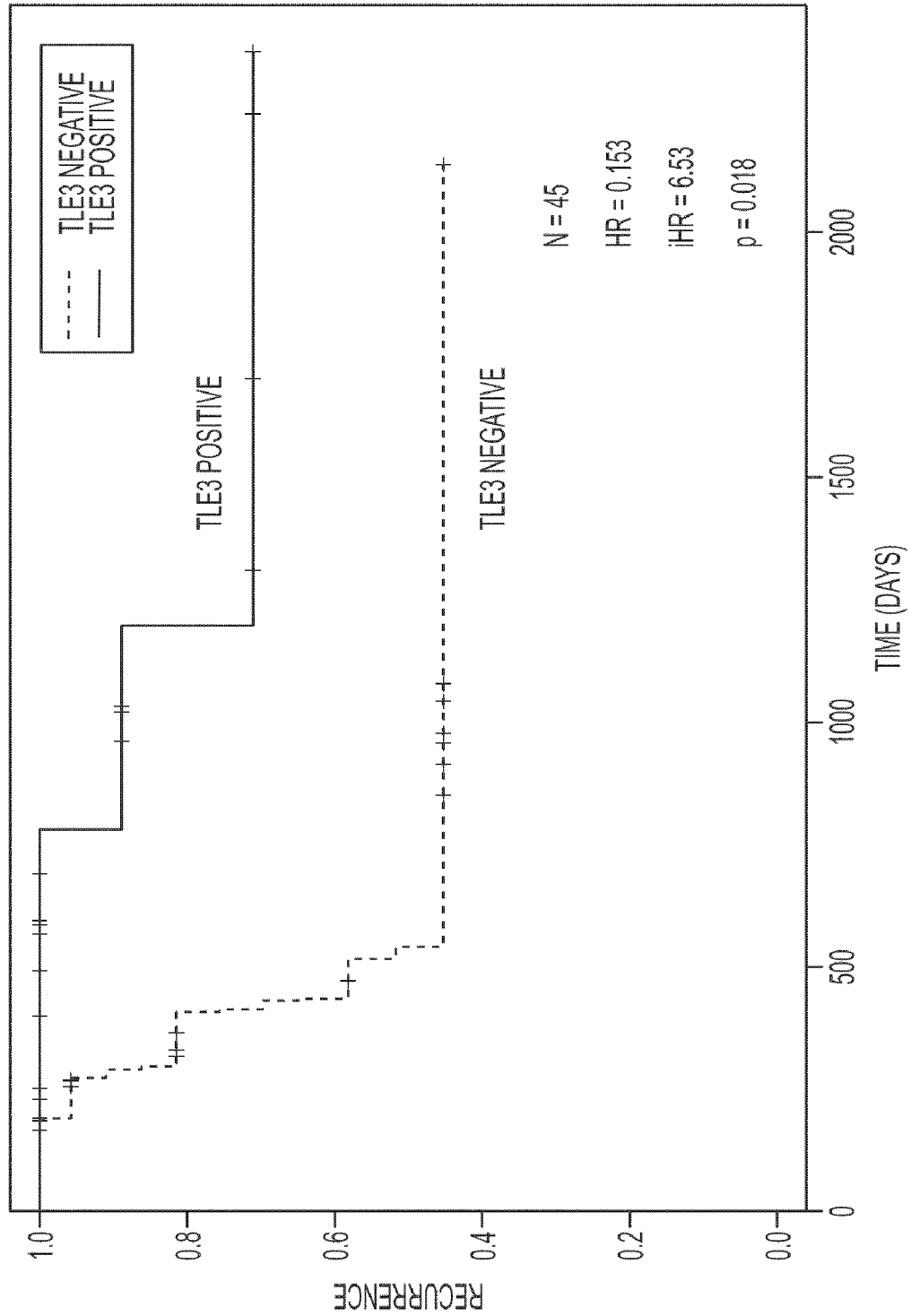
FIG. 12 shows Kaplan-Meier recurrence curves that were generated using patients in the RP breast cancer cohort of FIG. 6 that received CA in combination with a taxane. Recurrence data from TLE3-positive and TLE3-negative patients in this subset were used to generate the top and bottom curves, respectively. As shown in the Figure, antibody binding to the TLE3 marker correlates with improved prognosis across this subset of treated patients (HR=0.142, p=0.011).
Figure 13:
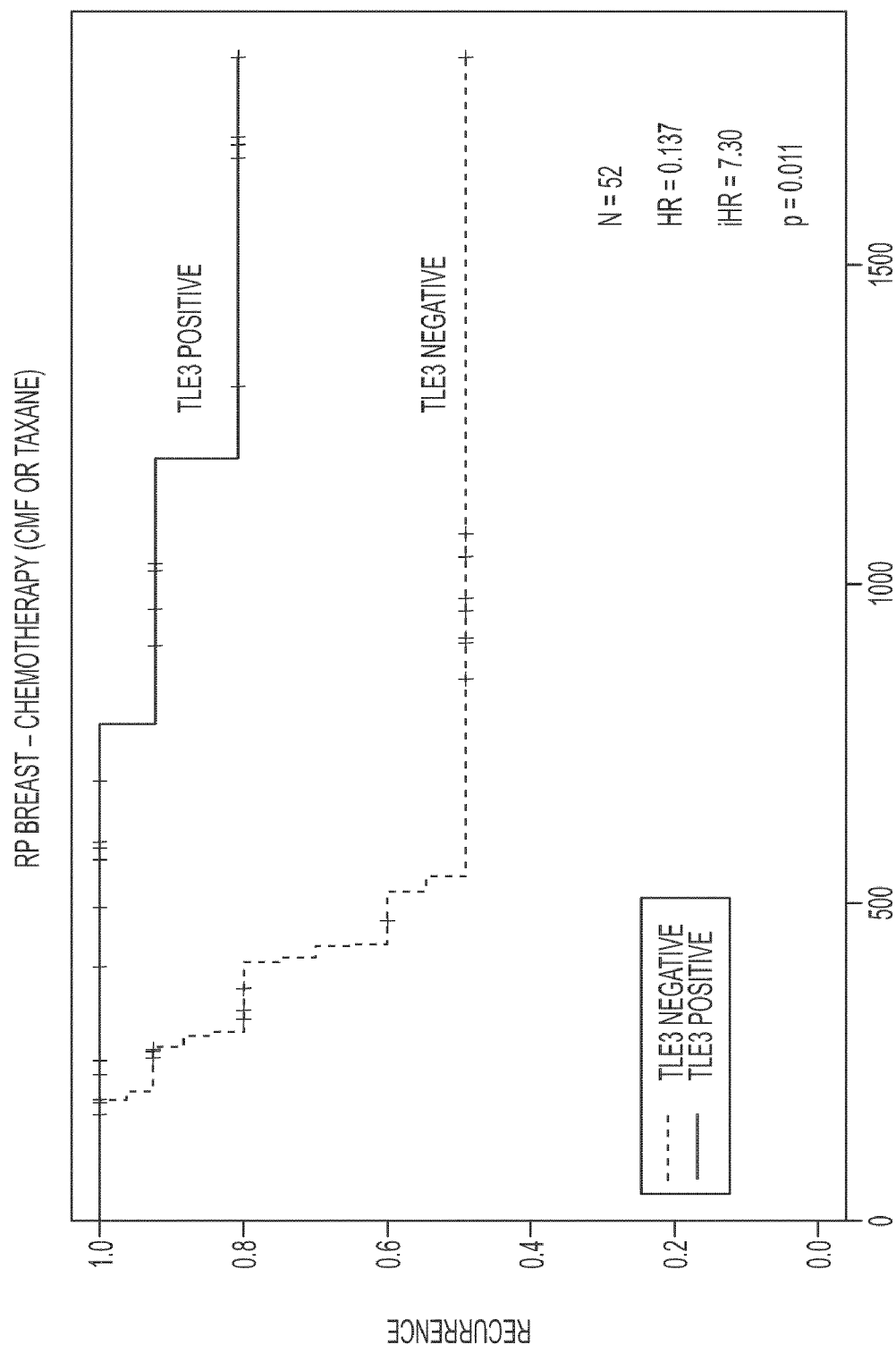
FIG. 13 shows Kaplan-Meier recurrence curves that were generated using patients in the RP breast cancer cohort of FIG. 6 that received a taxane or CMF. Some of the patients receiving a taxane also received CA. Recurrence data from TLE3-positive and TLE3-negative patients in this subset were used to generate the top and bottom curves, respectively. As shown in the Figure, antibody binding to the TLE3 marker correlates with improved prognosis across this subset of treated patients (HR=0.137, p=0.011).

As described in the Examples, we have demonstrated that TLE3 expression correlates with response to chemotherapy with methotrexate (see FIG. 7) and taxanes (see FIGS. 10, 12 and 13). Methotrexate and taxanes are thought to be cell cycle specific chemotherapeutics (e.g., see Goodman & Gilman's The Pharmacological Basis of Therapeutics, IX. Chemotherapy of Neoplastic Diseases Chapter 51. Antineoplastic Agents, 11th Edition, Laurence L. Brunton, editor-in-chief, John S. Lazo and Keith L. Parker, Associate Editors). Cell cycle specific chemotherapeutics exhibit their mechanism of action within a specific phase of the cell cycle in contrast to non-cell cycle specific chemotherapeutics that work equally with all phases including the resting phase (G0). Other plant alkaloids besides the taxanes have also been classified in the literature as cell cycle specific chemotherapeutics as have other antimetabolites besides methotrexate. In contrast, many alkylating agents such as cisplatin and cyclophosamide have been classified as non-cell cycle specific chemotherapeutics. Our results suggest that the predictive power of TLE3 may extend to other cell cycle specific chemotherapeutics besides methotrexate and taxanes.

In some embodiments, the inventive methods may therefore be used to select, or decide whether to administer, a cell cycle specific chemotherapeutic. In one embodiment, the inventive methods may be used to select, or decide whether to administer, an antimetabolite. In one embodiment, the inventive methods may be used to select, or decide whether to administer, a plant alkaloid. In one embodiment, the inventive methods may be used to select, or decide whether to administer, methotrexate. In another embodiment, the inventive methods may be used to select, or decide whether to administer, a taxane. In one embodiment the taxane is paclitaxel. In one embodiment the taxane is docetaxel.

In each case it will be appreciated that these chemotherapeutics may be administered alone or in combination with other chemotherapeutics as is known in the art and discussed below. It will also be appreciated that the present invention encompasses methods in which the selected chemotherapeutic is a methotrexate or taxane derivative, i.e., a compound with a structure which is derived from methotrexate or a taxane. Derivatives will typically share most of the structure of the parent compound but may include different substituents, heteroatoms, ring fusions, levels of saturation, isomerism, stereoisomerism, etc. at one or more positions within the parent compound. Without limitation, the following U.S. Patents describe the preparation of exemplary methotrexate derivatives that could be employed according to an inventive method: U.S. Pat. Nos. 6,559,149 and 4,374,987. Without limitation, the following U.S. Patents describe the preparation of exemplary taxane derivatives that could be employed according to an inventive method: U.S. Pat. Nos. 7,074,945; 7,063,977; 6,906,101; 6,649,778; 6,596,880; 6,552,205; 6,531,611; 6,482,963; 6,482,850; 6,462,208; 6,455,575; 6,441,026; 6,433,180; 6,392,063; 6,369,244; 6,339,164; 6,291,690; 6,268,381; 6,239,167; 6,218,553; 6,214,863; 6,201,140; 6,191,290; 6,187,916; 6,162,920; 6,147,234; 6,136,808; 6,114,550; 6,107,332; 6,051,600; 6,025,385; 6,011,056; 5,955,489; 5,939,567; 5,912,263; 5,908,835; 5,869,680; 5,861,515; 5,821,263; 5,763,477; 5,750,561; 5,728,687; 5,726,346; 5,726,318; 5,721,268; 5,719,177; 5,714,513; 5,714,512; 5,703,117; 5,698,582; 5,686,623; 5,677,462; 5,646,176; 5,637,723; 5,621,121; 5,616,739; 5,606,083; 5,580,899; 5,476,954; 5,403,858; 5,380,916; 5,254,703; and 5,250,722. The entire contents of each of the aforementioned patents and any other reference which is cited herein is hereby incorporated by reference.

Methotrexate acts by inhibiting the metabolism of folic acid and has been approved for the treatment of bladder cancer, breast cancer, gastric cancer, choriocarcinoma, head and neck cancer, leptomeningeal cancer, leukemia (acute meningeal, acute lymphoblastic, acute lymphocytic), lymphoma (Burkitt's, childhood, non-Hodgkin's), mycosis fungoides, primary unknown cancer and lymphatic sarcoma (Methotrexate in BC Cancer Agency Cancer Drug Manual, 2007). Methotrexate has also been shown to be useful for treating esophageal cancer, lung cancer and testicular cancer (Methotrexate in UpToDate, 2007). In certain embodiments, the inventive methods comprise a step of selecting, or deciding whether to administer, methotrexate in combination with one or more additional chemotherapeutics. For example, methotrexate is commonly administered to cancer patients as a combination called CMF which also includes cyclophosphamide and 5-fluorouracil.

Taxanes are diterpenes produced by the plants of the genus *Taxus*. Taxanes can be obtained from natural sources or produced synthetically. Taxanes include paclitaxel (TAXOL™) and docetaxel (TAXOTERE™). Taxanes work by interfering with normal microtubule growth during cell division. In certain embodiments, the inventive methods comprise a step of selecting, or deciding whether to administer, a taxane (e.g., paclitaxel or docetaxel) in combination with one or more additional chemotherapeutics. For example, taxanes are commonly administered to cancer patients in combination with cyclophosphamide and adriamycin (doxorubicin) and optionally 5-fluorouracil (i.e., with CA or CAF).

Paclitaxel has been approved for the treatment of breast cancer, Kaposi's sarcoma, lung cancer and ovarian cancer (Paclitaxel in BC Cancer Agency Cancer Drug Manual, 2007 and Mekhail and Markman, *Expert Opin. Pharmacother.* 3:755-66, 2002). Paclitaxel has also been shown to be useful in treating cervical cancer (pp. 1124-34 in AHFS 2005 Drug Information. Bethesda, Md.: American Society of Health-System Pharmacists, 2005), endometrial cancer (Paclitaxel in BC Cancer Agency Cancer Drug Manual, 2007), bladder cancer (Paclitaxel in UpToDate, 2007), head and neck cancer (Paclitaxel in UpToDate, 2007), leukemia (Paclitaxel in UpToDate, 2007) and malignant melanoma (Paclitaxel in UpToDate, 2007). Side effects of paclitaxel include hypersensitivity reactions such as flushing of the face, skin rash, or shortness of breath. Patients often receive medication to prevent hypersensitivity reactions before they take paclitaxel. Paclitaxel can also cause temporary damage to the bone marrow. Bone marrow damage can cause a person to be more susceptible to infection, anemia, and bruise or bleed easily. Other side effects may include joint or muscle pain in the arms or legs; diarrhea; nausea and vomiting; numbness, burning, or tingling in the hands or feet; and loss of hair.

Docetaxel has been approved for the treatment of breast cancer (Aapro, *Seminars in Oncology* 25(5 Suppl 12):7-11, 1998; Nabholtz et al., *Journal of Clinical Oncology* 17(5): 1413-24, 1999; Sjostrom et al., *European Journal of Cancer* 35(8):1194-201, 1999; and Burstein et al., *Journal of Clinical Oncology* 18(6):1212-9, 2000), non-small cell lung cancer (Fossella et al., *Journal of Clinical Oncology* 18(12):2354-62, 2000 and Hainsworth et al., *Cancer* 89(2):328-33, 2000) and ovarian cancer (Kaye et al., *European Journal of Cancer* 33(13):2167-70, 1997). Docetaxel has also been shown to be useful in treating esothelioma (Vorobiof et al., *Proc Am Soc Clin Oncol* 19:578a, 2000), prostate cancer (Picus et al., *Seminars in Oncology* 26(5 Suppl 17):14-8, 1999 and Petrylak et al., *Journal of Clinical Oncology* 17(3):958-67, 1999), urothelial transitional cell cancer (Dimopoulos et al., *Annals of Oncology* 10(11):1385-8, 1999 and Pectasides et al., *European Journal of Cancer* 36(1):74-9, 2000), head and neck cancer (Docetaxel in USP DI, 2000 and Couteau et al., *British Journal of Cancer* 81(3):457-62, 1999) and small cell lung cancer (Smyth et al., *European Journal of Cancer* 30A(8): 1058-60, 1994).

Our observation that improved response to chemotherapy is observed for both breast and ovarian cancer patients that are TLE3-positive suggests that the inventive methods may be useful across different cancer types. Our observation that TLE3 expression is associated with improved response to treatment with methotrexate and taxanes further suggest that the inventive methods may be applicable across cancers that respond to these chemotherapeutics. As discussed above, this includes without limitation breast cancer, ovarian cancer, lung cancer, bladder cancer, gastric cancer, head and neck cancer, and leukemia.

In one embodiment, the inventive methods may be used with a cancer patient that has breast cancer. In one embodiment, the inventive methods may be used with a cancer patient that has ovarian cancer. In one embodiment, the inventive methods may be used with a cancer patient that has lung cancer. In one embodiment, the inventive methods may be used with a cancer patient that has bladder cancer. In one embodiment, the inventive methods may be used with a cancer patient that has gastric cancer. In one embodiment, the inventive methods may be used with a cancer patient that has head and neck cancer. In one embodiment, the inventive methods may be used with a cancer patient that has leukemia.

As demonstrated in the Examples, in one embodiment, the correlation between TLE3 expression and response to chemotherapy was observed with breast cancer patients that are triple negative for the ER (estrogen receptor, Entrez GeneID 2099), PR (progesterone receptor, Entrez GeneID 5241) and HER-2 markers (v-erb-b2 erythroblastic leukemia viral oncogene homolog 2, Entrez GeneID 2064). In certain embodiments, the inventive methods may therefore be used with breast cancer patients that belong to this class.

As demonstrated in the Examples, the correlation between TLE3 expression and response to chemotherapy was found to also exist when treatment was administered in a neoadjuvant setting. Thus, in certain embodiments, the inventive methods may be used with patients receiving chemotherapy in a neoadjuvant setting. In other embodiments, the chemotherapy may be administered in an adjuvant setting.

As demonstrated in the Examples, the correlation between TLE3 expression and response to chemotherapy was also found to be independent of stage. Thus, in certain embodiments, the inventive methods may be used with patients with a stage II+ (i.e., stage II or greater) cancer. In certain embodiments, the inventive methods may be used with patients with a stage IIb+ or a stage III+ cancer.

Detecting TLE3 Expression

As mentioned above, expression of TLE3 can be determined using any known method. In one embodiment, TLE3 expression may be determined by detecting TLE3 polypeptide markers using interaction partners (e.g., antibodies). In another embodiment, TLE3 expression may be determined by detecting TLE3 polynucleotide markers using primers.

Detecting TLE3 Polypeptide Markers

TLE3 polypeptide markers may be detected using any interaction partner that binds a TLE3 polypeptide marker (which could be a TLE3 protein or an antigenic fragment thereof). Thus, any entity that binds detectably to the TLE3 marker may be utilized as an interaction partner in accordance with the present invention, so long as it binds the marker with an appropriate combination of affinity and specificity.

Particularly preferred interaction partners are antibodies, or fragments (e.g., F(ab) fragments, F(ab')$_2$ fragments, Fv fragments, or sFv fragments, etc.; see, for example, Inbar et al., *Proc. Nat. Acad. Sci. USA* 69:2659, 1972; Hochman et al., *Biochem.* 15:2706, 1976; and Ehrlich et al., *Biochem.* 19:4091, 1980; Huston et al., *Proc. Nat. Acad. Sci. USA* 85:5879, 1998; U.S. Pat. Nos. 5,091,513 and 5,132,405 to Huston et al.; and U.S. Pat. No. 4,946,778 to Ladner et al., each of which is incorporated herein by reference). In certain embodiments, interaction partners may be selected from libraries of mutant antibodies (or fragments thereof). For example, collections of antibodies that each include different point mutations may be screened for their association with a marker of interest. Yet further, chimeric antibodies may be used as interaction partners, e.g., "humanized" or "veneered" antibodies as described in greater detail below.

When antibodies are used as interaction partners, these may be prepared by any of a variety of techniques known to those of ordinary skill in the art (e.g., see Harlow and Lane, *Antibodies: A Laboratory Manual*, Cold Spring Harbor Laboratory, 1988, see also the Examples). For example, antibodies can be produced by cell culture techniques, including the generation of monoclonal antibodies, or via transfection of antibody genes into suitable bacterial or mammalian cell hosts, in order to allow for the production of recombinant antibodies. In one technique, an "immunogen" comprising an antigenic portion of a marker of interest (or the marker itself) is initially injected into any of a wide variety of mammals (e.g., mice, rats, rabbits, sheep or goats). In this step, a marker (or an antigenic portion thereof) may serve as the immunogen without modification. Alternatively, particularly for relatively short markers, a superior immune response may be elicited if the marker is joined to a carrier protein, such as bovine serum albumin or keyhole limpet hemocyanin (KLH). The immunogen is injected into the animal host, preferably according to a predetermined schedule incorporating one or more booster immunizations and the animals are bled periodically. Polyclonal antibodies specific for the marker may then be purified from such antisera by, for example, affinity chromatography using the marker (or an antigenic portion thereof) coupled to a suitable solid support. An exemplary method is described in the Examples.

If desired for diagnostic or therapeutic purposes, monoclonal antibodies specific for TLE3 may be prepared, for example, using the technique of Kohler and Milstein, *Eur. J. Immunol.* 6:511, 1976 and improvements thereto. Briefly, these methods involve the preparation of immortal cell lines capable of producing antibodies having the desired specificity (i.e., reactivity with the marker of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the marker. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation and extraction. TLE3 may be used in the purification process in, for example, an affinity chromatography step.

It is to be understood that the present invention is not limited to using antibodies or antibody fragments as interaction partners. In particular, the present invention also encompasses the use of synthetic interaction partners that mimic the functions of antibodies. Several approaches to designing and/or identifying antibody mimics have been proposed and demonstrated (e.g., see the reviews by Hsieh-Wilson et al., *Acc. Chem. Res.* 29:164, 2000 and Peczuh and Hamilton, *Chem. Rev.* 100:2479, 2000). For example, small molecules that bind protein surfaces in a fashion similar to that of natural proteins have been identified by screening synthetic libraries of small molecules or natural product isolates (e.g., see Gallop et al., *J. Med. Chem.* 37:1233, 1994; Gordon et al., *J. Med. Chem.* 37:1385, 1994; DeWitt et al., *Proc. Natl. Acad. Sci. U.S.A.* 90:6909, 1993; Bunin et al., *Proc. Natl. Acad. Sci. U.S.A.* 91:4708, 1994; Virgilio and Ellman, *J. Am. Chem. Soc.* 116:11580, 1994; Wang et al., *J. Med. Chem.* 38:2995, 1995; and Kick and Ellman, *J. Med. Chem.* 38:1427, 1995). Similarly, combinatorial approaches have been successfully applied to screen libraries of peptides and proteins for their ability to bind a range of proteins (e.g., see Cull et al., *Proc. Natl. Acad. Sci. U.S.A.* 89:1865, 1992; Mattheakis et al., *Proc. Natl. Acad. Sci. U.S.A.* 91:9022, 1994; Scott and Smith, *Science* 249:386, 1990; Devlin et al., *Science* 249:404, 1990; Corey et al., *Gene* 128:129, 1993; Bray et al., *Tetrahedron Lett.* 31:5811, 1990; Fodor et al., *Science* 251:767, 1991; Houghten et al., *Nature* 354:84, 1991; Lam et al., *Nature* 354:82, 1991; Blake and Litzi-Davis, *Bioconjugate Chem.* 3:510, 1992; Needels et al., *Proc. Natl. Acad. Sci. U.S.A.* 90:10700, 1993; and Ohlmeyer et al., *Proc. Natl. Acad. Sci. U.S.A.* 90:10922, 1993). Similar approaches have also been used to study carbohydrate-protein interactions (e.g., see Oldenburg et al., *Proc. Natl. Acad. Sci. U.S.A.* 89:5393, 1992) and polynucleotide-protein interactions (e.g., see Ellington and Szostak, *Nature* 346:818, 1990 and Tuerk and Gold, *Science* 249:505, 1990). These approaches have also been extended to study interactions between proteins and unnatural biopolymers such as oligocarbamates, oligoureas, oligosulfones, etc. (e.g., see Zuckermann et al., *J. Am. Chem. Soc.* 114:10646, 1992; Simon et al., *Proc. Natl. Acad. Sci. U.S.A.* 89:9367, 1992; Zuckermann et al., *J. Med. Chem.* 37:2678, 1994; Burgess et al., *Angew. Chem.*, Int. Ed. Engl. 34:907, 1995; and Cho et al., *Science* 261:1303, 1993). Yet further, alternative protein scaffolds that are loosely based around the basic fold of antibody molecules have been suggested and may be used in the preparation of inventive interaction partners (e.g., see Ku and Schultz *Proc. Natl. Acad. Sci. U.S.A.* 92:6552, 1995). Antibody mimics comprising a scaffold of a small molecule such as 3-aminomethylbenzoic acid and a substituent consisting of a single peptide loop have also been constructed. The peptide loop performs the binding function in these mimics (e.g., see Smythe et al., *J. Am. Chem. Soc.* 116:2725, 1994). A synthetic antibody mimic comprising multiple peptide loops built around a calixarene unit has also been described (e.g., see U.S. Pat. No. 5,770,380 to Hamilton et al.).

Any available strategy or system may be utilized to detect association between an interaction partner and the TLE3 marker. In certain embodiments, association can be detected by adding a detectable label to the interaction partner. In other embodiments, association can be detected by using a labeled secondary interaction partner that binds specifically with the primary interaction partner, e.g., as is well known in the art of antigen/antibody detection. The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Examples of indirectly detectable include chemiluminescent labels, e.g., enzymes that are capable of converting a substrate to a chromogenic product such as alkaline phosphatase, horseradish peroxidase and the like.

Once a labeled interaction partner has bound the TLE3 marker, the complex may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In general, association between an interaction partner and the TLE3 marker may be assayed by contacting the interaction partner with a cancer sample that includes the marker. Depending upon the nature of the sample, appropriate methods include, but are not limited to, immunohistochemistry (IHC), radioimmunoassay, ELISA, immunoblotting and fluorescence activates cell sorting (FACS). In the case where the protein is to be detected in a tissue sample, e.g., a biopsy sample, IHC is a particularly appropriate detection method. Techniques for obtaining tissue and cell samples and performing IHC and FACS are well known in the art.

Where large numbers of samples are to be handled (e.g., when simultaneously analyzing several samples from the same patient or samples from different patients), it may be desirable to utilize arrayed and/or automated formats. In certain embodiments, tissue arrays as described in the Examples may be used. Tissue arrays may be constructed according to a variety of techniques. According to one procedure, a commercially-available mechanical device (e.g., the manual tissue arrayer MTA1 from Beecher Instruments of Sun Prairie, Wis.) is used to remove an 0.6-micron-diameter, full thickness "core" from a paraffin block (the donor block) prepared from each patient, and to insert the core into a separate paraffin block (the recipient block) in a designated location on a grid. In preferred embodiments, cores from as many as about 400 patients (or multiple cores from the same patient) can be inserted into a single recipient block; preferably, core-to-core spacing is approximately 1 mm. The resulting tissue array may be processed into thin sections for staining with interaction partners according to standard methods applicable to paraffin embedded material.

Whatever the format, and whatever the detection strategy, identification of a discriminating titer can simplify binding studies to assess the desirability of using an interaction partner. In such studies, the interaction partner is contacted with a plurality of different samples that preferably have at least one common trait (e.g., tissue of origin), and often have multiple common traits (e.g., tissue of origin, stage, microscopic characteristics, etc.). In some cases, it will be desirable to select a group of samples with at least one common trait and at least one different trait, so that a titer is determined that distinguishes the different trait. In other cases, it will be desirable to select a group of samples with no detectable different traits, so that a titer is determined that distinguishes among previously indistinguishable samples. Those of ordinary skill in the art will understand, however, that the present invention often will allow both of these goals to be accomplished even in studies of sample collections with varying degrees of similarity and difference.

As discussed above and in the Examples, the inventors have applied these techniques to samples from breast and ovarian cancer patients. The invention also encompasses the recognition that markers that are secreted from the cells in which they are produced may be present in serum, enabling their detection through a blood test rather than requiring a biopsy specimen. An interaction partner that binds to such markers represents a particularly preferred embodiment of the invention.

In general, the results of such an assay can be presented in any of a variety of formats. The results can be presented in a qualitative fashion. For example, the test report may indicate only whether or not the TLE3 marker was detected, perhaps also with an indication of the limits of detection. Additionally the test report may indicate the subcellular location of binding, e.g., nuclear versus cytoplasmic and/or the relative levels of binding in these different subcellular locations. The results may be presented in a semi-quantitative fashion. For example, various ranges may be defined and the ranges may be assigned a score (e.g., 0 to 5) that provides a certain degree of quantitative information. Such a score may reflect various factors, e.g., the number of cells in which the marker is detected, the intensity of the signal (which may indicate the level of expression of the marker), etc. The results may be presented in a quantitative fashion, e.g., as a percentage of cells in which the marker is detected, as a concentration, etc. As will be appreciated by one of ordinary skill in the art, the type of output provided by a test will vary depending upon the technical limitations of the test and the biological significance associated with detection of the marker. For example, in certain circumstances a purely qualitative output (e.g., whether or not the marker is detected at a certain detection level)

provides significant information. In other cases a more quantitative output (e.g., a ratio of the level of expression of the marker in two samples) is necessary.

Detecting TLE3 Polynucleotide Markers

Although in many cases detection of polypeptide markers using interaction partners such as antibodies may represent the most convenient means of determining whether TLE3 is expressed in a particular sample, the inventive methods also encompass the use of primers for the detection of polynucleotide markers. A variety of methods for detecting the presence of a particular polynucleotide marker are known in the art and may be used in the inventive methods. In general, these methods rely on hybridization between one or more primers and the polynucleotide marker.

Any available strategy or system may be utilized to detect hybridization between primers and the TLE3 polynucleotides (which could be a TLE3 mRNA, a cDNA produced by RT-PCR from mRNA, RNA produced from such cDNA, etc.). In certain embodiments, hybridization can be detected by simply adding a detectable label to the primer. In other embodiments, hybridization can be detected by using a labeled secondary primer that hybridizes specifically with the primary primer (e.g., a region of the primary primer that does not hybridize with the TLE3 marker). In yet other embodiments it may be advantageous to amplify the TLE3 marker within the cancer sample by PCR using a set of primers designed to amplify a region of the TLE3 gene. The resulting product can then be detected, e.g., using a labeled secondary primer that hybridizes with the amplified product. Those skilled in the art will appreciate variations on these embodiments.

Considerations for primer design are well known in the art and are described, for example, in Newton, et al. (eds.) PCR: *Essential data Series*, John Wiley & Sons; *PCR Primer: A Laboratory Manual*, Cold Spring Harbor Laboratory Press, Cold Spring Harbor, N.Y., 1995; White, et al. (eds.) *PCR Protocols: Current methods and Applications*, Methods in Molecular Biology, The Humana Press, Totowa, N.J., 1993. In addition, a variety of computer programs known in the art may be used to select appropriate primers.

In general, a detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Examples of indirectly detectable include chemiluminescent labels, e.g., enzymes that are capable of converting a substrate to a chromogenic product such as alkaline phosphatase, horseradish peroxidase and the like.

Once a labeled primer has hybridized with the TLE3 marker, the complex may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In general, hybridization between a primer and the TLE3 marker may be assayed by contacting the primer with a cancer sample that includes the marker. Depending upon the nature of the cancer sample, appropriate methods include, but are not limited to, microarray analysis, in situ hybridization, Northern blot, and various nucleic acid amplification techniques such as PCR, RT-PCR, quantitative PCR, the ligase chain reaction, etc.

Identification of Novel Therapies

The predictive power of TLE3 is useful according to the present invention not only to classify cancers with respect to their likely responsiveness to known therapies, but also to identify potential new therapies or therapeutic agents that could be useful in the treatment of cancer.

Indeed, TLE3 represents an attractive candidate for identification of new therapeutic agents (e.g., via screens to detect compounds or entities that bind or hybridize to the marker, preferably with at least a specified affinity and/or specificity, and/or via screens to detect compounds or entities that modulate (i.e., increase or decrease) expression, localization, modification, or activity of the marker. Thus, in one embodiment the present invention provides methods comprising steps of contacting a test compound with a cell expressing the TLE3 marker (e.g., individual engineered cells or in the context of a tissue, etc.); and determining whether the test compound modulates the expression, localization, modification, or activity of the TLE3 marker. In many instances, interaction partners or primers (e.g., antisense or RNAi primers) themselves may prove to be useful therapeutics.

Thus the present invention provides interaction partners and primers that are themselves useful therapeutic agents. For example, binding by an antibody raised against TLE3 to cancerous cells might inhibit growth of those cells. Alternatively or additionally, interaction partners defined or prepared according to the present invention could be used to deliver a therapeutic agent to a cancer cell. In particular, interaction partners (e.g., an antibody raised against TLE3) may be coupled to one or more therapeutic agents. Suitable agents in this regard include radionuclides and drugs. Preferred radionuclides include $^{90}Y$, $^{123}I$, $^{125}I$, $^{131}I$, $^{186}Re$, $^{188}Re$, $^{211}At$ and $^{212}Bi$. Preferred drugs include chlorambucil, ifosphamide, mechlorethamine, cyclophosphamide, carboplatin, cisplatin, procarbazine, decarbazine, carmustine, cytarabine, hydroxyurea, mercaptopurine, methotrexate, paclitaxel, docetaxel, thioguanine, 5-fluorouracil, actinomycin D, bleomycin, daunorubicin, doxorubicin, etoposide, vinblastine, vincristine, L-asparginase, adrenocorticosteroids, canciclovir triphosphate, adenine arabinonucleoside triphosphate, 5-aziridinyl-4-hydroxylamino-2-nitrobenzamide, acrolein, phosphoramide mustard, 6-methylpurine, etoposide, benzoic acid mustard, cyanide and nitrogen mustard.

According to such embodiments, the therapeutic agent may be coupled with an interaction partner by direct or indirect covalent or non-covalent interactions. A direct interaction between a therapeutic agent and an interaction partner is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Indirect interactions might involve a linker group that is itself non-covalently bound to both the therapeutic agent and the interaction partner. A linker group can function as a spacer to distance an interaction partner from an agent in order to avoid interference with association capabilities. A linker group can also serve to increase the chemical reactivity of a substituent on an agent or an interaction partner and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al. It will further be appreciated that a therapeutic agent and an interaction partner may be coupled via non-covalent interactions, e.g., ligand/receptor type interactions. Any ligand/receptor pair with a sufficient stability and specificity to operate in the context of the invention may be employed to couple a therapeutic agent and an interaction partner. To give but an example, a therapeutic agent may be covalently linked with biotin and an interaction partner with avidin. The strong non-covalent binding of biotin to avidin would then allow for coupling of the therapeutic agent and the interaction partner. Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and maltose binding protein (MBP) and further those described in Kessler pp. 105-152 of *Advances in Mutagenesis*" Ed. by Kessler, Springer-Verlag, 1990; "*Affinity Chromatography: Methods and Protocols (Methods in Molecular Biology)*" Ed. by Pascal Baillon, Humana Press, 2000; and "*Immobilized Affinity Ligand Techniques*" by Hermanson et al., *Academic Press*, 1992.

Where a therapeutic agent is more potent when free from the interaction partner, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710 to Spitler), by irradiation of a photolabile bond (e.g., U.S. Pat. No. 4,625,014 to Senter et al.), by hydrolysis of derivatized amino acid side chains (e.g., U.S. Pat. No. 4,638,045 to Kohn et al.), by serum complement-mediated hydrolysis (e.g., U.S. Pat. No. 4,671,958 to Rodwell et al.) and by acid-catalyzed hydrolysis (e.g., U.S. Pat. No. 4,569,789 to Blattler et al.).

In certain embodiments, it may be desirable to couple more than one therapeutic agent to an interaction partner. In one embodiment, multiple molecules of an agent are coupled to one interaction partner molecule. In another embodiment, more than one type of therapeutic agent may be coupled to one interaction partner molecule. Regardless of the particular embodiment, preparations with more than one agent may be prepared in a variety of ways. For example, more than one agent may be coupled directly to an interaction partner molecule, or linkers that provide multiple sites for attachment can be used.

Alternatively, a carrier can be used. A carrier may bear the agents in a variety of ways, including covalent bonding either directly or via a linker group. Suitable carriers include proteins such as albumins (e.g., U.S. Pat. No. 4,507,234 to Kato et al.), peptides, and polysaccharides such as aminodextran (e.g., U.S. Pat. No. 4,699,784 to Shih et al.). A carrier may also bear an agent by non-covalent bonding or by encapsulation, such as within a liposome vesicle (e.g., U.S. Pat. Nos. 4,429,008 to Martin et al. and 4,873,088 to Mayhew et al.). Carriers specific for radionuclide agents include radiohalogenated small molecules and chelating compounds. For example, U.S. Pat. No. 4,735,792 to Srivastava discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562 to Davison et al. discloses representative chelating compounds and their synthesis.

When interaction partners are themselves therapeutics, it will be understood that, in many cases, any interaction partner that binds the same marker may be so used.

In one preferred embodiment of the invention, the therapeutic agents (whether interaction partners or otherwise) are antibodies, e.g., an antibody against the TLE3 marker. As is well known in the art, when using an antibody or fragment thereof for therapeutic purposes it may prove advantageous to use a "humanized" or "veneered" version of an antibody of interest to reduce any potential immunogenic reaction. In general, "humanized" or "veneered" antibody molecules and fragments thereof minimize unwanted immunological responses toward antihuman antibody molecules which can limit the duration and effectiveness of therapeutic applications of those moieties in human recipients.

A number of "humanized" antibody molecules comprising an antigen binding portion derived from a non-human immunoglobulin have been described in the art, including chimeric antibodies having rodent variable regions and their associated complementarity-determining regions (CDRs) fused to human constant domains (e.g., see Winter et al., *Nature* 349: 293, 1991; Lobuglio et al., *Proc. Nat. Acad. Sci. USA* 86:4220, 1989; Shaw et al., *J. Immunol.* 138:4534, 1987; and Brown et al., *Cancer Res.* 47:3577, 1987), rodent CDRs grafted into a human supporting framework region (FR) prior to fusion with an appropriate human antibody constant domain (e.g., see Riechmann et al., *Nature* 332:323, 1988; Verhoeyen et al., *Science* 239:1534, 1988; and Jones et al. *Nature* 321:522, 1986) and rodent CDRs supported by recombinantly veneered rodent FRs (e.g., see European Patent Publication No. 519,596, published Dec. 23, 1992). It is to be understood that the invention also encompasses "fully human" antibodies produced using the XenoMouse™ technology (AbGenix Corp., Fremont, Calif.) according to the techniques described in U.S. Pat. No. 6,075,181.

Yet further, so-called "veneered" antibodies may be used that include "veneered FRs". The process of veneering involves selectively replacing FR residues from, e.g., a murine heavy or light chain variable region, with human FR residues in order to provide a xenogeneic molecule comprising an antigen binding portion which retains substantially all of the native FR protein folding structure. Veneering techniques are based on the understanding that the antigen binding characteristics of an antigen binding portion are determined primarily by the structure and relative disposition of the heavy and light chain CDR sets within the antigen-association surface (e.g., see Davies et al., *Ann. Rev. Biochem.* 59:439, 1990). Thus, antigen association specificity can be preserved in a humanized antibody only wherein the CDR structures, their interaction with each other and their interaction with the rest of the variable region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

Preferably, interaction partners suitable for use as therapeutics (or therapeutic agent carriers) exhibit high specificity for the target marker (e.g., TLE3) and low background binding to other markers. In certain embodiments, monoclonal antibodies are preferred for therapeutic purposes.

Pharmaceutical Compositions

As mentioned above, the present invention provides new therapies and methods for identifying these. In certain embodiments, an interaction partner or primer may be a useful therapeutic agent. Alternatively or additionally, interaction partners defined or prepared according to the present invention bind to markers (e.g., TLE3) that serve as targets for therapeutic agents. Also, inventive interaction partners may be used to deliver a therapeutic agent to a cancer cell. For example, interaction partners provided in accordance with the present invention may be coupled to one or more therapeutic agents.

The invention includes pharmaceutical compositions comprising these inventive therapeutic agents. In general, a pharmaceutical composition will include a therapeutic agent in addition to one or more inactive agents such as a sterile, biocompatible carrier including, but not limited to, sterile water, saline, buffered saline, or dextrose solution. The pharmaceutical compositions may be administered either alone or in combination with other therapeutic agents including other chemotherapeutic agents, hormones, vaccines and/or radiation therapy. By "in combination with", here and elsewhere in the specification, it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the inventive pharmaceutical compositions in combination with agents that may improve their bioavailability, reduce or modify their metabolism, inhibit their excretion, or modify their distribution within the body. Although the pharmaceutical compositions of the present invention can be used for treatment of any subject (e.g., any animal) in need thereof, they are most preferably used in the treatment of humans.

The pharmaceutical compositions of this invention can be administered to humans and other animals by a variety of routes including oral, intravenous, intramuscular, intra-arterial, subcutaneous, intraventricular, transdermal, rectal, intravaginal, intraperitoneal, topical (as by powders, ointments, or drops), bucal, or as an oral or nasal spray or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc. At present the intravenous route is most commonly used to deliver therapeutic antibodies. However, the invention encompasses the delivery of the inventive pharmaceutical composition by any appropriate route taking into consideration likely advances in the sciences of drug delivery.

General considerations in the formulation and manufacture of pharmaceutical agents may be found, for example, in *Remington's Pharmaceutical Sciences*, 19$^{th}$ ed., Mack Publishing Co., Easton, Pa., 1995.

EXEMPLIFICATION

Example 1

Raising Antibodies

This example describes a method that was employed to generate the TLE3 antibodies used in these Examples. Similar methods may be used to generate an antibody that binds to any marker of interest (e.g., to proteins that are or are derived from other markers listed in Appendix A). In some cases, antibodies may be obtained from commercial sources (e.g., Chemicon, Dako, Oncogene Research Products, NeoMarkers, etc.) or other publicly available sources (e.g., Imperial Cancer Research Technology, etc.).

Materials and Solutions

Anisole (Cat. No. A4405, Sigma, St. Louis, Mo.)

2,2'-azino-di-(3-ethyl-benzthiazoline-sulfonic acid) (ABTS) (Cat. No. A6499, Molecular Probes, Eugene, Oreg.)

Activated maleimide Keyhole Limpet Hemocyanin (Cat. No. 77106, Pierce, Rockford, Ill.)

Keyhole Limpet Hemocyanin (Cat. No. 77600, Pierce, Rockford, Ill.)

Phosphoric Acid ($H_3PO_4$) (Cat. No. P6560, Sigma)

Glacial Acetic Acid (Cat No. BP1185-500, Fisher)

EDC (EDAC) (Cat No. 341006, Calbiochem)

25% Glutaraldehyde (Cat No. G-5882, Sigma)

Glycine (Cat No. G-8898, Sigma)

Biotin (Cat. No. B2643, Sigma)

Boric acid (Cat. No. B0252, Sigma)

Sepharose 4B (Cat. No. 17-0120-01, LKB/Pharmacia, Uppsala, Sweden)

Bovine Serum Albumin (LP) (Cat. No. 100 350, Boehringer Mannheim, Indianapolis, Ind.)

Cyanogen bromide (Cat. No. C6388, Sigma)

Dialysis tubing Spectra/Por Membrane MWCO: 6-8,000 (Cat. No. 132 665, Spectrum Industries, Laguna Hills, Calif.)

Dimethyl formamide (DMF) (Cat. No. 22705-6, Aldrich, Milwaukee, Wis.)

DIC (Cat. No. BP 592-500, Fisher)

Ethanedithiol (Cat. No. 39, 802-0, Aldrich)

Ether (Cat. No. TX 1275-3, EM Sciences)

Ethylenediaminetetraacetic acid (EDTA) (Cat. No. BP 120-1, Fisher, Springfield, N.J.)

1-ethyl-3-(3' dimethylaminopropyl)-carbodiimide, HCL (EDC) (Cat. no. 341-006, Calbiochem, San Diego, Calif.)

Freund's Adjuvant, complete (Cat. No. M-0638-50B, Lee Laboratories, Grayson, Ga.)

Freund's Adjuvant, incomplete (Cat. No. M-0639-50B, Lee Laboratories)

Fritted chromatography columns (Column part No. 12131011; Frit Part No. 12131029, Varian Sample Preparation Products, Harbor City, Calif.)

Gelatin from Bovine Skin (Cat. No. G9382, Sigma)

Goat anti-rabbit IgG, biotinylated (Cat. No. A 0418, Sigma)

HOBt (Cat. No. 01-62-0008, Calbiochem)

Horseradish peroxidase (HRP) (Cat. No. 814 393, Boehringer Mannheim)

HRP-Streptavidin (Cat. No. S 5512, Sigma)

Hydrochloric Acid (Cat. No. 71445-500, Fisher)

Hydrogen Peroxide 30% w/w (Cat. No. H1009, Sigma)

Methanol (Cat. No. A412-20, Fisher)

Microtiter plates, 96 well (Cat. No. 2595, Corning-Costar, Pleasanton, Calif.)

N—Fmoc protected amino acids from Calbiochem. See '97-'98 Catalog pp. 1-45.

N—Fmoc protected amino acids attached to Wang Resin from Calbiochem. See '97-'98 Catalog pp. 161-164.

NMP (Cat. No. CAS 872-50-4, Burdick and Jackson, Muskegon, Mich.)

Peptide (Synthesized by Research Genetics. Details given below)
Piperidine (Cat. No. 80640, Fluka, available through Sigma)
Sodium Bicarbonate (Cat. No. BP328-1, Fisher)
Sodium Borate (Cat. No. B9876, Sigma)
Sodium Carbonate (Cat. No. BP357-1, Fisher)
Sodium Chloride (Cat. No. BP 358-10, Fisher)
Sodium Hydroxide (Cat. No. SS 255-1, Fisher)
Streptavidin (Cat. No. 1 520, Boehringer Mannheim)
Thioanisole (Cat. No. T-2765, Sigma)
Trifluoroacetic acid (Cat. No. TX 1275-3, EM Sciences)
Tween-20 (Cat. No. BP 337-500, Fisher)
Wetbox (Rectangular Servin' Saver™ Part No. 3862, Rubbermaid, Wooster, Ohio)
BBS—Borate Buffered Saline with EDTA dissolved in distilled water (pH 8.2 to 8.4 with HCl or NaOH), 25 mM Sodium borate (Borax), 100 mM Boric Acid, 75 mM NaCl and 5 mM EDTA.
0.1 N HCl in saline as follows: concentrated HCl (8.3 ml/0.917 liter distilled water) and 0.154 M NaCl
Glycine (pH 2.0 and pH 3.0) dissolved in distilled water and adjusted to the desired pH, 0.1 M glycine and 0.154 M NaCl.
5× Borate 1× Sodium Chloride dissolved in distilled water, 0.11 M NaCl, 60 mM Sodium Borate and 250 mM Boric Acid.
Substrate Buffer in distilled water adjusted to pH 4.0 with sodium hydroxide, 50 to 100 mM Citric Acid.
AA solution: HOBt is dissolved in NMP (8.8 grams HOBt to 1 liter NMP). Fmoc-N-a-amino at a concentration at 0.53 M.
DIC solution: 1 part DIC to 3 parts NMP.
Deprotecting solution: 1 part Piperidine to 3 parts DMF.
Reagent R: 2 parts anisole, 3 parts ethanedithiol, 5 parts thioanisole and 90 parts trifluoroacetic acid.

Equipment
MRX Plate Reader (Dynatech, Chantilly, Va.)
Hamilton Eclipse (Hamilton Instruments, Reno, Nev.)
Beckman TJ-6 Centrifuge (Model No. TJ-6, Beckman Instruments, Fullerton, Calif.)
Chart Recorder (Recorder 1 Part No. 18-1001-40, Pharmacia LKB Biotechnology)
UV Monitor (Uvicord SII Part No. 18-1004-50, Pharmacia LKB Biotechnology)
Amicon Stirred Cell Concentrator (Model 8400, Amicon, Beverly, Mass.)
30 kD MW cut-off filter (Cat. No. YM-30 Membranes Cat. No. 13742, Amicon)
Multi-channel Automated Pipettor (Cat. No. 4880, Corning Costar, Cambridge, Mass.)
pH Meter Corning 240 (Corning Science Products, Corning Glassworks, Corning, N.Y.)
ACT396 peptide synthesizer (Advanced ChemTech, Louisville, Ky.)
Vacuum dryer (Box from Labconco, Kansas City, Mo. and Pump from Alcatel, Laurel, Md.).
Lyophilizer (Unitop 600sl in tandem with Freezemobile 12, both from Virtis, Gardiner, N.Y.)

Peptide Selection

Peptide or peptides against which antibodies would be raised were selected from within the protein sequence of interest using a program that uses the Hopp/Woods method (described in Hopp and Woods, *Mol. Immunol.* 20:483, 1983 and Hopp and Woods, *Proc. Nat. Acad. Sci. U.S.A.* 78:3824, 1981). The program uses a scanning window that identifies peptide sequences of 15-20 amino acids containing several putative antigenic epitopes as predicted by low solvent accessibility. This is in contrast to most implementations of the Hopp/Woods method, which identify single short (~6 amino acids) presumptive antigenic epitopes. Occasionally the predicted solvent accessibility was further assessed by PHD prediction of loop structures (described in Rost and Sander, *Proteins* 20:216, 1994). Preferred peptide sequences display minimal similarity with additional known human proteins. Similarity was determined by performing BLASTP alignments, using a wordsize of 2 (described in Altschul et al., *J. Mol. Biol.* 215:403, 1990). All alignments given an EXPECT value less than 1000 were examined and alignments with similarities of greater than 60% or more than four residues in an exact contiguous non-gapped alignment forced those peptides to be rejected. When it was desired to target regions of proteins exposed outside the cell membrane, extracellular regions of the protein of interest were determined from the literature or as defined by predicted transmembrane domains using a hidden Markov model (described in Krogh et al., *J. Mol. Biol.* 305:567, 2001). When the peptide sequence was in an extracellular domain, peptides were rejected if they contained N-linked glycosylation sites. As shown in Appendix A, for the preparation of TLE3 antibodies a single peptide was used having the amino acid sequence KNHHELDHRERES-SAN (SEQ ID NO. 383). Appendix A provides one to three peptide sequences that can be used in preparing antibodies against other markers.

Peptide Synthesis

The sequence of the desired peptide was provided to the peptide synthesizer. The C-terminal residue was determined and the appropriate Wang Resin was attached to the reaction vessel. The peptide or peptides were synthesized C-terminus to N-terminus by adding one amino acid at a time using a synthesis cycle. Which amino acid is added was controlled by the peptide synthesizer, which looks to the sequence of the peptide that was entered into its database. The synthesis steps were performed as follows:

Step 1—Resin Swelling: Added 2 ml DMF, incubated 30 minutes, drained DMF.

Step 2—Synthesis cycle (repeated over the length of the peptide)

2a—Deprotection: 1 ml deprotecting solution was added to the reaction vessel and incubated for 20 minutes.

2b—Wash Cycle

2c—Coupling: 750 ml of amino acid solution (changed as the sequence listed in the peptide synthesizer dictated) and 250 ml of DIC solution were added to the reaction vessel. The reaction vessel was incubated for thirty minutes and washed once. The coupling step was repeated once.

2d—Wash Cycle

Step 3 Final Deprotection: Steps 2a and 2b were performed one last time.

Resins were deswelled in methanol (rinsed twice in 5 ml methanol, incubated 5 minutes in 5 ml methanol, rinsed in 5 ml methanol) and then vacuum dried.

Peptide was removed from the resin by incubating 2 hours in reagent R and then precipitated into ether. Peptide was washed in ether and then vacuum dried. Peptide was resolubilized in diH$_2$O, frozen and lyophilized overnight.

Conjugation of Peptide with Keyhole Limpet Hemocyanin

Peptide (6 mg) was conjugated with Keyhole Limpet Hemocyanin (KLH). If the selected peptide includes at least one cysteine, three aliquots (2 mg) can be dissolved in PBS (2 ml) and coupled to KLH via glutaraldehyde, EDC or maleimide activated KLH (2 mg) in 2 ml of PBS for a total volume of 4 ml. When the peptide lacks cysteine (as in the TLE3 peptide), two aliquots (3 mg) can be coupled via glutaraldehyde and EDC methods.

Maleimide coupling can be accomplished by mixing 2 mg of peptide with 2 mg of maleimide-activated KLH dissolved in PBS (4 ml) and incubating 4 hr.

EDC coupling can be accomplished by mixing 2 mg of peptide, 2 mg unmodified KLH, and 20 mg of EDC in 4 ml PBS (lowered to pH 5 by the addition of phosphoric acid), and incubating for 4 hours. The reaction is then stopped by the slow addition of 1.33 ml acetic acid (pH 4.2). When using EDC to couple 3 mg of peptide, the amounts listed above are increased by a factor of 1.5.

Glutaraldehyde coupling occurs when 2 mg of peptide are mixed with 2 mg of KLH in 0.9 ml of PBS. 0.9 ml of 0.2% glutaraldehyde in PBS is added and mixed for one hour. 0.46 ml of 1 M glycine in PBS is added and mixed for one hour. When using glutaraldehyde to couple 3 mg of peptide, the above amounts are increased by a factor of 1.5.

The conjugated aliquots were subsequently repooled, mixed for two hours, dialyzed in 1 liter PBS and lyophilized.

Immunization of Rabbits

Two New Zealand White Rabbits were injected with 250 µg (total) KLH conjugated peptide in an equal volume of complete Freund's adjuvant and saline in a total volume of 1 ml. 100 µg KLH conjugated peptide in an equal volume of incomplete Freund's Adjuvant and saline were then injected into three to four subcutaneous dorsal sites for a total volume of 1 ml two, six, eight and twelve weeks after the first immunization. The immunization schedule was as follows:

| Day 0  | Pre-immune bleed, primary immunization |
|--------|----------------------------------------|
| Day 15 | 1st boost                              |
| Day 27 | 1st bleed                              |
| Day 44 | 2nd boost                              |
| Day 57 | 2nd bleed and 3rd boost                |
| Day 69 | 3rd bleed                              |
| Day 84 | 4th boost                              |
| Day 98 | 4th bleed                              |

Collection of Rabbit Serum

The rabbits were bled (30 to 50 ml) from the auricular artery. The blood was allowed to clot at room temperature for 15 minutes and the serum was separated from the clot using an IEC DPR-6000 centrifuge at 5000 g. Cell-free serum was decanted gently into a clean test tube and stored at −20° C. for affinity purification.

Determination of Antibody Titer

All solutions with the exception of wash solution were added by the Hamilton Eclipse, a liquid handling dispenser. The antibody titer was determined in the rabbits using an ELISA assay with peptide on the solid phase. Flexible high binding ELISA plates were passively coated with peptide diluted in BBS (100 µl, 1 µg/well) and the plate was incubated at 4° C. in a wetbox overnight (air-tight container with moistened cotton balls). The plates were emptied and then washed three times with BBS containing 0.1% Tween-20 (BBS-TW) by repeated filling and emptying using a semi-automated plate washer. The plates were blocked by completely filling each well with BBS-TW containing 1% BSA and 0.1% gelatin (BBS-TW-BG) and incubating for 2 hours at room temperature. The plates were emptied and sera of both pre- and post-immune serum were added to wells. The first well contained sera at 1:50 in BBS. The sera were then serially titrated eleven more times across the plate at a ratio of 1:1 for a final (twelfth) dilution of 1:204,800. The plates were incubated overnight at 4° C. The plates were emptied and washed three times as described.

Biotinylated goat anti-rabbit IgG (100 µl) was added to each microtiter plate test well and incubated for four hours at room temperature. The plates were emptied and washed three times. Horseradish peroxidase-conjugated Streptavidin (100 µl diluted 1:10,000 in BBS-TW-BG) was added to each well and incubated for two hours at room temperature. The plates were emptied and washed three times. The ABTS was prepared fresh from stock by combining 10 ml of citrate buffer (0.1 M at pH 4.0), 0.2 ml of the stock solution (15 mg/ml in water) and 10 µl of 30% hydrogen peroxide. The ABTS solution (100 µl) was added to each well and incubated at room temperature. The plates were read at 414 nm, 20 minutes following the addition of substrate.

Preparation of Peptide Affinity Purification Column:

The affinity column was prepared by conjugating 5 mg of peptide to 10 ml of cyanogen bromide-activated Sepharose 4B and 5 mg of peptide to hydrazine-Sepharose 4B. Briefly, 100 µl of DMF was added to peptide (5 mg) and the mixture was vortexed until the contents were completely wetted. Water was then added (900 µl) and the contents were vortexed until the peptide dissolved. Half of the dissolved peptide (500 µl) was added to separate tubes containing 10 ml of cyanogen-bromide activated Sepharose 4B in 0.1 ml of borate buffered saline at pH 8.4 (BBS) and 10 ml of hydrazine-Sepharose 4B in 0.1 M carbonate buffer adjusted to pH 4.5 using excess EDC in citrate buffer pH 6.0. The conjugation reactions were allowed to proceed overnight at room temperature. The conjugated Sepharose was pooled and loaded onto fitted columns, washed with 10 ml of BBS, blocked with 10 ml of 1 M glycine and washed with 10 ml 0.1 M glycine adjusted to pH 2.5 with HCl and re-neutralized in BBS. The column was washed with enough volume for the optical density at 280 nm to reach baseline.

Affinity Purification of Antibodies

The peptide affinity column was attached to a UV monitor and chart recorder. The titered rabbit antiserum was thawed and pooled. The serum was diluted with one volume of BBS and allowed to flow through the columns at 10 ml per minute. The non-peptide immunoglobulins and other proteins were washed from the column with excess BBS until the optical density at 280 nm reached baseline. The columns were disconnected and the affinity purified column was eluted using a stepwise pH gradient from pH 7.0 to 1.0. The elution was monitored at 280 nm and fractions containing antibody (pH 3.0 to 1.0) were collected directly into excess 0.5 M BBS. Excess buffer (0.5 M BBS) in the collection tubes served to neutralize the antibodies collected in the acidic fractions of the pH gradient.

The entire procedure was repeated with "depleted" serum to ensure maximal recovery of antibodies. The eluted material was concentrated using a stirred cell apparatus and a membrane with a molecular weight cutoff of 30 kD. The concentration of the final preparation was determined using an optical density reading at 280 nm. The concentration was determined using the following formula: mg/ml=$OD_{280}$/1.4.

It will be appreciated that in certain embodiments, additional steps may be used to purify antibodies of the invention. In particular, it may prove advantageous to repurify antibodies, e.g., against one of the peptides that was used in generating the antibodies. It is to be understood that the present invention encompasses antibodies that have been prepared with such additional purification or repurification steps. It will also be appreciated that the purification process may affect the binding between samples and the inventive antibodies.

Example 2

Preparing and Staining Tissue Arrays

This example describes a method that was employed to prepare the tissue arrays that were used in the Examples. This example also describes how the antibody staining was performed.

Tissue arrays were prepared by inserting full-thickness cores from a large number of paraffin blocks (donor blocks) that contain fragments of tissue derived from many different patients and/or different tissues or fragments of tissues from a single patient, into a virgin paraffin block (recipient block) in a grid pattern at designated locations in a grid. A standard slide of the paraffin embedded tissue (donor block) was then made which contained a thin section of the specimen amenable to H & E staining A trained pathologist, or the equivalent versed in evaluating tumor and normal tissue, designated the region of interest for sampling on the tissue array (e.g., a tumor area as opposed to stroma). A commercially available tissue arrayer from Beecher Instruments was then used to remove a core from the donor block which was then inserted into the recipient block at a designated location. The process was repeated until all donor blocks had been inserted into the recipient block. The recipient block was then thin-sectioned to yield 50-300 slides containing cores from all cases inserted into the block.

The selected antibodies were then used to perform immunohistochemical staining using the DAKO Envision+, Peroxidase IHC kit (DAKO Corp., Carpenteria, Calif.) with DAB substrate according to the manufacturer's instructions. FIG. 1 shows exemplary IHC staining images of samples that are TLE3-negative (S0643−) and TLE3-positive (S0643+).

Example 3

TLE3 Expression Correlates with Response to Chemotherapy in Cancer Patients

Figure 2:
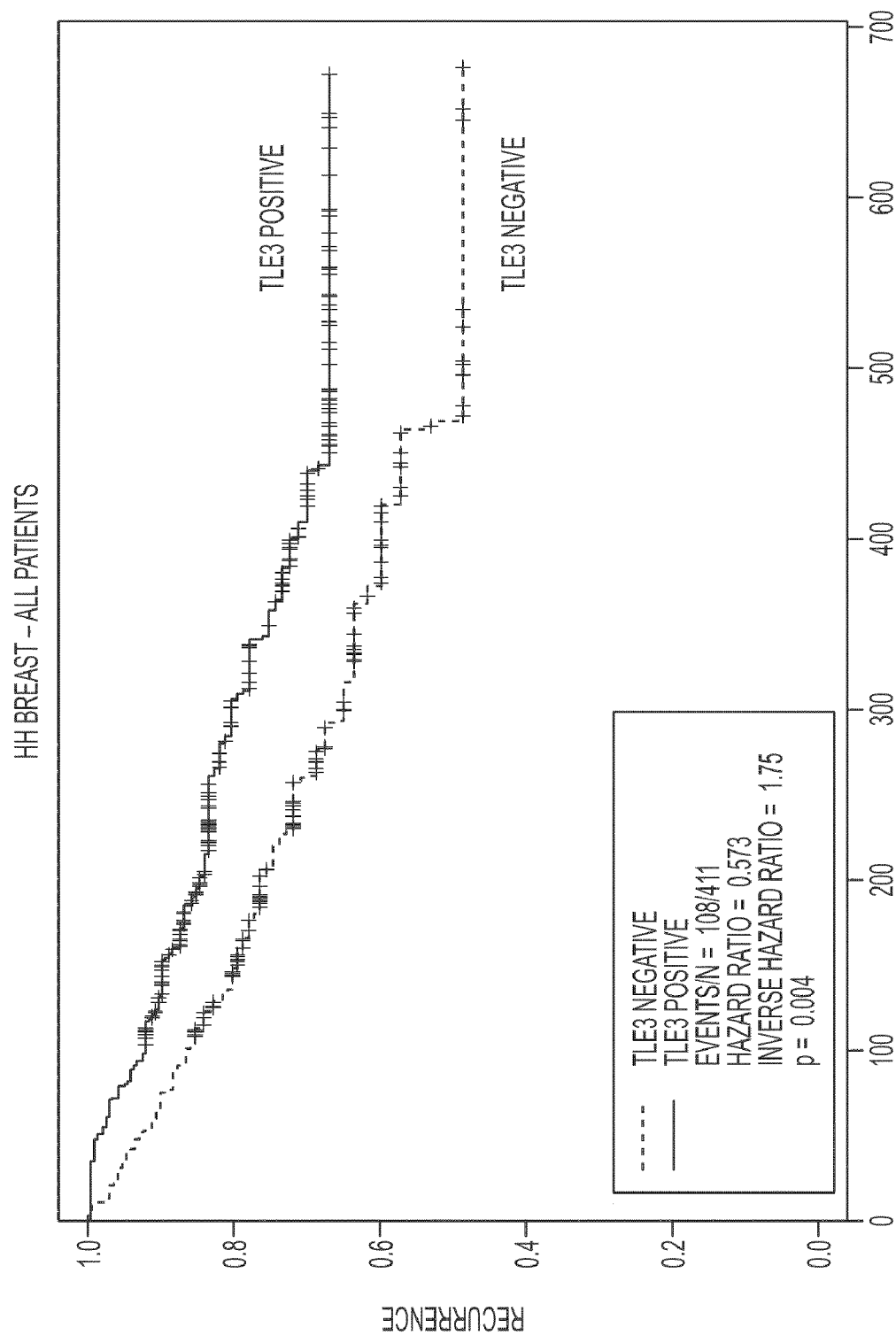
FIG. 2 shows Kaplan-Meier recurrence curves that were generated using all patients in the Huntsville Hospital (HH) breast cancer cohort after classification based on staining with an antibody raised against the TLE3 marker. Recurrence data from TLE3-positive and TLE3-negative patients were used to generate the top and bottom curves, respectively. As shown in the Figure, antibody binding to the TLE3 marker correlates with improved prognosis across this breast cancer cohort (HR=0.573, p<0.004).
Figure 3:
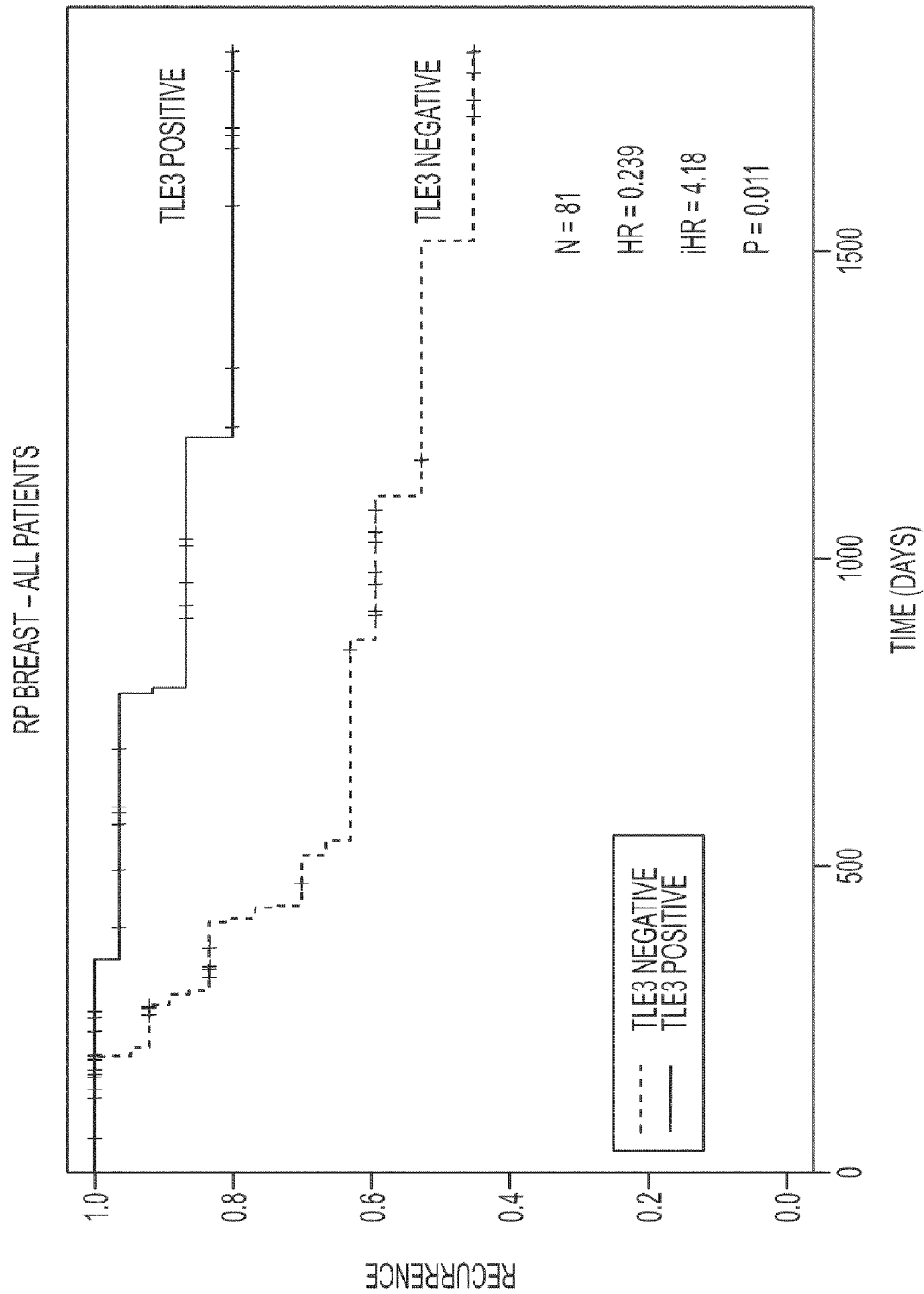
FIG. 3 shows Kaplan-Meier recurrence curves that were generated using all patients in the Roswell Park Cancer Institute (RPI) breast cancer cohort after classification based on staining with an antibody raised against the TLE3 marker. The selected patients in the RP cohort were all triple negative for the ER (estrogen receptor, Entrez GeneID 2099), PR (progesterone receptor, Entrez GeneID 5241) and HER-2 markers (v-erb-b2 erythroblastic leukemia viral oncogene homolog 2, Entrez GeneID 2064). Recurrence data from TLE3-positive and TLE3-negative patients were used to generate the top and bottom curves, respectively. As shown in the Figure, antibody binding to the TLE3 marker correlates with improved prognosis across this breast cancer cohort (HR=0.24, p<0.011).

Tumor samples from two different breast cancer cohorts—Huntsville Hospital (HH) and Roswell Park Cancer Institute (RP)—were stained with the TLE3 antibody of Example 1. Treatment and recurrence data were available for all patients in both cohorts. FIG. 2 shows Kaplan-Meier recurrence curves that were generated using all patients in the HH cohort after classification based on staining with the TLE3 antibody. Recurrence data from TLE3-positive and TLE3-negative patients were used to generate the top and bottom curves, respectively. As shown in the Figure, antibody binding to the TLE3 marker correlates with improved prognosis across this breast cancer cohort (HR=0.573, p=0.004). FIG. 3 shows Kaplan-Meier recurrence curves that were generated in a similar fashion using all patients in the RP cohort. As with the HH cohort, antibody binding to the TLE3 marker was found to correlate with improved prognosis (HR=0.239, p=0.011).

Figure 4:
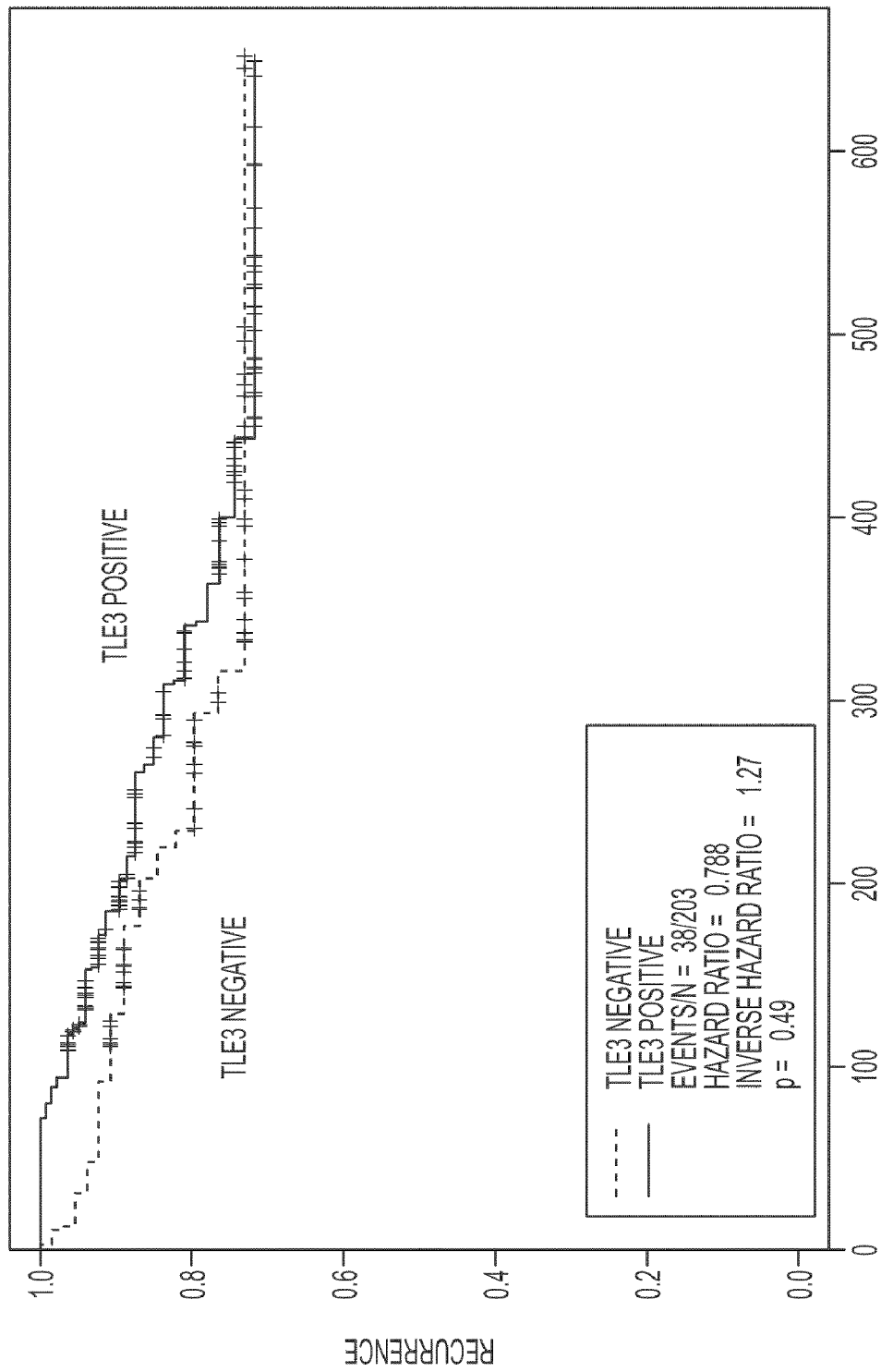
FIG. 4 shows Kaplan-Meier recurrence curves that were generated using patients in the HH breast cancer cohort of FIG. 1 that did not receive chemotherapy. Recurrence data from TLE3-positive and TLE3-negative patients in this subset were used to generate the top and bottom curves, respectively. As shown in the Figure, antibody binding to the TLE3 marker loses its correlation with prognosis in breast cancer patients that did not receive chemotherapy (HR=0.788, p=0.49).
Figure 5:
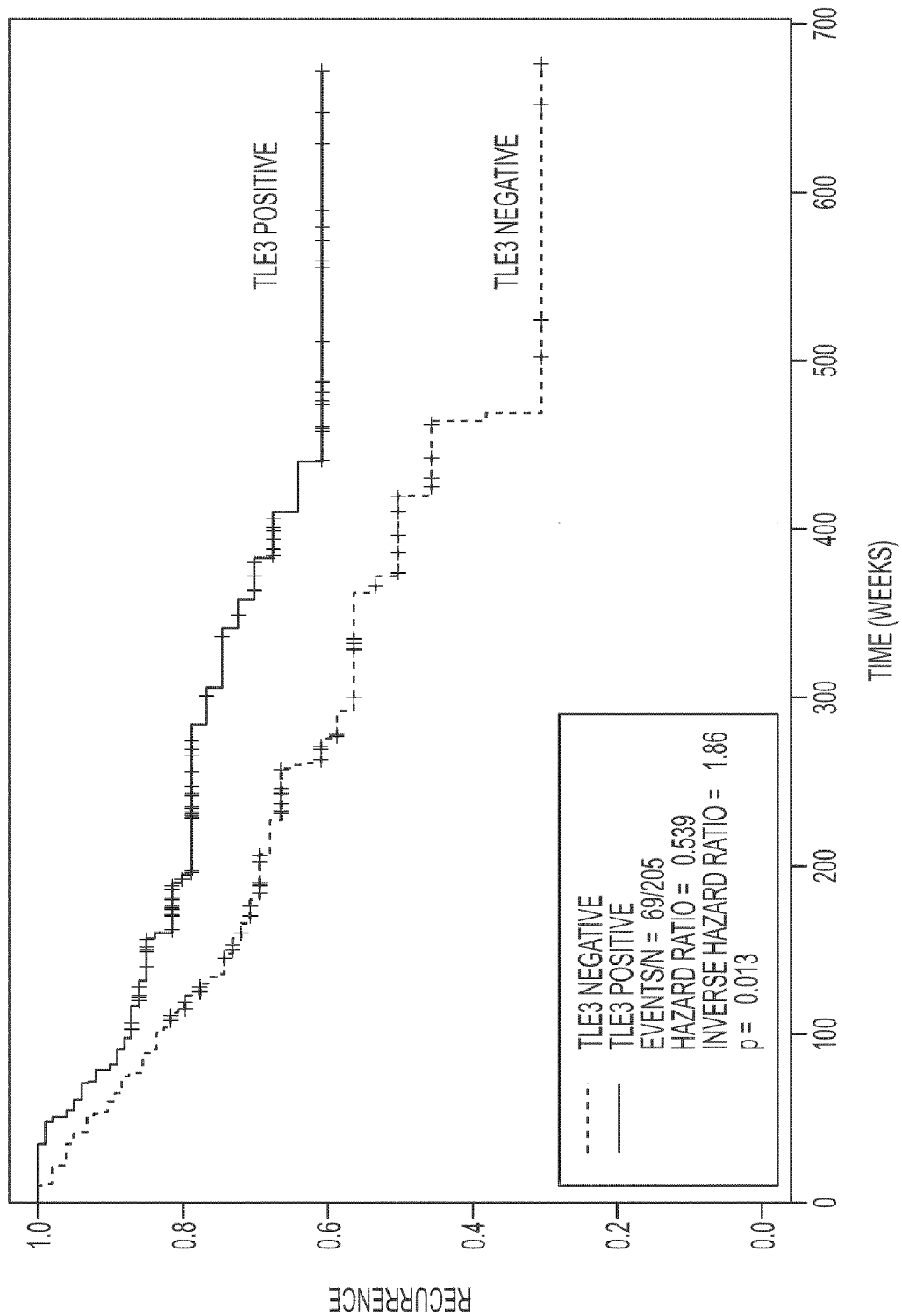
FIG. 5 shows Kaplan-Meier recurrence curves that were generated using patients in the HH breast cancer cohort of FIG. 1 that did receive chemotherapy. Recurrence data from TLE3-positive and TLE3-negative patients in this subset were used to generate the top and bottom curves, respectively. As shown in the Figure, the correlation between antibody binding to the TLE3 marker and prognosis was restored in patients that did receive chemotherapy (HR=0.539, p<0.013).
Figure 18:
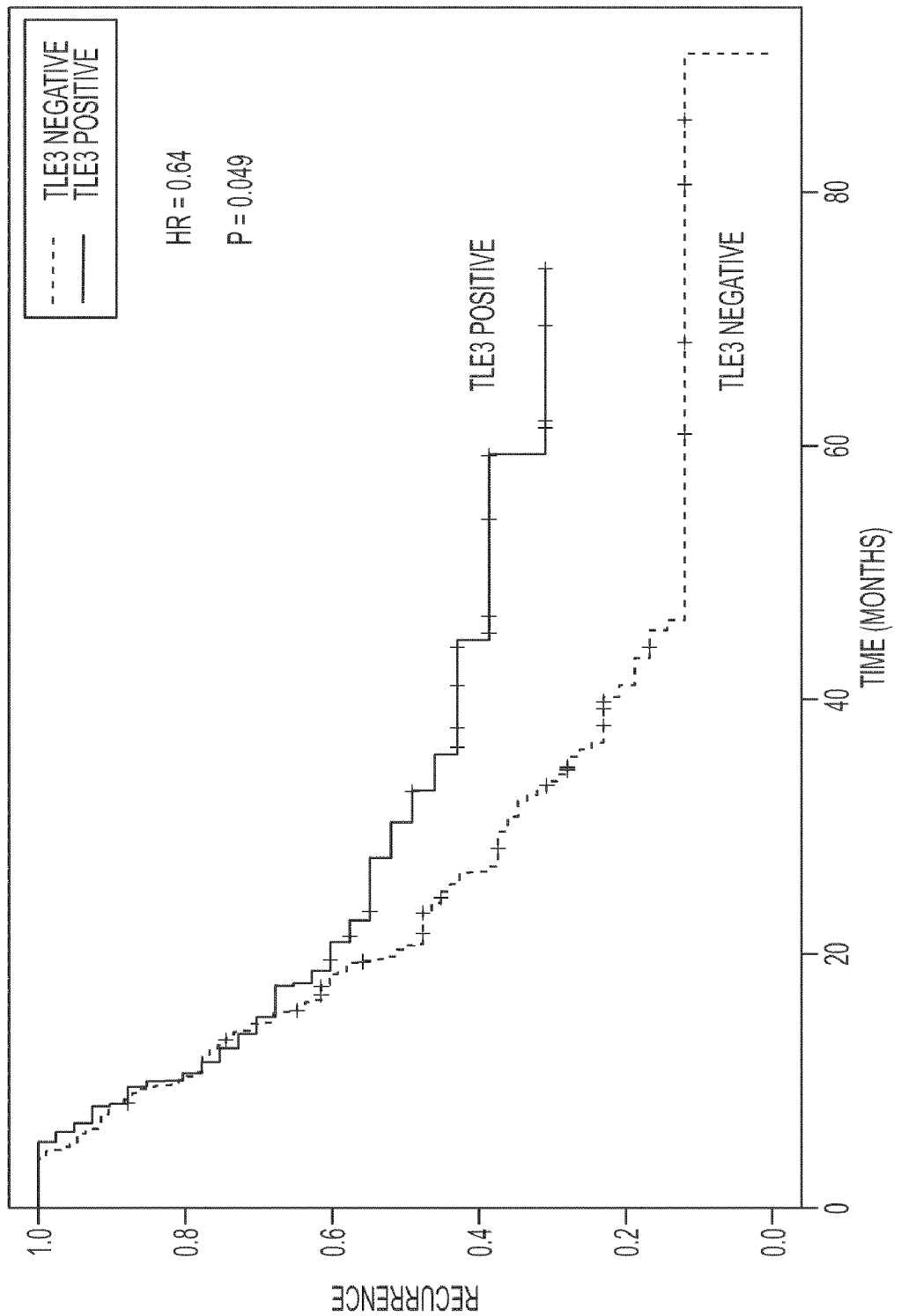
FIG. 18 shows Kaplan-Meier recurrence curves that were generated using patients in the University of Alabama at Birmingham (UAB) ovarian cancer cohort. All patients received paclitaxel. Most patients also received platinum chemotherapy (carboplatin or cisplatin). Recurrence data from TLE3-positive and TLE3-negative patients in this subset were used to generate the top and bottom curves, respectively. As shown in the Figure, antibody binding to the TLE3 marker correlated with prognosis in these treated patients (HR=0.64, p<0.049).

In order to determine whether TLE3 expression is correlated with response to chemotherapy, separate Kaplan-Meier recurrence curves were generated using HH cohort patients that did or did not receive chemotherapy (FIGS. 4 and 5, respectively). As shown in FIG. 4, antibody binding to the TLE3 marker lost its correlation with prognosis in patients that did not receive chemotherapy (HR=0.788, p=0.490). However, as shown in FIG. 5, the correlation was restored in patients that did receive chemotherapy (HR=0.539, p=0.013). These results demonstrate that TLE3 expression is correlated with improved response to chemotherapy (i.e., TLE3-positive cancers are more likely to respond to chemotherapy than TLE-3 negative cancers). Kaplan-Meier recurrence curves that were generated using patients in the RP breast cancer cohort that received chemotherapy are consistent with this prediction model (see FIG. 6, HR=0.194, p=0.010). Kaplan-Meier recurrence curves that were generated using patients in the UAB ovarian cancer cohort that received chemotherapy are also consistent with this prediction model (see FIG. 18, HR=0.64, p=0.049).

Example 4

Specific Chemotherapeutic Correlations

Since different patients in the HH and RP cohorts received different types of chemotherapy we were also able to determine whether TLE3 expression correlates with response to specific types of chemotherapy.

Figure 7:
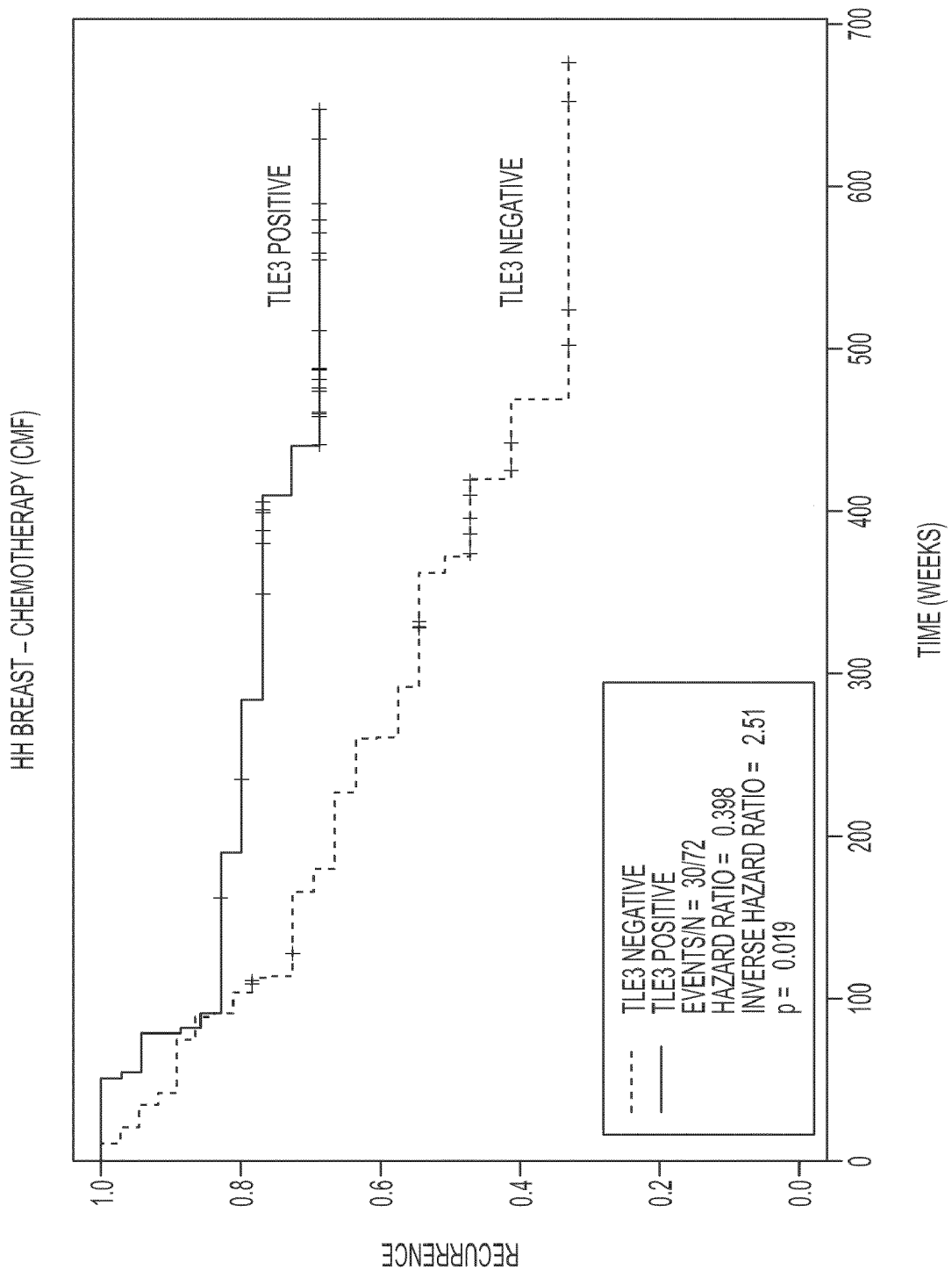
FIG. 7 shows Kaplan-Meier recurrence curves that were generated using patients in the HH breast cancer cohort of FIG. 5 that received CMF (cyclophosphamide, methotrexate and 5-fluorouracil) chemotherapy. Recurrence data from TLE3-positive and TLE3-negative patients in this subset were used to generate the top and bottom curves, respectively. As shown in the Figure, antibody binding to the TLE3 marker correlates with improved prognosis across this subset of treated patients (HR=0.398, p<0.019).
Figure 9:
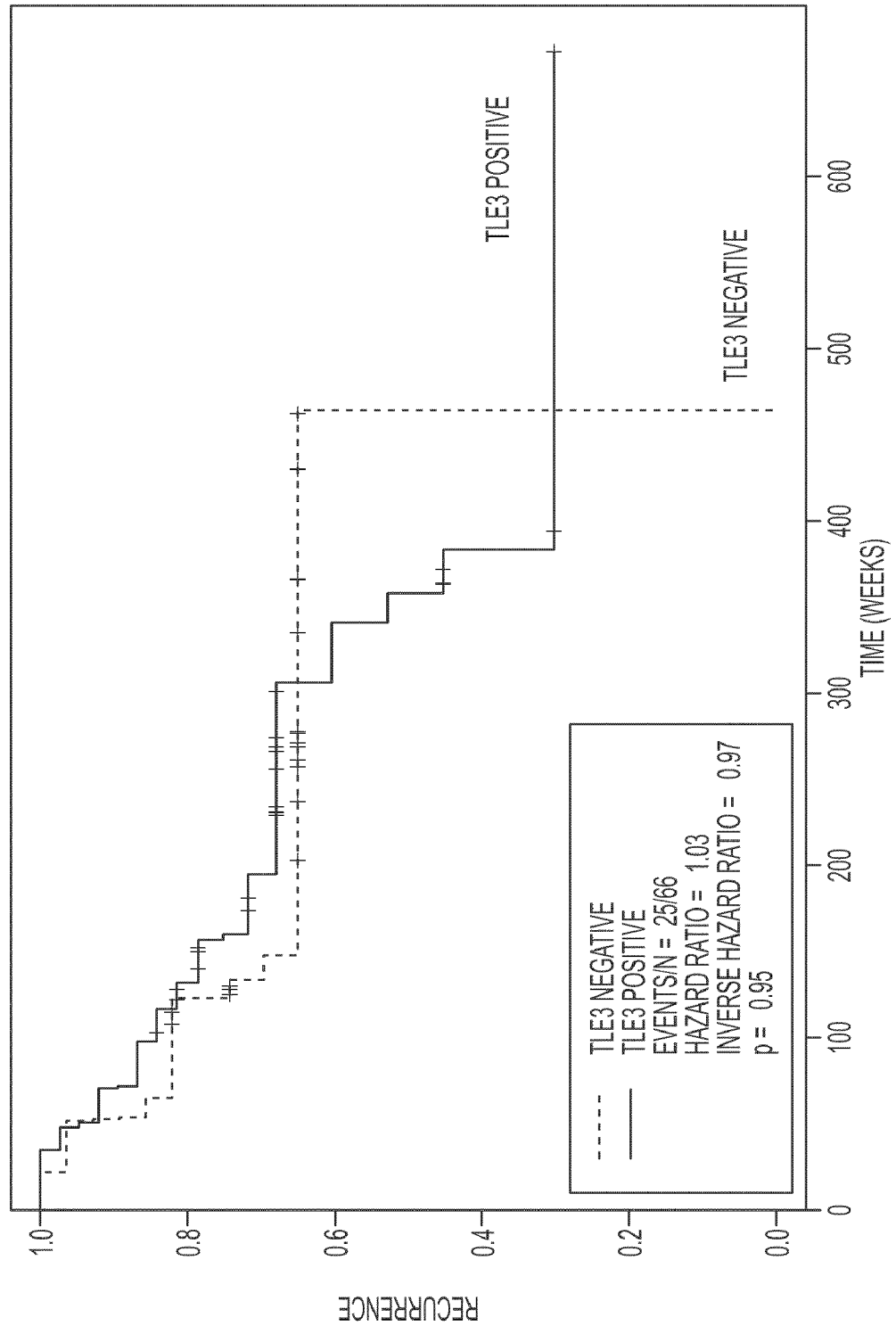
FIG. 9 shows Kaplan-Meier recurrence curves that were generated using patients in the HH breast cancer cohort of FIG. 8 that received CA or CAF chemotherapy only (i.e., without a taxane). Recurrence data from TLE3-positive and TLE3-negative patients in this subset were used to generate the top and bottom curves, respectively. As shown in the Figure, there is no correlation between antibody binding to the TLE3 marker and prognosis in this subset of treated patients (HR=1.03, p=0.95).

FIG. 7 shows Kaplan-Meier recurrence curves that were generated using patients in the HH breast cancer cohort of FIG. 5 that received CMF (cyclophosphamide, methotrexate and 5-fluorouracil) chemotherapy. Recurrence data from TLE3-positive and TLE3-negative patients in this subset were used to generate the top and bottom curves, respectively. As shown in FIG. 7, antibody binding to the TLE3 marker correlates with improved prognosis across this subset of treated patients (HR=0.398, p=0.019). Based on the results below which demonstrated a loss of correlation for patients in the HH cohort that were treated with CA (cyclophosphamide and adriamycin, HR=1.000) or CAF (cyclophosphamide, adriamycin and 5-fluorouracil, HR=1.000) we were able to establish that the predictive correlation in FIG. 7 is between TLE3 binding and treatment with methotrexate (see also FIG. 9 which combines the CA and CAF treated subsets, HR=1.030).

Figure 8:
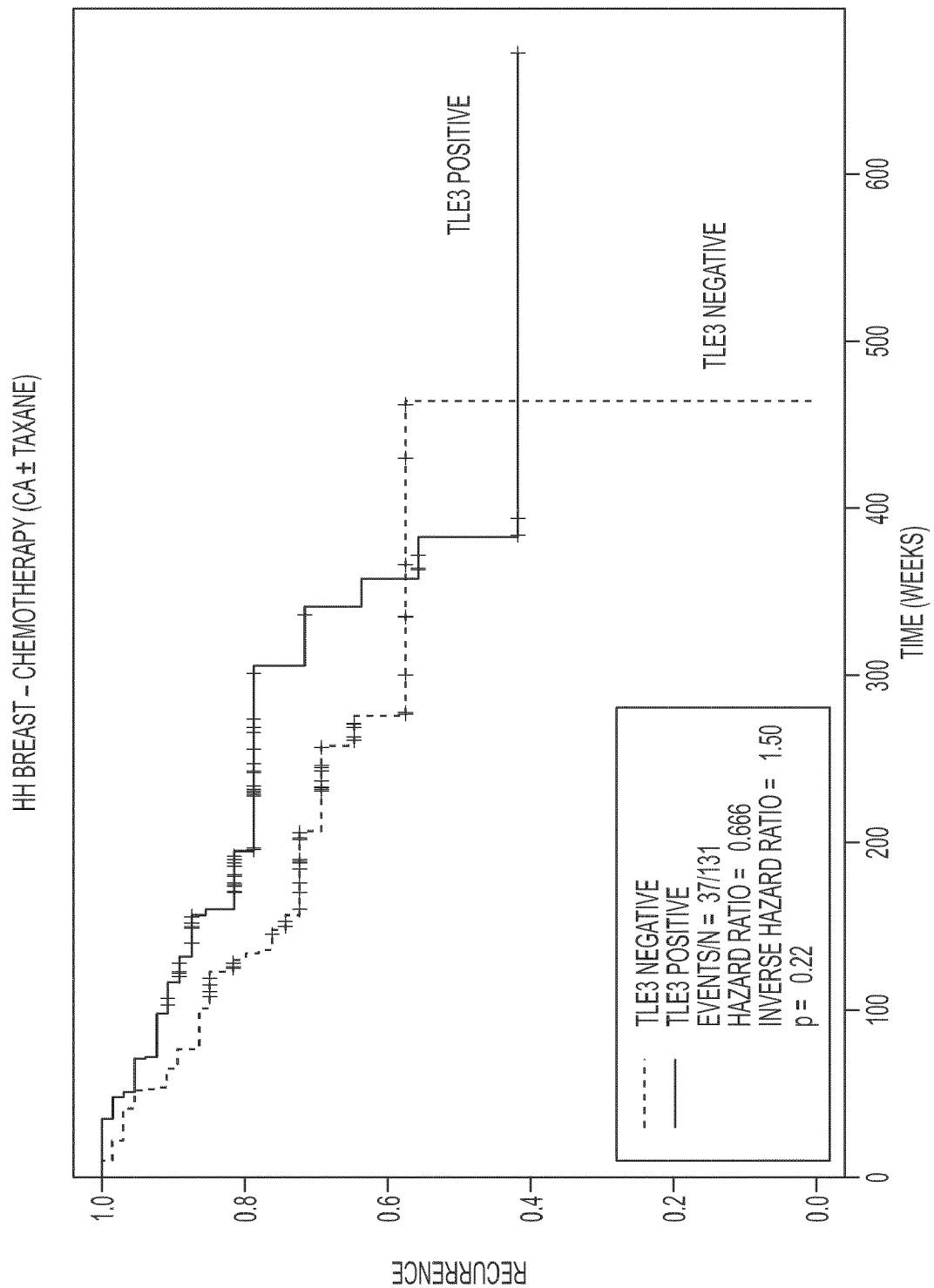
FIG. 8 shows Kaplan-Meier recurrence curves that were generated using patients in the HH breast cancer cohort of FIG. 5 that received CA (cyclophosphamide and adriamycin) or CAF (cyclophosphamide, adriamycin and 5-fluorouracil) chemotherapy (with or without a taxane). Recurrence data from TLE3-positive and TLE3-negative patients in this subset were used to generate the top and bottom curves, respectively. As shown in the Figure, the correlation between antibody binding to the TLE3 marker and prognosis loses significance in this subset of treated patients (HR=0.666, p=0.22).

FIG. 8 shows Kaplan-Meier recurrence curves that were generated using patients in the HH breast cancer cohort of FIG. 5 that received CA or CAF chemotherapy (with or without a taxane). As shown in the Figure, the correlation between antibody binding to the TLE3 marker and prognosis loses significance in this subset of treated patients (HR=0.666, p=0.22). When the curves were generated using patients that received CA or CAF chemotherapy only (i.e., without a taxane) the significance was further reduced (see FIG. 9, HR=1.030, p=0.95). However, the correlation was restored in patients that received CA or CAF in combination with a taxane (see FIG. 10, HR=0.114, p=0.038). These results demonstrate a correlation between TLE3 binding and treatment with a taxane.

Figure 6:
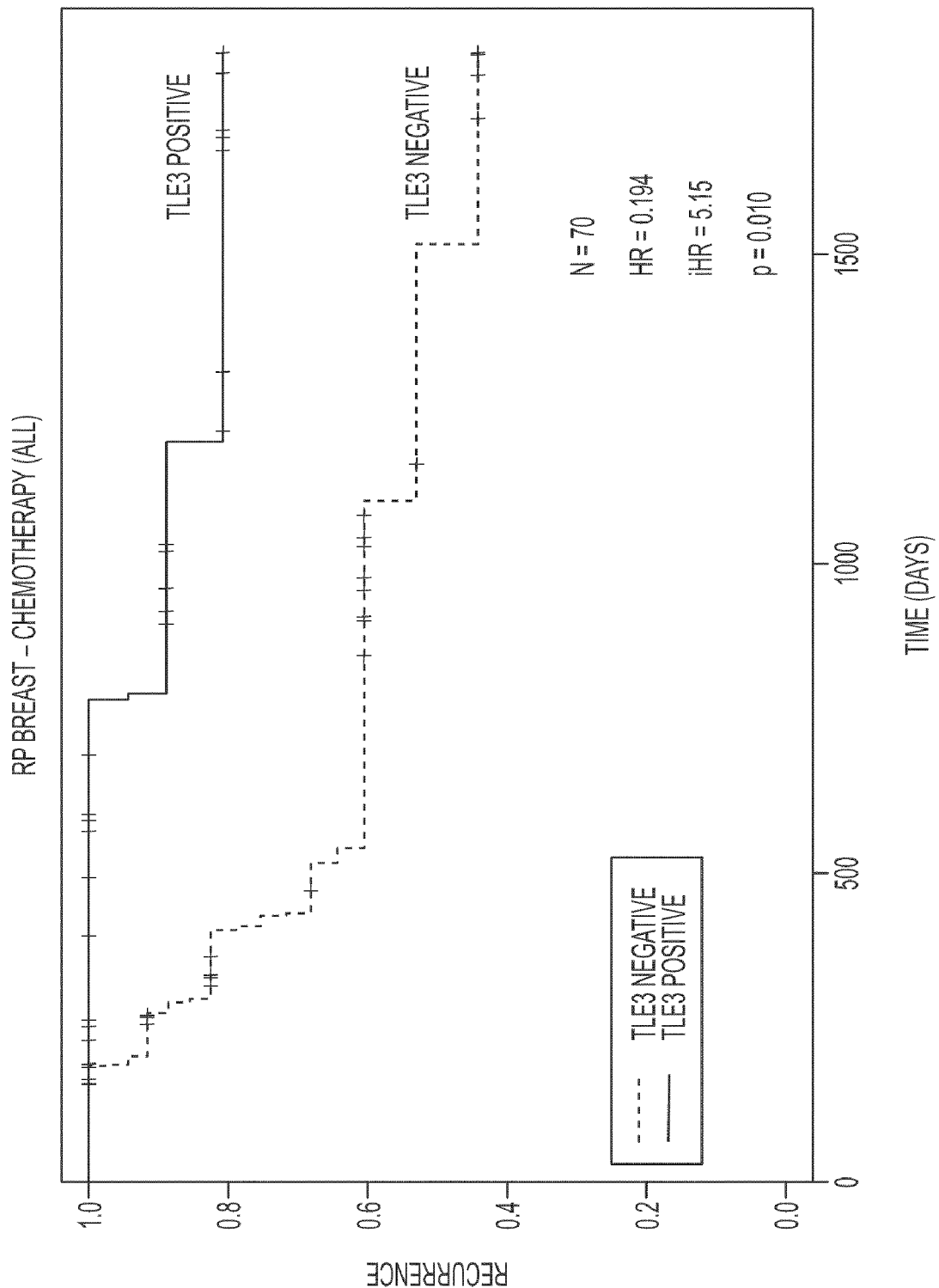
FIG. 6 shows Kaplan-Meier recurrence curves that were generated using patients in the RP breast cancer cohort of FIG. 2 that did receive chemotherapy. Recurrence data from TLE3-positive and TLE3-negative patients in this subset were used to generate the top and bottom curves, respectively. As shown in the Figure, antibody binding to the TLE3 marker correlates with improved prognosis across this subset of breast cancer patients (HR=0.194, p=0.010). These results parallel those obtained in FIG. 5 with the HH cohort.
Figure 11:
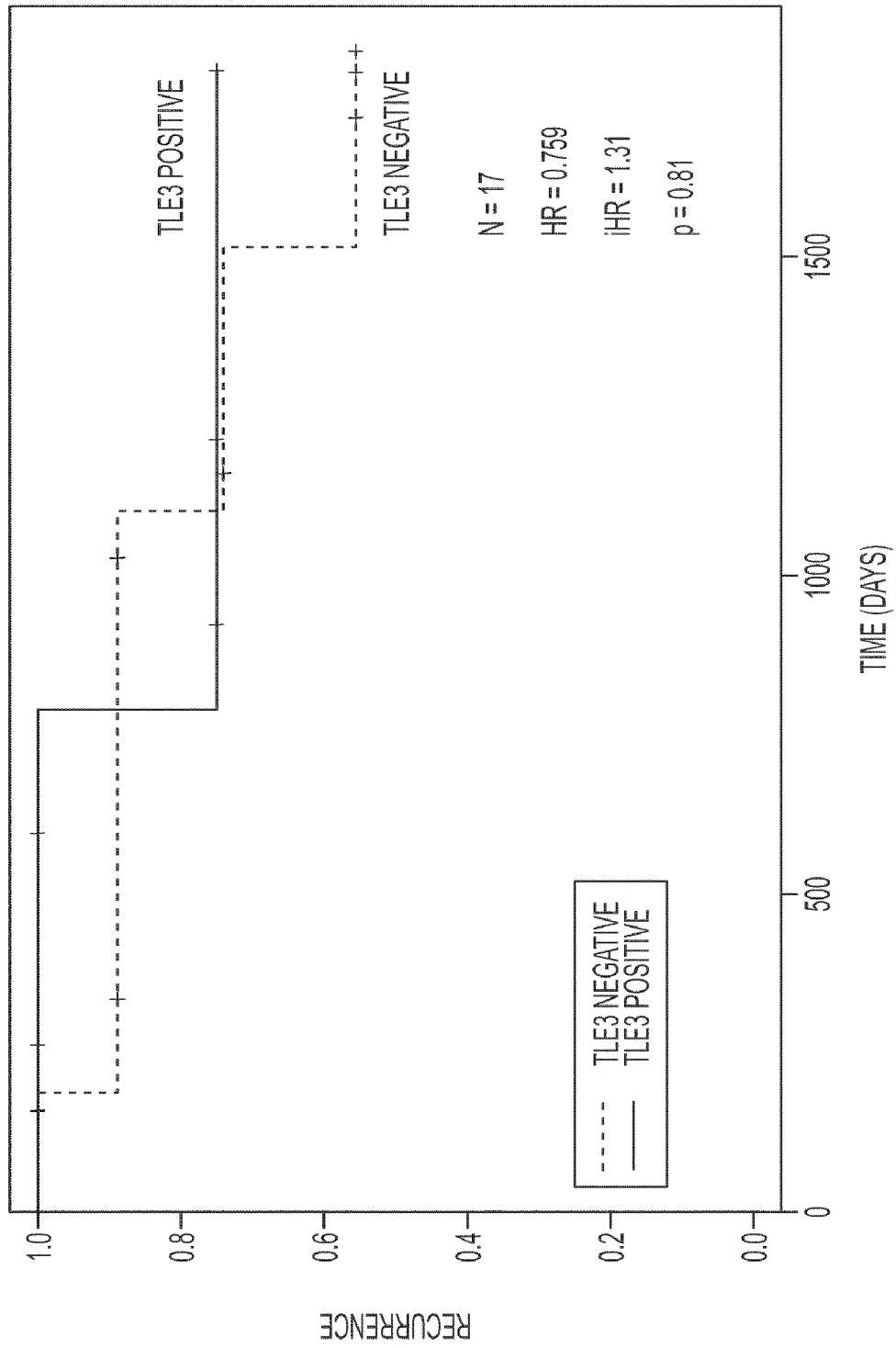
FIG. 11 shows Kaplan-Meier recurrence curves that were generated using patients in the RP breast cancer cohort of FIG. 6 that received CA chemotherapy only (i.e., without a taxane). Recurrence data from TLE3-positive and TLE3-negative patients in this subset were used to generate the top and bottom curves, respectively. As shown in the Figure, there is no correlation between antibody binding to the TLE3 marker and prognosis in this subset of treated patients (HR=0.759, p=0.81).

FIG. 11 shows Kaplan-Meier recurrence curves that were generated using patients in the RP breast cancer cohort of FIG. 6 that received CA chemotherapy only (i.e., without a taxane). Recurrence data from TLE3-positive and TLE3-negative patients in this subset were used to generate the top and bottom curves, respectively. As shown in the Figure, there is no correlation between antibody binding to the TLE3 marker and prognosis in this subset of treated patients (HR=0.759, p=0.81). The correlation was restored when the curves were generated using patients that received CA chemotherapy in combination with a taxane (see FIG. 12, HR=0.153, p=0.018). These results support the results of FIGS. 8 and 9 that were obtained using samples from the HH cohort.

FIG. 13 shows Kaplan-Meier recurrence curves that were generated using patients in the RP breast cancer cohort of FIG. 6 that received a taxane or CMF. Some of the patients receiving a taxane also received CA. Recurrence data from TLE3-positive and TLE3-negative patients in this subset were used to generate the top and bottom curves, respectively. As shown in the Figure, antibody binding to the TLE3 marker correlates with improved prognosis across this subset of treated patients (HR=0.137, p=0.011).

Figure 14:
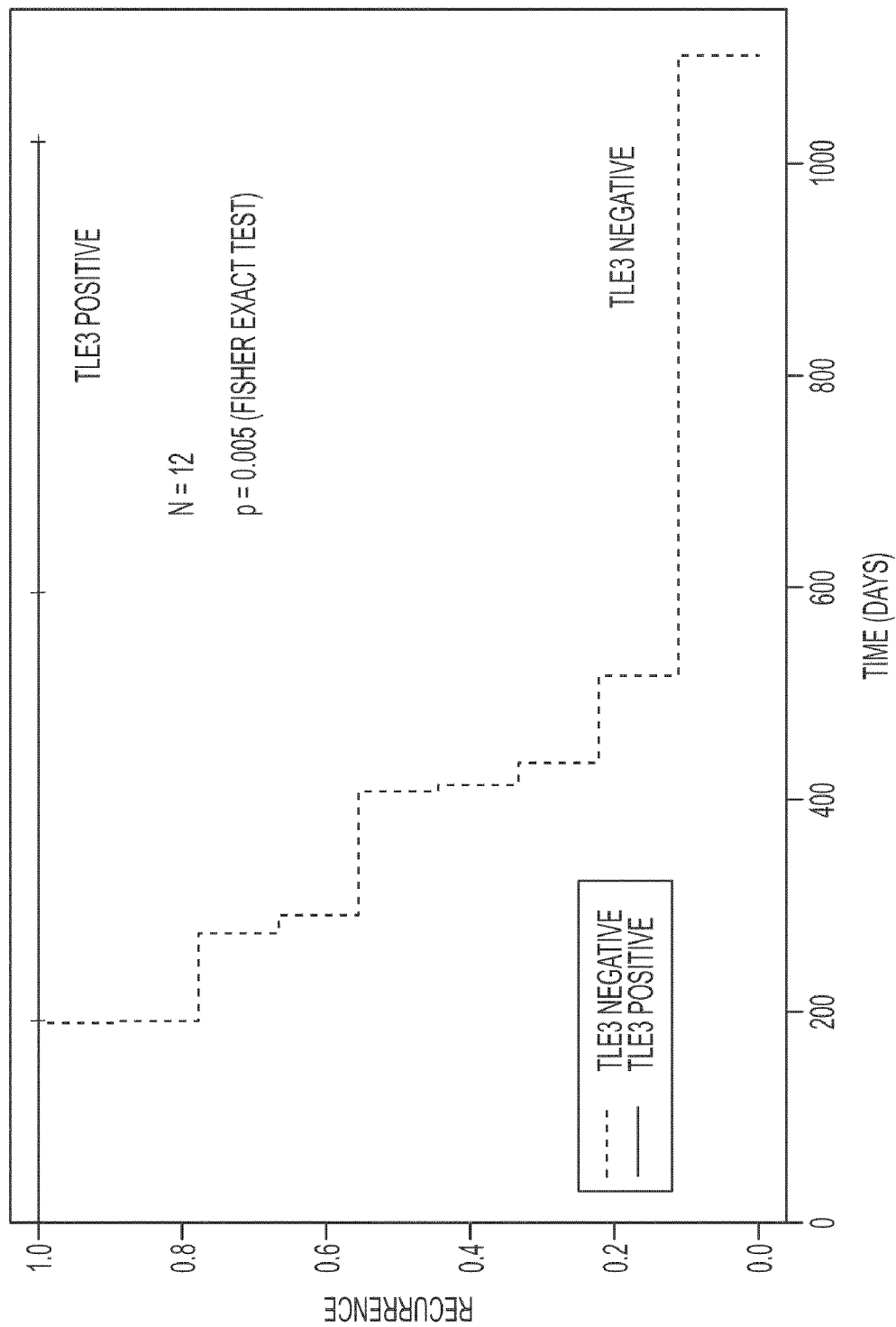
FIG. 14 shows Kaplan-Meier recurrence curves that were generated using patients in the RP breast cancer cohort of FIG. 6 that received neoadjuvant chemotherapy. Recurrence data from TLE3-positive and TLE3-negative patients in this subset were used to generate the top and bottom curves, respectively. The sample size was small (N=12); however, as shown in the Figure, antibody binding to the TLE3 marker showed significant correlation with improved prognosis across this subset of treated patients when measured using the Fisher Exact Test (p=0.005).

FIG. 14 shows Kaplan-Meier recurrence curves that were generated using patients in the RP breast cancer cohort of FIG. 6 that received neoadjuvant chemotherapy. Recurrence data from TLE3-positive and TLE3-negative patients in this subset were used to generate the top and bottom curves, respectively. The sample size was small (N=12); however, as shown in the Figure, antibody binding to the TLE3 marker showed significant correlation with improved prognosis across this subset of treated patients when measured using the Fisher Exact Test (p=0.005). In addition, of the 12 patients receiving neoadjuvant chemotherapy, two received CA (both showed recurrence) while ten received CA with a taxane (seven showed recurrence, three did not). Notably, the three patients that did not show any recurrence were the only patients with TLE3-positive samples. These results are significant since they show that the correlation between TLE3 binding and response to chemotherapy applies irrespective of whether treatment is administered in an adjuvant or neoadjuvant setting.

Figure 15:
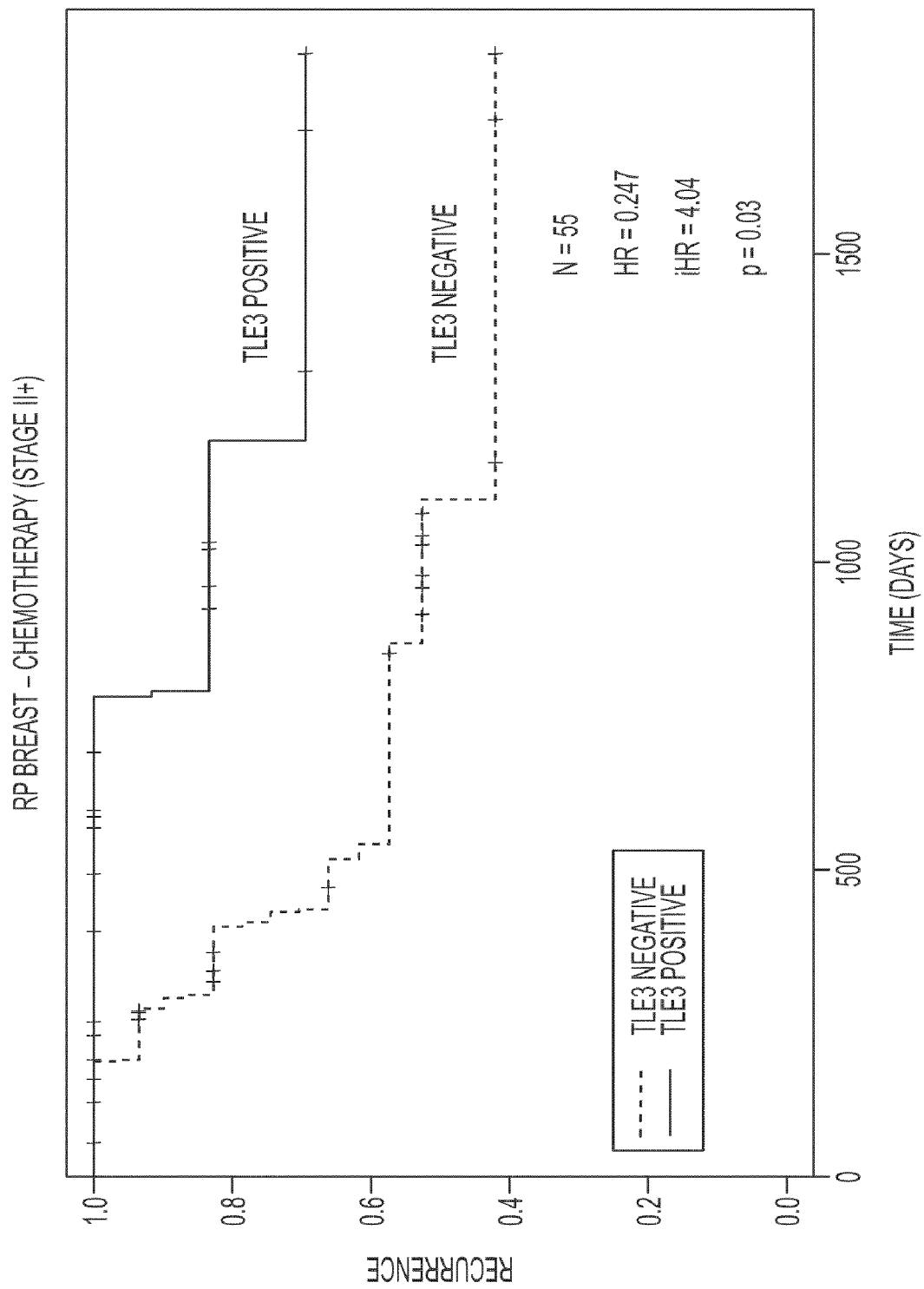
FIGS. 15-17 show Kaplan-Meier recurrence curves that were generated using patients in the RP breast cancer cohort of FIG. 6 that received chemotherapy. Recurrence data from TLE3-positive and TLE3-negative patients with stage II+ (FIG. 15), stage IIb+ (FIG. 16) and stage III+ (FIG. 17) cancers were used to generate the top and bottom curves, respectively. In each case, antibody binding to the TLE3 marker correlated with improved prognosis across these subsets of treated patients. The sample size was small in the subset of FIG. 17 (N=19); however significance was obtained when measured using the Fisher Exact Test (p=0.020).
Figure 16:
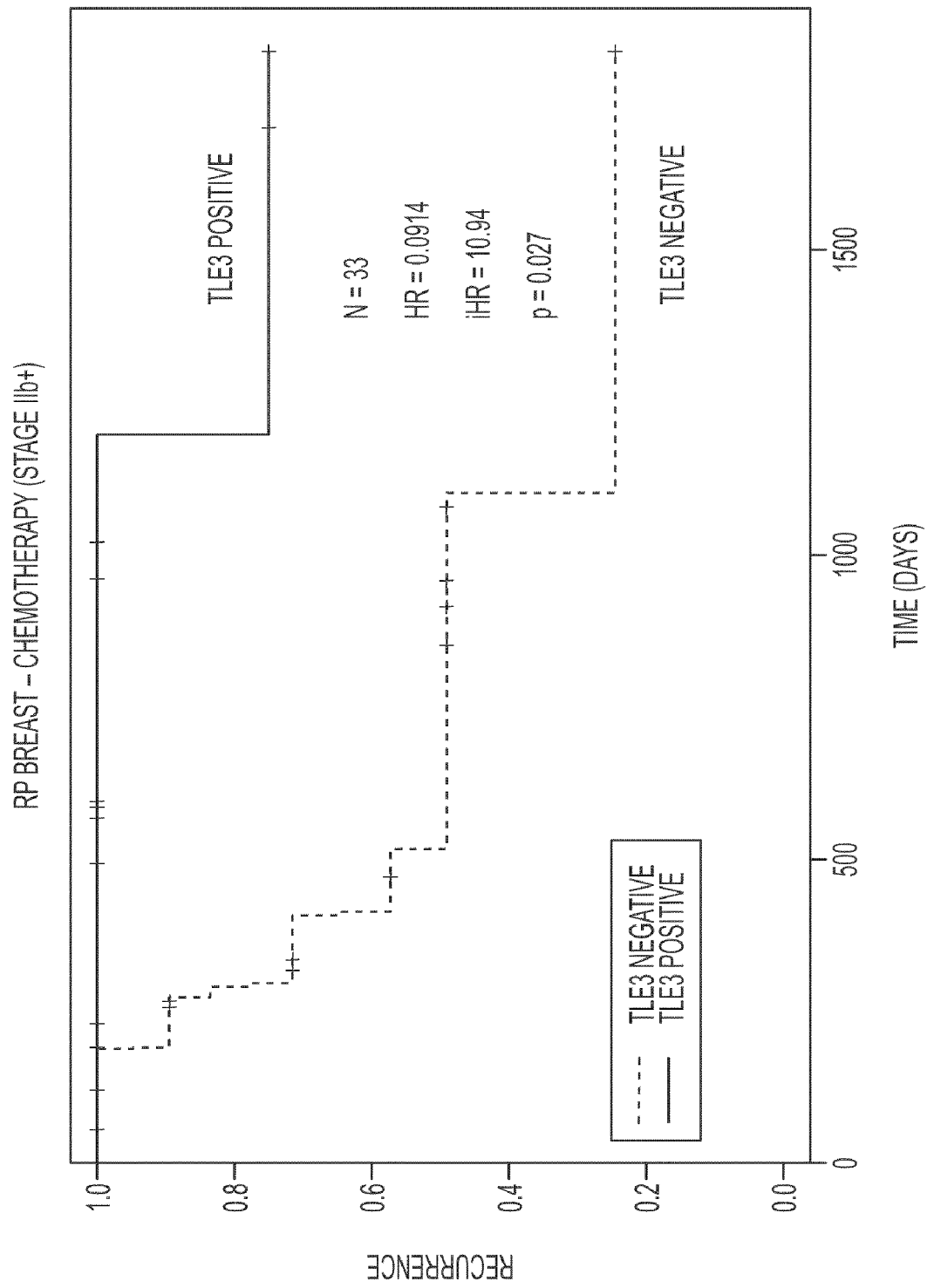
Figure 17:
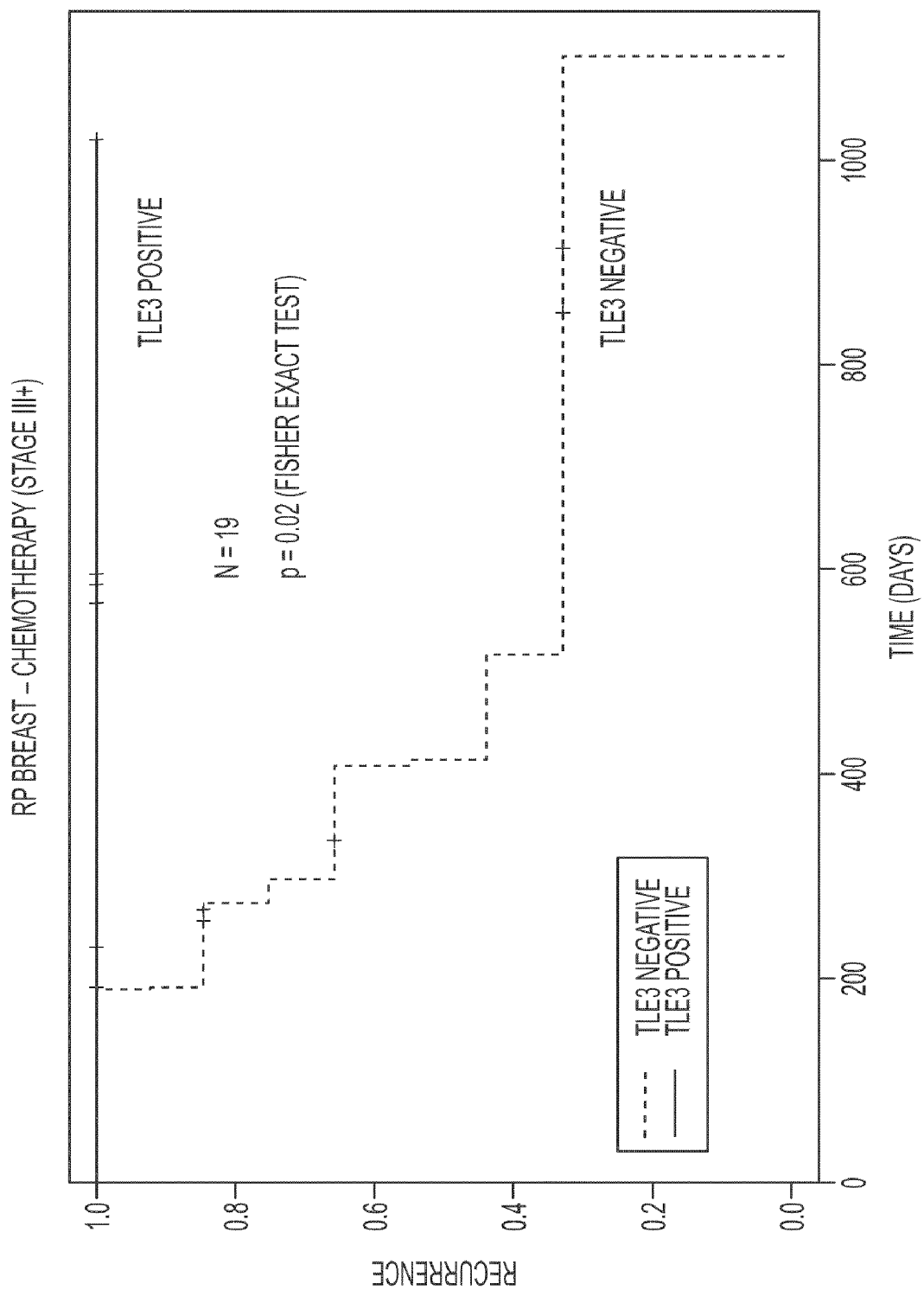

FIGS. 15-17 show Kaplan-Meier recurrence curves that were generated using patients in the RP breast cancer cohort of FIG. 6 that received chemotherapy. Recurrence data from TLE3-positive and TLE3-negative patients with stage II+ (FIG. 15), stage IIb+ (FIG. 16) and stage III+ (FIG. 17) cancers were used to generate the top and bottom curves, respectively. In each case, antibody binding to the TLE3 marker correlated with improved prognosis across these subsets of treated patients. The sample size was small in the subset of FIG. 17 (N=19); however significance was obtained when measured using the Fisher Exact Test (p=0.020). These results are of clinical importance since they demonstrate that the predictive power of the TLE3 marker is independent of stage and remains significant even in patients with the worst prognosis (e.g., stage III+ patients).

Example 5

Bivariate Analysis

In order to confirm that the predictive power of TLE3 is independent of other clinical factors (e.g., age, tumor size, nodes status, necrosis, etc.) we performed bivariate statistical analysis using results from the RP breast cohort. The results are summarized in Table 1 below. As shown in the Table, prediction using TLE3 remained significant in all bivariate analyses demonstrating its independence of other clinical factors.

TABLE 1

Bivariate Analysis

| Factor 1 | Factor 2 | N | HR for TLE3 | p for TLE3 | HR | P |
|---|---|---|---|---|---|---|
| TLE3 | — | 81 | 0.239 | 0.0110 | — | — |
| TLE3 | Age | 81 | 0.223 | 0.0082 | 0.967 | 0.1200 |
| TLE3 | Tumor Size | 78 | 0.219 | 0.0077 | 1.292 | 0.0002 |
| TLE3 | Nodes Met Ca[1] | 79 | 0.252 | 0.0150 | 1.066 | 0.0086 |
| TLE3 | Necrosis | 72 | 0.232 | 0.0100 | 1.903 | 0.2600 |
| TLE3 | Vasc. Lymph Inv.[2] | 74 | 0.205 | 0.0071 | 0.412 | 0.0790 |
| TLE3 | Stage | 80 | 0.284 | 0.0280 | 2.063 | 0.0130 |
| TLE3 | Contains Tax[3] | 70 | 0.168 | 0.0061 | 2.749 | 0.0980 |

[1]Nodes found with metastatic cancer.
[2]Vascular lymphatic invasion.
[3]Taxane containing regimens.

Appendix A

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0011 | vav 3 oncogene | 10451 | VAV3; VAV3 ONCOGENE; ONCOGENE VAV3; vav 3 oncogene | TEESINDEDIY KGLPDLIDE (1) | EKRTNGLR RTPKQVD (2) | DYISKSKED VKLK (3) | 1:90- 1:300 |
| S0017 | WAP four-disulfide core domain 2 | 10406 | WFDC2; WAP5; dJ461P17.6; major epididymis-specific protein E4; epididymal secretory protein E4; WAP four-disulfide core domain 2; WAP domain containing protein HE4-V4; epididymis-specific, whey-acidic protein type, four-disulfide core WAP four-disulfide | EKTGVCPELQ ADQNCTQE (4) | PNDKEGSC PQVNIN (5) | RDQCQVDT QCPGQMK (6) | 1:25- 1:500 |
| S0018 | secretoglobin, family 2A, member 2 | 4250 | UGB2; MGB1; SCGB2A2; mammaglobin 1; secretoglobin, family 2A, member 2 | SKTINPQVSK TEYKELLQE (7) | DDNATTNAI DELKEC (8) | NQTDETLSN VEVFMQ (9) | 1:300- 1:1000 |
| S0020 | PPAR binding protein | 5469 | RB18A; TRIP2; PPARGBP; PBP; CRSP1; PPARBP; CRSP200; DRIP230; PPAR-BINDING PROTEIN; PPARG binding protein; PPAR binding protein; CRSP, 200-KD SUBUNIT; PEROXISOME PROLIFERATOR-ACTIVATED RECEPTOR-BINDING | SSDDGIRPLP EYSTEKHKK (10) | DGKSKDKP PKRKKADTE (11) | NKTKKKKSS RLPPEK (12) | 1:100 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | | | PROTEIN; THYROID HORMONE RECEPTOR INTERACTOR 2; RECOGN | | | | |
| S0021 | hypothetical protein FLJ23834 | 222256 | FLJ23834; hypothetical protein FLJ23834 | KNKEPLTKKG ETKTAERD (13) | KLTCTDLDS SPRSFRYS (14) | EVDYENPS NLAAGNKYT (15) | 1:200- 1:2500 |
| S0022 | cytochrome P450 4Z1 | 199974 | CYP4Z1; cytochrome P450 4Z1; cytochrome P450, family 4, sub-family Z, polypeptide 1 | KTLQVFNPLR FSRENSEKIH (16) | QHFAIIECKV AVALT (17) | RKFLAPDHS RPPQPVRQ (18) | 1:50- 1:500 |
| S0024 | RAS-like, estrogen-regulated, growth-inhibitor | 85004 | RERG; RAS-like, estrogen-regulated, growth-inhibitor | MAKSAEVKLA IFGRAGVGK (19) | VLPLKNILDE IKKPKN (20) | YELCREVRR RRMVQGKT (21) | 1:900- 1:2700 |
| S0032 | fatty acid binding protein 3, muscle and heart (mammary-derived growth inhibitor) | 2170 | MDGI; O-FABP; FABP3; FABP11; H-FABP; FATTY ACID-BINDING PROTEIN, SKELETAL MUSCLE; Fatty acid-binding protein 3, muscle; fatty acid binding protein 11; FATTY ACID-BINDING PROTEIN, MUSCLE AND HEART; fatty acid binding protein 3, muscle and heart (mammary-de | TKPTTIIEKNG DILTLKTH (22) | KNTEISFKL GVEFDE (23) | HLQKWDGQ ETTLVRE (24) | 1:225 |
| S0036 | gamma-aminobutyric acid (GABA) A receptor, pi | 2568 | GABRP; GAMMA-AMINOBUTYRIC ACID RECEPTOR, PI; GABA-A RECEPTOR, PI POLYPEPTIDE; gamma-aminobutyric acid (GABA) A receptor, pi | DGNDVEFTW LRGNDSVRG LEH (25) | LQQMAAKD RGTTKEVEE VS (26) | KRKISFASIE ISSDNVDYS D (27) | 1:250- 1:500 |
| S0037 | annexin A8 | 244 | ANX8; ANXA8; annexin VIII; annexin A8 | QRQQIAKSFK AQFGKDLTE (28) | REIMKAYEE DYGSSLEED IQ (29) | EEYEKIANK SIEDSIKSE (30) | 1:30- 1:40 |
| S0039 | CDNA FLJ25076 fis, clone CBL06117 | 134111 | similar to 3110006E14Rik protein; CDNA FLJ25076 fis, clone CBL06117 | EGGSLVPAA RQQHCTQVR SRR (31) | RKAGKSKK SFSRKEAE (32) | KTHEKYGW VTPPVSDG (33) | 1:50- 1:30000 |
| S0040 | ATP-binding cassette, sub-family B (MDR/TAP), member 1 | 5243 | P-gp; PGY1; CLCS; ABCB1; ABC20; CD243; GP170; MDR1; doxorubicin resistance; colchicin sensitivity; P-GLYCOPROTEIN 1; multidrug resistance 1; P glycoprotein 1; ATP-binding cassette sub-family B member 1; ATP-BINDING CASSETTE, SUBFAMILY B, MEMBER 1; ATP-bin | MDLEGDRNG GAKKKN (34) | NLEDLMSNI TNRSDINDT G (35) | RGSQAQDR KLSTKEA (36) | 1:200- 1:400 |
| S0041 | ATP-binding cassette, sub-family B (MDR/TAP), member 4 | 5244 | MDR3; PGY3; PFIC-3; ABCB4; ABC21; MDR2/3; P-GLYCOPROTEIN 3; MULTIDRUG RESISTANCE 3; P-glycoprotein-3/multiple drug resistance-3; P glycoprotein 3/multiple drug resistance 3; ATP-binding cassette, sub-family B (MDR/TAP), member 4; ATP-binding cassette, sub | MDLEAAKNG TAWRPTSAE (37) | NFSFPVNFS LSLLNPGK (38) | KNSQMCQK SLDVETDG (39) | 1:60- 1:300 |
| S0042 | ATP-binding cassette, sub-family C (CFTR/MRP), member 1 | 4363 | ABCC1; MRP1; GS-X; ABC29; multidrug resistance protein; MULTIDRUG RESISTANCE-ASSOCIATED PROTEIN 1; multiple drug resistance-associated protein; multiple drug resistance protein 1; ATP-BINDING CASSETTE, SUBFAMILY C, MEMBER 1; ATP-binding cassette, sub-fami | MALRGFCSA DGSD (40) | KNWKKECA KTRKQPVK (41) | DSIERRPVK DGGGTNS (42) | 1:40- 1:500 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0043 | ATP-binding cassette, sub-family C (CFTR/MRP), member 2 | 1244 | MRP2; cMRP; CMOAT; ABCC2; ABC30; DJS; MULTIDRUG RESISTANCE-ASSOCIATED PROTEIN 2; canalicular multispecific organic anion transporter; MULTISPECIFIC ORGANIC ANION TRANSPORTER, CANALICULAR; ATP-BINDING CASSETTE, SUBFAMILY C, MEMBER 2; ATP-binding cassette, | MLEKFCNSTF WNSSFLDSP E (43) | SILCGTFQF QTLIRT (44) | ENNESSNN PSSIAS (45) | 1:50- 1:333 |
| S0044 | ATP-binding cassette, sub-family C (CFTR/MRP), member 4 | 10257 | MOAT-B; MRP4; MOATB; ABCC4; EST170205; MULTIDRUG RESISTANCE-ASSOCIATED PROTEIN 4; MULTISPECIFIC ORGANIC ANION TRANSPORTER B; ATP-binding cassette, sub-family C, member 4; ATP-BINDING CASSETTE, SUBFAMILY C, MEMBER 4; ATP-binding cassette, sub-family C (CFT | QEVKPNPLQ DANICSR (46) | DEISQRNRQ LPSDGKK (47) | VQDFTAFW DKASETPTL Q (48) | 1:20- 1:100 |
| S0045 | ATP-binding cassette, sub-family C (CFTR/MRP), member 3 | 8714 | MOAT-D; ABC31; MLP2; ABCC3; E5T90757; cMOAT2; MULTIDRUG RESISTANCE-ASSOCIATED PROTEIN 3; canicular multispecific organic anion transporter; CANALICULAR MULTISPECIFIC ORGANIC ANION TRANSPORTER 2; ATP-BINDING CASSETTE, SUBFAMILY C, MEMBER 3; ATP-binding cas | MDALCGSGE LGSKFWDSN (49) | RKQEKQTA RHKASAA (50) | DPQSVERK TISPG (51) | 1:2000 |
| S0046 | ATP-binding cassette, sub-family C (CFTR/MRP), member 5 | 10057 | MOAT-C; ABCC5; MRP5; EST277145; ABC33; SMRP; pABC11; MOATC; MULTIDRUG RESISTANCE-ASSOCIATED PROTEIN 5; canalicular multispecific organic anion transporter C; ATP-binding cassette, sub-family C, member 5; ATP-BINDING CASSETTE, SUBFAMILY C, MEMBER 5; ATP-bi | MKDIDIGKEYI IPSPGYRS (52) | RDREDSKF RRTRPLEC QD (53) | SKHESSDV NCRRLER (54) | 1:100- 1:450 |
| S0047 | ATP-binding cassette, sub-family C (CFTR/MRP), member 6 | 368 | MRP6; ARA; E5T349056; MOATE; PXE; MLP1; ABC34; ANTHRACYCLINE RESISTANCE-ASSOCIATED PROTEIN; MULTIDRUG RESISTANCE-ASSOCIATED PROTEIN 6; ATP-binding cassette, sub-family C, member 6; ATP-BINDING CASSETTE, SUBFAMILY C, MEMBER 6; ATP-binding cassette, | MAAPAEPCA GQGVWNQTE PE (55) | DPGVVDSS SSGSAAGK D (56) | HTLVAENAM NAEK (57) | 1:50 |
| S0048 | ATP-binding cassette, sub-family B (MDR/TAP), member 11 | 8647 | BSEP; ABCB11; PFIC-2; SPGP; PGY4; PFIC2; ABC16; SISTER OF P-GLYCOPROTEIN; bile salt export pump; progressive familial intrahepatic cholestasis 2; ABC member 16, MDR/TAP subfamily; ATP-BINDING CASSETTE, SUBFAMILY B, MEMBER 11; ATP-binding cassette, sub-fam | MSDSVILRSIK KFGEEND (58) | TNSSLNQN MTNGTR (59) | QEVLSKIQH GHTIIS (60) | 1:600 |
| S0049 | ATP-binding cassette, sub-family B (MDR/TAP), member 10 | 23456 | MTABC2; E5T20237; MABC2; M-ABC2; ABCB10; MITOCHONDRIAL ABC PROTEIN 2; ATP-BINDING CASSETTE, SUBFAMILY B, MEMBER 10; ATP-binding cassette, sub-family B, member 10; ATP-binding cassette, sub-family B (MDR/TAP), member 10 | GADDPSSVT AEEIQR (61) | NAVASPEFP PRFNT (62) | KPNGIYRKL MNKQSFISA (63) | 1:10- 1:25 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0050 | transporter 1, ATP-binding cassette, sub-family B (MDR/TAP) | 6890 | RING4; ABC17; D6S114E; ABCB2; TAP1; APT1; PEPTIDE TRANSPORTER PSF1; TRANSPORTER, ABC, MHC, 1; ABC transporter, MHC 1; antigen peptide transporter 1; peptide supply factor 1; ABC TRANSPORTER, MHC, 1; ATP-BINDING CASSETTE, SUBFAMILY B, MEMBER 2; TRANSPORTER | MASSRCPAP RGCR (64) | QGGSGNPV RR (65) | EFVGDGIYN NTMGHVHS (66) | 1:80 |
| S0052 | ATP-binding cassette, sub-family C (CFTR/MRP), member 8 | 6833 | SUR1; MRP8; PHHI; ABC36; ABCC8; HRINS; sulfonylurea receptor (hyperinsulinemia); SULFONYLUREA RECEPTOR, BETA-CELL HIGH-AFFINITY; ATP-binding cassette, sub-family C, member 8; ATP-BINDING CASSETTE, SUBFAMILY C, MEMBER 8; ATP-binding cassette, sub-family C | MPLAFCGSE NHSAAYR (67) | DHLGKEND VFQPKTQFL G (68) | EIREEQCAP HEPTPQG (69) | 1:25-1:150 |
| S0053 | ATP-binding cassette, sub-family C (CFTR/MRP), member 9 | 10060 | ABCC9; ABC37; sulfonylurea receptor 2A; ATP-BINDING CASSETTE, SUBFAMILY C, MEMBER 9; ATP-binding cassette, sub-family C (CFTR/MRP), member 9; ATP-binding cassette, sub-family C, member 9 isoform SUR2B; ATP-binding cassette, sub-family C, member 9 isoform | MSLSFCGNNI SS (70) | QRVNETQN GTNNTTGIS E (71) | DEIGDDSW RTGESSLPF E (72) | 1:25-1:50 |
| S0055 | integral membrane protein 2B | 9445 | E25B; ABRI; E3-16; FBD; BRI2; BRICD2B; ITM2B; BRI GENE; BRICHOS domain containing 2B; integral membrane protein 2B | MVKVTFNSAL AQKEAKKDE PK (73) | QTIEENIKIF EEEEVE (74) | HDKETYKLQ RRETIKGIQ KRE (75) | 1:450-1:500 |
| S0057 | ankyrin 3, node of Ranvier (ankyrin G) | 288 | ankyrin-G; ANK3; ankyrin-3, node of Ranvier; ankyrin 3 isoform 1; ankyrin 3 isoform 2; ankyrin 3, node of Ranvier (ankyrin G) | MAHAASQLK KNRDLEINAE E (76) | HKKETESD QDDEIEKTD RRQ (77) | EGFKVKTKK EIRHVEKKS HS (78) | 1:750 |
| S0058 | hypothetical protein FLJ21918 | 80004 | FLJ21918; hypothetical protein FLJ21918 | ERALAAAQR CHKKVMKER (79) | TAGMKDLLS VFQAYQ (80) | DPPRTVLQA PKEWVCL (81) | 1:20 |
| S0059 | tripartite motif-containing 29 | 23650 | ATDC; TRIM29; tripartite motif-containing 29; ataxia-telangiectasia group D-associated protein; tripartite motif protein TRIM29 isoform alpha; tripartite motif protein TRIM29 isoform beta | MEAADASRS NGSSPEARD AR (82) | ELHLKPHLE GAAFRDHQ (83) | EGEGLGQS LGNFKDDLL N (84) | 1:50-1:3000 |
| S0059P2 | tripartite motif-containing 29 | 23650 | ATDC; TRIM29; tripartite motif-containing 29; ataxia-telangiectasia group D-associated protein; tripartite motif protein TRIM29 isoform alpha; tripartite motif protein TRIM29 isoform beta | ELHLKPHLEG AAFRDHQ (85) | N/A | N/A | 1:30-1:90 |
| S0063 | iroquois homeobox protein 3 | 79191 | IRX3; iroquois homeobox protein 3 | GSEERGAGR GSSGGREE (86) | KIWSLAETA TSPDNPRR S (87) | KKLLKTAFQ PVPRRPQN HLD (88) | 1:200-1:1200 |
| S0068 | RAS-like, estrogen-regulated, growth-inhibitor | 85004 | RERG; RAS-like, estrogen-regulated, growth-inhibitor | RRSSTTHVK QAINKMLTKIS S (89) | N/A | N/A | 1:500-1:40000 |
| S0070 | G protein-coupled receptor 160 | 26996 | GPCR150; GPR160; putative G protein-coupled receptor; G protein-coupled receptor 160 | MRRKNTCQN FMEYFCISLA F (90) | NETILYFPFS SHSSYTVRS KK (91) | KVQIPAYIE MNIPLVILCQ (92) | 1:10-1:100 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0072 | S100 calcium binding protein A8 (calgranulin A) | 6279 | CP-10; L1Ag; CALPROTECTIN; 60B8AG; S100A8; MIF; CAGA; NIF; MRP8; MA387; CFAG; CGLA S100A8/S100A9 COMPLEX; cystic fibrosis antigen; S100 calcium-binding protein A8; S100 calcium binding protein A8 (calgranulin A) | MLTELEKALN SIIDVYHK (93) | RDDLKKLLE TECPQYIRK KGAD (94) | KMGVAAHK KSHEESHKE (95) | 1:6500-1:10000 |
| S0073 | forkhead box A1 | 3169 | HNF3A; MGC33105; TCF3A; FOXA1; forkhead box A1; HEPATOCYTE NUCLEAR FACTOR 3-ALPHA; hepatocyte nuclear factor 3, alpha | PESRKDPSG ASNPSADS (96) | HGLAPHES QLHLKGD (97) | EQQHKLDF KAYEQALQY S (98) | 1:100-1:2700 |
| S0073P2 | forkhead box A1 | 3169 | HNF3A; MGC33105; TCF3A; FOXA1; forkhead box A1; HEPATOCYTE NUCLEAR FACTOR 3-ALPHA; hepatocyte nuclear factor 3, alpha | HGLAPHESQ LHLKGD (99) | N/A | N/A | 1:50-1:450 |
| S0074 | trefoil factor 3 (intestinal) | 7033 | TFF3; trefoil factor 3 (intestinal); trefoil factor 3, HITF, human intestinal trefoil factor | EEYVGLSAN QCAVPAKDR VD (100) | RVDCGYPH VTPKECN (101) | VPWCFKPL QEAECTF (102) | 1:2500-1:30000 |
| S0074P3 | trefoil factor 3 (intestinal) | 7033 | TFF3; trefoil factor 3 (intestinal); trefoil factor 3, HITF, human intestinal trefoil factor | VPWCFKPLQ EAECTF (103) | N/A | N/A | 1:400-1:810 |
| S0076x1 | keratin 17 | 3872 | PC2; PCHC1; KRT17; K17; CYTOKERATIN 17; keratin 17 | KKEPVTTRQV RTIVEE (104) | QDGKVISSR EQVHQTTR (105) | SSSIKGSSG LGGGSS (106) | 1:200 |
| S0078 | kynureninase (L-kynurenine hydrolase) | 8942 | 3.7.1.3; XANTHURENICACIDURIA; KYNU; HYDROXYKYNURENINURIA; KYNURENINASE DEFICIENCY; XANTHURENIC ACIDURIA; kynureninase (L-kynurenine hydrolase) | DEEDKLRHFR ECFYIPKIQD (107) | KPREGEETL RIEDILEVIE KE (108) | EERGCQLTI TFSVPNKDV FQE (109) | 1:180-1:200 |
| S0079 | solute carrier family 39 (zinc transporter), member 6 | 25800 | SLC39A6; LIV-1 protein, estrogen regulated; solute carrier family 39 (zinc transporter), member 6; solute carrier family 39 (metal ion transporter), member 6 | DHNHAASGK NKRKALCPD HD (110) | EEPAMEMK RGPLFSHLS SQNI (111) | QRYSREELK DAGVATL (112) | 1:200-1:800 |
| S0081 | N-acetyltransferase 1 (arylamine N-acetyltransferase) | 9 | AAC1; 2.3.1.5; NAT1; arylamine N-acetyltransferase-1; ACETYL-CoA: ARYLAMINE N-ACETYLTRANSFERASE; ARYLAMINE N-ACETYLTRANSFERASE 1; N-acetyltransferase 1 (arylamine N-acetyltransferase); arylamide acetylase 1 (N-acetyltransferase 1) | MDIEAYLERI GYKKSRNKL DLE (113) | QMWQPLELI SGKDQPQV PCVFR (114) | FNISLQRKL VPKHGDRF FTI (115) | 1:10-1:240 |
| S0086 | X-box binding protein 1 | 7494 | XBP2; TREB5; XBP1; X-box-binding protein-1; X BOX-BINDING PROTEIN 1; X BOX-BINDING PROTEIN 2; X-box binding protein 1 | RQRLTHLSPE EKALRRKLKN R (116) | EKTHGLVVE NQELRQRL GMD (117) | QPPFLCQW GRHQPSWK PLMN (118) | 1:180-1:400 |
| S0088 | claudin 10 | 9071 | CPETRL3; OSP-L; CLDN10; claudin 10; claudin 10 isoform a; claudin 10 isoform b | NKITTEFFDPL FVEQK (119) | FSISDNNKT PRYTYNGAT (120) | EDFKTTNPS KQFDKNAY V (121) | 1:333-1:1000 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0090 | sparc/osteonectin, cwcv and kazal-like domains proteoglycan (testican) 2 | 9806 | KIAA0275; testican-2; SPOCK2; TESTICAN 2; SPARC/OSTEONECTIN, CWCV, AND KAZAL-LIKE DOMAINS PROTEOGLYCAN 2; sparc/osteonectin, cwcv and kazal-like domains proteoglycan (testican) 2 | EGDAKGLKE GETPGNFME DE (122) | EWCFCFWR EKPPCLAEL ER (123) | EEEGEAGE ADDGGYIW (124) | 1:100-1:800 |
| S0091 | lipocalin 2 (oncogene 24p3) | 3934 | UTEROCALIN; NGAL; LCN2; NEUTROPHIL GELATINASE-ASSOCIATED LIPOCALIN; ONCOGENIC LIPOCALIN 24P3; lipocalin 2 (oncogene 24p3) | DKDPQKMYA TIYE (125) | KKCDYWIRT FVPGCQ (126) | ENFIRESKY LGLPEN (127) | 1:100 |
| S0092 | paired box gene 8 | 7849 | PAX8; paired box gene 8; paired box gene 8 isoform PAX8C; paired box gene 8 isoform PAX8D; paired box gene 8 isoform PAX8E; paired box gene 8 isoform PAX8A; paired box gene 8 isoform PAX8B; PAIRED DOMAIN GENE 8 PAX8/PPARG FUSION GENE | DDSDQDSCR LSIDSQ (128) | RQHYPEAY ASPSHTK (129) | NTPLGRNLS THQTYPVVA D (130) | 1:30-1:100 |
| S0093 | mesothelin | 10232 | CAK1; SMR; MSLN; mesothelin; MEGAKARYOCYTE-POTENTIATING FACTOR; SOLUBLE MPF/MESOTHELIN-RELATED PROTEIN; mesothelin isoform 2 precursor; mesothelin isoform 1 precursor; megakaryocyte potentiating factor precursor; ANTIGEN RECOGNIZED BY MONOCLONAL ANTIBODY | RLVSCPGPLD QDQQE (131) | KMSPEDIRK WNVTSLETL K (132) | SPEELSSVP PSSIWAVRP QD (133) | 1:500 |
| S0094 | kallikrein 6 (neurosin, zyme) | 5653 | Bssp; PRSS18; KLK6; Klk7; SP59; PRSS9; MGC9355; protease M; kallikrein 6 preproprotein; protease, serine, 18; protease, serine, 9; kallikrein 6 (neurosin, zyme) | EEQNKLVHG GPCDKTSH (134) | ELIQPLPLER DCSANT (135) | GKTADGDF PDTIQC (136) | 1:150-1:300 |
| S0095 | Rap guanine nucleotide exchange factor (GEF) 3 | 10411 | bcm910; MGC21410; 9330170P05Rik; EPAC; RAPGEF3; cAMP-GEFI; RAP guanine-nucleotide-exchange factor 3; EXCHANGE PROTEIN ACTIVATED BY cAMP; RAP guanine-nucleotide-exchange factor (GEF) 3; cAMP-REGULATED GUANINE NUCLEOTIDE EXCHANGE FACTOR I; RAP GUANINE NUCLE | REQWPERRR CHRLENGCG NA (137) | KVNSAGDAI GLQPDAR (139) | QQLKVIDNQ RELSRLSRE LE (140) | 1:250-1:1000 |
| S0096 | ATPase, H+ transporting, lysosomal 56/58 kDa, V1 subunit B, isoform 1 (Renal tubular acidosis with deafness) | 525 | Vma2; VPP3; ATP6V1B1; RTA1B; 3.6.3.14; VATB; ATP6B1; V-ATPase B1 subunit; H+-ATPase beta 1 subunit; H(+)-transporting two-sector ATPase, 58 kD subunit; vacuolar proton pump, subunit 3; endomembrane proton pump 58 kDa subunit; ATPase, H+ transporting, lysos | REHMQAVTR NYITHPR (141) | KKSKAVLDY HDDN (142) | DEFYSREG RLQDLAPDT AL (143) | 1:100-1:800 |
| S0097 | frizzled homolog 8 (Drosophila) | 8325 | FZ-8; hFZ8; FZD8; frizzled 8; frizzled homolog 8 (Drosophila); FRIZZLED, DROSOPHILA, HOMOLOG OF, 8 | KQQDGPTKT HKLEKLMIR (144) | ELRVLSKAN AIVPGLSGG E (145) | RRGGEGGE ENPSAAKG HLMG (146) | 1:100-1:500 |
| S0099 | histone 1, H2ba | 255626 | HIST1H2BA; histone 1, H2ba | MPEVSSKGA TISKK (147) | GFKKAVVKT QK (148) | KEGKKRKR TRKE (149) | 1:333-1:500 |
| S0110 | hypothetical protein MGC2714 | 84259 | MGC2714; hypothetical protein MGC2714 | RYAFDFARDK DQRSLDID (150) | SVFYQYLEQ SKYRVMNK DQ (151) | EDGAWPVL LDEFVEWQ KVRQTS (152) | 1:500-1:2500 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0117 | reproduction 8 | 7993 | D8S2298E; REP8; reproduction 8; Reproduction/chromosome 8 | SFKSPQVYLK EEEEKNEKR (153) | RKKQQEAQ GEKASRYIE (154) | EDIGITVDTV LILEEKEQT N (155) | 1:200-1:375 |
| S0119 | slit homolog 1 (Drosophila) | 6585 | SLIT3; MEGF4; SLIL1; Slit-1; SLIT1; slit homolog 1 (Drosophila); SLIT, DROSOPHILA, HOMOLOG OF, 1; MULTIPLE EPIDERMAL GROWTH FACTOR-LIKE DOMAINS 4 | KAFRGATDLK NLRLDKNQ (156) | DERCEEGQ EEGGCLPR PQ (157) | DGTSFAEEV EKPTKCGC ALCA (158) | 1:900 |
| S0122 | leucyl-tRNA synthetase 2, mitochondrial | 23395 | 6.1.1.4; MGC26121; KIAA0028; LEURS; LARS2; leucine translase; leucine-tRNA ligase; LEUCYL-tRNA SYNTHETASE, MITOCHONDRIAL; leucyl-tRNA synthetase 2, mitochondrial; leucyl-tRNA synthetase 2, mitochondrial precursor | QRIKEQASKI SEADKSKPKF (159) | HAKTKEKLE VTWEKMSK SKHN (160) | KSPQPQLLS NKEKAEARK (161) | 1:150 |
| S0123 | homeo box D4 | 3233 | HOX4B; HOXD4; HHO.C13; HOX-5.1; HOMEOBOX D4; HOMEOBOX 4B; HOMEOBOX X; homeo box D4; homeobox protein Hox-D4; Hox-4.2, mouse, homolog of homeo box X | MLFEQGQQA LELPECT (162) | KDQKAKGIL HSPASQSP ERS (163) | HSSQGRLP EAPKLTHL (164) | 1:100-1:500 |
| S0124 | sphingosine-1-phosphate lyase 1 | 8879 | KIAA1252; SPL; SGPL1; sphingosine-1-phosphate lyase 1 | KRGARRGGW KRKMPSTDL (165) | KIVRVPLTK MMEVDVR (166) | QFLKDIRES VTQIMKNPK A (167) | 1:990-1:1500 |
| S0126 | HBxAg transactivated protein 1 | 55789 | XTP1; HBxAg transactivated protein 1 | SKQGVVILDD KSKELPHW (168) | VQTFSRCIL CSKDEVDLD EL (169) | LKKPFQPFQ RTRSFRM (170) | 1:450-1:1600 |
| S0132 | SRY (sex determining region Y)-box 9 (campomelic dysplasia autosomal sex-reversal) | 6662 | SRA1; CMD1; CMPD1; SOX9; SRY-BOX 9; transcription factor SOX9; SRY-RELATED HMG-BOX GENE 9; SEX REVERSAL, AUTOSOMAL, 1; SRY (sex-determining region Y)-box 9 protein; SRY (sex-determining region Y)-box 9 (campomelic dysplasia, autosomal sex-reversal); SRY ( | MNLLDPFMK MTDEQEKGL S (171) | NTFPKGEPD LKKESEEDK (172) | KNGQAEAE EATEQTHIS PN (173) | 1:100 - 1:500 |
| S0137 | cadherin, EGF LAG seven-pass G-type receptor 2 (flamingo homolog, Drosophila) | 1952 | Flamingo1; CELSR2; EGFL2; KIAA0279; MEGF3; CDHF10; EGF-like-domain, multiple 2; epidermal growth factor-like 2; multiple epidermal growth factor-like domains 3; cadherin EGF LAG seven-pass G-type receptor 2; cadherin, EGF LAG seven-pass G-type receptor 2 | QASSLRLEPG RANDGDWH (174) | ELKGFAERL QRNESGLD SGR (175) | RSGKSQPS YIPFLLREE (176) | 1:1800-1:5000 |
| S0139 | gamma-glutamyl hydrolase (conjugase, folylpolygamma-glutamyl hydrolase) | 8836 | 3.4.19.9; GGH; gamma-glutamyl hydrolase precursor; gamma-glutamyl hydrolase (conjugase, folylpolygammaglutamyl hydrolase) | RRSDYAKVA KIFYNLSIQSF DD (177) | KNFTMNEKL KKFFNVLTT N (178) | EFFVNEARK NNHHFKSE SEE (179) | 1:2500-1:30000 |
| S0140 | bullous pemphigoid antigen 1, 230/240 kDa | 667 | BP240; FLJ13425; FLJ32235; FLJ21489; FLJ30627; CATX-15; KIAA0728; BPAG1; dystonin; hemidesmosomal plaque protein; bullous pemphigoid antigen 1, 230/240 kDa; bullous pemphigoid antigen 1 (230/240 kD); bullous pemphigoid antigen 1 isoform 1eA precursor; bullo | KNTQAAEALV KLYETKLCE (180) | QENQPENS KTLATQLNQ (181) | KQMEKDLA FQKQVAEK QLK (182) | 1:250-1:20000 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0143 | fatty acid synthase | 2194 | 2.3.1.85; OA-519; FASN; MGC14367; MGC15706; fatty acid synthase | EFVEQLRKEG VFAKEVR (183) | DRHPQALE AAQAELQQ HD (184) | REVRQLTLR KLQELSSKA DE (185) | 1:5000-1:30000 |
| S0143P3 | fatty acid synthase | 2194 | 2.3.1.85; OA-519; FASN; MGC14367; MGC15706; fatty acid synthase | REVRQLTLRK LQELSSKADE (186) | N/A | N/A | 1:200-1:630 |
| S0144 | matrix metalloproteinase 14 (membrane-inserted) | 4323 | MMP-X1; 3.4.24.-; MMP14; MTMMP1; MT1-MMP; membrane-type-1 matrix metalloproteinase; matrix metalloproteinase 14 preproprotein; MATRIX METALLOPROTEINASE 14, MEMBRANE-TYPE; matrix metalloproteinase 14 (membrane-inserted); membrane-type matrix metalloprotein | AYIREGHEKQ ADIMIFFAE (187) | DEASLEPGY PKHIKELGR (188) | RGSFMGSD EVFTYFYK (189) | 1:500-1:20000 |
| S0147 | cystatin A (stefin A) | 1475 | STF1; CSTA; STFA; cystatin AS; cystatin A (stefin A) | MIPGGLSEAK PATPEIQEIV (190) | NETYGKLEA VQYKTQ (191) | DLVLTGYQV DKNKDDELT GF (192) | 1:100-1:5000 |
| S0149 | transient receptor potential cation channel, subfamily V, member 6 | 55503 | TRPV6; ECAC2; CAT1; CATL; CALCIUM TRANSPORTER 1; CALCIUM TRANSPORTER-LIKE PROTEIN; EPITHELIAL CALCIUM CHANNEL 2 transient receptor potential cation channel, subfamily V, member 6 | RQEHCMSEH FKNRPACLGA R (193) | QGHKWGES PSQGTQAG AGK (194) | RACGKRVS EGDRNGSG GGKWG (195) | 1:400-1:20000 |
| S0156 | fatty acid binding protein 7, brain | 2173 | B-FABP; FABP7; FABPB; MRG; mammary-derived growth inhibitor-related; FATTY ACID-BINDING PROTEIN 7; FATTY ACID-BINDING PROTEIN, BRAIN; fatty acid binding protein 7, brain | MVEAFCATW KLTNSQN (196) | QVGNVTKP TVIISQE (197) | KVVIRTLSTF KNTE (198) | 1:100-1:20000 |
| S0158 | cadherin 3, type 1, P-cadherin (placental) | 1001 | CDHP; HJMD; PCAD; CDH3; placental cadherin; CADHERIN, PLACENTAL; cadherin 3, P-cadherin (placental); calcium-dependent adhesion protein, placental; cadherin 3, type 1 preproprotein; cadherin 3, type 1, P-cadherin (placental) | RAVFREAEVT LEAGGAEQE (199) | QEPALFSTD NDDFTVRN (200) | QKYEAHVP ENAVGHE (201) | 1:150-1:2000 |
| S0165 | chemokine (C-X-C motif) ligand 1 (melanoma growth stimulating activity, alpha) | 2919 | MGSA-a; NAP-3; CXCL1; SCYB1; GROa; GRO1, FORMERLY; GRO PROTEIN, ALPHA; GRO1 ONCOGENE, FORMERLY; MELANOMA GROWTH STIMULATORY ACTIVITY, ALPHA; GRO1 oncogene (melanoma growth-stimulating activity); CHEMOKINE, CXC MOTIF, LIGAND 1; GRO1 oncogene (melanoma grow | KKIIEKMLNSD KSN (202) | N/A | N/A | 1:100-1:500 |
| S0171 | baculoviral IAP repeat-containing 5 (survivin) | null | BIRC5; baculoviral IAP repeat-containing 5 (survivin) | GKPGNQNSK NEPPKKRER ER (203) | QAEAPLVPL SRQNK (204) | NCFLTERKA QPDE (205) | 1:22500-1:30000 |
| S0193 | procollagen-lysine, 2-oxoglutarate 5-dioxygenase (lysine hydroxylase) 2 | 5352 | PLOD2; LYSYL HYDROXYLASE 2; LYSINE HYDROXYLASE 2 PROCOLLAGEN-LYSINE, 2-OXOGLUTARATE 5-DIOXYGENASE 2; procollagen-lysine, 2-oxoglutarate 5-dioxygenase (lysine hydroxylase) 2; procollagen-lysine, 2-oxoglutarate 5-dioxygenase (lysine hydroxylase) 2 isoform | EFDTVDLSAV DVHPN (206) | NKEVYHEK DIKVFFDKA K (207) | KQVDLENV WLDFIRE (208) | 1:20000 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0202 | PTK7 protein tyrosine kinase 7 | 5754 | PTK7; CCK4; protein-tyrosine kinase PTK7; colon carcinoma kinase-4; PTK7 protein tyrosine kinase 7; PTK7 protein tyrosine kinase 7 isoform e precursor; PTK7 protein tyrosine kinase 7 isoform a precursor; PTK7 protein tyrosine kinase 7 isoform d precursor; | LKKPQDSQLE EGKPGYLD (209) | KAKRLQKQ PEGEEPEM E (210) | KDRPSFSEI ASALGDSTV DSKP (211) | 1:500- 1:800 |
| S0211 | cytochrome P450, family 2, subfamily A, polypeptide 7 | 1549 | CYPIIA7; P450-IIA4; 1.14.14.1; CPA7; CYP2A7; CPAD; CYTOCHROME P450, SUBFAMILY IIA, POLYPEPTIDE 7; cytochrome P450, subfamily IIA (phenobarbital-inducible), polypeptide 7; cytochrome P450, family 2, subfamily A, polypeptide 7; cytochrome P450, family 2, su | KRGIEERIQE ESGFLIE (212) | DRVIGKNRQ PKFEDRTK (213) | NPQHFLDD KGQFKKSD (214) | 1:500- 1:2500 |
| S0218 | solute carrier family 29 (nucleoside transporters), member 4 | 222962 | SLC29A4; solute carrier family 29 (nucleoside transporters), member 4 | RHCILGEWLP ILIMAVFN (215) | KQRELAGN TMTVSYMS (216) | RNAHGSCL HASTANGSI LAGL (217) | 1:20- 1:50 |
| S0221 | solute carrier family 28 (sodium-coupled nucleoside transporter), member 2 | 9153 | HCNT2; SLC28A2; HsT17153; SPNT1; CONCENTRATIVE NUCLEOSIDE TRANSPORTER 2; SODIUM-DEPENDENT PURINE NUCLEOSIDE TRANSPORTER 1; solute carrier family 28 (sodium-coupled nucleoside transporter), member 2 | ELMEKEVEPE GSKRTD (218) | KARSFCKTH ARLFKK (219) | KNKRLSGM EEWIEGEK (220) | 1:500- 1:1200 |
| S0223 | angiopoietin-like 4 | 51129 | HFARP; FIAF; ANGPTL4; PGAR; angiopoietin-like 4; FASTING-INDUCED ADIPOSE FACTOR; PPARG ANGIOPOIETIN-RELATED PROTEIN; HEPATIC FIBRINOGENIANGIOPOIETIN-RELATED PROTEIN | EGSTDLPLAP ESRVDPE (221) | KVAQQQRH LEKQHLR (222) | DHKHLDHE VAKPARRK RLPE (223) | 1:30- 1:10000 |
| S0235 | carcinoembryonic antigen-related cell adhesion molecule 5 | 1048 | CEACAM5; CD66e; carcinoembryonic antigen-related cell adhesion molecule 5 | KLTIESTPFNV AEGKEC (224) | KSDLVNEEA TGQFRVYP ELPK (225) | KPVEDKDAV AFTCEPEAQ (226) | 1:500- 1:4500 |
| S0237 | podocalyxin-like | 5420 | podocalyxin-like; Gp200; PCLP; PODXL; PODOCALYXIN-LIKE PROTEIN; podocalyxin-like precursor | DEKLISLICRA VKATFNPAQD K (227) | KDKWDELK EAGVSDMK LGD (228) | DSWIVPLDN LTKDDLEE EDTHL (229) | 1:1000- 1:2000 |
| S0238 | xenotropic and polytropic retro virus receptor | 9213 | X3; XPR1; X RECEPTOR; SYG1, YEAST, HOMOLOG OF; xenotropic and polytropic retrovirus receptor | EAVVTNELED GDRQKAMKR LR (230) | RRYRDTKR AFPHLVNAG K (231) | KARDTKVLI EDTDDEANT (232) | 1:100- 1:500 |
| S0241 | glycyl-tRNA synthetase | 2617 | GlyRS; GARS; CMT2D; 6.1.1.14; SMAD1; GLYCYL-tRNA SYNTHETASE; glycine tRNA ligase; Charcot-Marie-Tooth neuropathy, neuronal type, D | RKRVLEAKEL ALQPKDDIVD (233) | RHGVSHKV DDSSGSIGR RYAR (234) | EARYPLFEG QETGKKETI EE (235) | 1:500- 1:7500 |
| S0244 | dachshund homolog 1 (Drosophila) | 1602 | DACH1; FLJ10138; dachshund homolog (Drosophila); DACHSHUND, DROSOPHILA, HOMOLOG OF; dachshund homolog 1 (Drosophila); dachshund homolog 1 isoform a; dachshund homolog 1 isoform b; dachshund homolog 1 isoform c | DLAGHDMGH ESKRMHIEKD E (236) | EKQVQLEKT ELKMDFLRE RE (237) | EADRSGGR TDAERTIQD GR (238) | 1:100- 1:3000 |
| S0251 | transcription factor CP2-like 2 | 29841 | TFCP2L2; LBP-32; MGR; GRHL1; mammalian grainyhead; LBP protein 32; transcription CP2- | EALYPQRRS YTSEDEAWK (239) | DYYKVPRE RRSSTAKPE VE (240) | DKYDVPHD KIGKIFKKCK K (241) | 1:5400 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | | | like 2; leader-binding protein 32 isoform 2; leader-binding protein 32 isoform 1 | | | | |
| S0253 | lysosomal associated protein transmembrane 4 beta | 55353 | LAPTM4B; lysosomal associated protein transmembrane 4 beta | DPDQYNFSS SELGGDFEF MDD (242) | EYIRQLPPN FPYRDD (243) | DTTVLLPPY DDATVNGA AKE (244) | 1:500- 1:2000 |
| S0255 | cyclin E2 | 9134 | CYCE2; CCNE2; cyclin E2; G1/S-specific cyclin E2; cyclin E2 isoform 2; cyclin E2 isoform 3; cyclin E2 isoform 1 | RREEVTKKH QYEIR (245) | KESRYVHD KHFEVLHSD LE (246) | DFFDRFMLT QKDINK (247) | 1:1000- 1:2000 |
| S0260 | nicastrin | 23385 | KIAA0253; nicastrin; NCSTN; APH2; ANTERIOR PHARYNX DEFECTIVE 2, C. ELEGANS, HOMOLOG OF | ESKHFTRDLM EKLKGRTSR (248) | ETDRLPRCV RSTARLAR (249) | ESRWKDIRA RIFLIASKEL E (250) | 1:2400- 1:5400 |
| S0265 | FXYD domain containing ion transport regulator 3 | 5349 | MAT-8; MAT8; PLML; FXYD3; phospholemman-like protein; MAMMARY TUMOR, 8-KD; FXYD domain-containing ion transport regulator 3; FXYD domain containing ion transport regulator 3; FXYD domain containing ion transport regulator 3 isoform 2 precursor; FXYD domai | KVTLGLLVFL AGFPPVLDAND LED (251) | SEWRSSGE QAGR (252) | KCKCKFGQ KSGHHPGE (253) | 1:400- 1:1200 |
| S0267 | immunoglobulin superfamily, member 3 | 3321 | EWI-3; V8; IGSF3; immunoglobin superfamily, member 3; immunoglobulin superfamily, member 3 | KVAKESDSVF VLKIYHLRQE D (254) | EREKTVTGE FIDKESKRP K (255) | KRAEDTAG QTALTVMRP D (256) | 1:200- 1:250 |
| S0270 | signal transducing adaptor molecule (SH3 domain and ITAM motif) 2 | 10254 | STAM2B; STAM2; DKFZp564C047; Hbp; STAM2A; SIGNAL-TRANSDUCING ADAPTOR MOLECULE 2; signal transducing adaptor molecule 2; STAM-like protein containing SH3 and ITAM domains 2; signal transducing adaptor molecule (SH3 domain and ITAM motif) 2 | KVARKVRALY DFEAVEDNE (257) | ETEVAAVDK LNVIDDDVE (258) | EIKKSEPEP VYIDEDKMD R (259) | 1:1000- 1:9000 |
| S0273 | dickkopf homolog 1 (Xenopus laevis) | 22943 | DKK1; DKK-1; SK; dickkopf-1 like; dickkopf (Xenopus laevis) homolog 1; dickkopf homolog 1 (Xenopus laevis); DICKKOPF, XENOPUS, HOMOLOG OF, 1 | DEECGTDEY CASPTRGGD (260) | RGEIEETITE SFGNDHSTL D (261) | N/A | 1:400- 1:500 |
| S0280 | solute carrier family 26, member 6 | 65010 | SLC26A6; solute carrier family 26, member 6 | MDLRRRDYH MERPLLNQE HLEE (262) | DTDIYRDVA EYSEAKE (263) | EFYSDALKQ RCGVDVDF LISQKKK (264) | 1:1800- 1:2400 |
| S0286 | WNT inhibitory factor 1 | 11197 | WIF1; WIF-1; WNT inhibitory factor 1; Wnt inhibitory factor-1 precursor | DAHQARVLIG FEEDILIVSE (265) | ERRICECPD GFHGPHCE K (266) | KRYEASLIH ALRPAGAQL R (267) | 1:90 |
| S0288 | preferentially expressed antigen in melanoma | 23532 | MAPE; PRAME; OPA-INTERACTING PROTEIN 4; Opa-interacting protein OIP4; preferentially expressed antigen in melanoma; melanoma antigen preferentially expressed in tumors | KRKVDGLSTE AEQPFIPVE (268) | KEGACDELF SYLIEKVKR KK (269) | DIKMILKMV QLDSIEDLE (270) | 1:1200 |
| S0295 | prostaglandin E synthase | 9536 | PGES; TP53112; MGST1L1; PP1294; PP102; PTGES; MGC10317; PIG12; MGST1-L1; MGST-IV; MGST1-like 1; p53-INDUCED GENE 12; prostaglandin E synthase; p53-induced apoptosis protein 12; prostaglandin E synthase isoform 2; prostaglandin E synthase isoform 1; micros | RLRKKAFANP EDALR (271) | RSDPDVER CLRAHRND (272) | RVAHTVAYL GKLRAPIR (273) | 1:100- 1:2400 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0296 | solute carrier family 7 (cationic amino acid transporter, y+ system), member 5 | 8140 | SLC7A5; MPE16; D16S469E; CD98; LAT1; 4F2 light chain; Membrane protein E16; L-TYPE AMINO ACID TRANSPORTER 1; Solute carrier family 7, member 5; solute carrier family 7 (cationic amino acid transporter, y+ system), member 5 | KRRALAAPAA EEKEEAR (274) | EAREKMLAA KSADGSAP AGE (275) | MIWLRHRKP ELERPIK (276) | 1:300- 1:5000 |
| S0296P 1 | solute carrier family 7 (cationic amino acid transporter, y+ system), member 5 | 8140 | SLC7A5; MPE16; D16S469E; CD98; LAT1; 4F2 light chain; Membrane protein E16; L-TYPE AMINO ACID TRANSPORTER 1; Solute carrier family 7, member 5; solute carrier family 7 (cationic amino acid transporter, y+ system), member 5 | KRRALAAPAA EEKEEAR (277) | N/A | N/A | 1:225- 1:3150 |
| S0297 | v-maf musculoaponeurotic fibrosarcoma oncogene homolog K (avian) | 7975 | FLJ32205; NFE2U; MAFK; NFE2, 18-KD SUBUNIT; nuclear factor erythroid-2, ubiquitous (p18); NUCLEAR FACTOR ERYTHROID 2, UBIQUITOUS SUBUNIT; v-maf musculoaponeurotic fibrosarcoma oncogene homolog K (avian); v-maf avian musculoaponeurotic fibrosarcoma oncogen | KPNKALKVKK EAGE (278) | KRVTQKEEL ERQRVELQ QEVEK (279) | RLELDALRS KYE (280) | 1:333- 1:800 |
| S0301 | signal peptide, CUB domain, EGF-like 2 | 57758 | SCUBE2; signal peptide, CUB domain, EGF-like 2 | KMHTDGRSC LEREDTVLEV TE (281) | KKGFKLLTD EKSCQDVD E (282) | KRTEKRLRK AIRTLRKAV HRE (283) | 1:3500- 1:5400 |
| S0303 | gamma-aminobutyric acid (GABA) A receptor, epsilon | 2564 | GABRE; GABA-A RECEPTOR, EPSILON POLYPEPTIDE; GAMMA-AMINOBUTYRIC ACID RECEPTOR, EPSILON; gamma-aminobutyric acid (GABA) A receptor, epsilon; gamma-aminobutyric acid (GABA) A receptor, epsilon isoform 2; gamma-aminobutyric acid (GABA) A receptor, epsilon is | RVEGPQTES KNEASSRD (284) | EETKSTETE TGSRVGKLP E (285) | KWENFKLEI NEKNSWKL FQFD (286) | 1:300- 1:500 |
| S0305 | S100 calcium binding protein A10 (annexin II ligand, calpactin I, light polypeptide (p11)) | 6281 | CAL1L; GP11; p10; 42C; S100A10; ANX2LG; CLP11; Ca[1]; CALPACTIN I, p11 SUBUNIT; ANNEXIN II, LIGHT CHAIN; CALPACTIN I, LIGHT CHAIN; S100 calcium-binding protein A10 (annexin II ligand, calpactin I, light polypeptide (p11)); S100 calcium binding protein A10 | DKGYLTKEDL RVLMEKE (287) | KDPLAVDKI MKDLDQCR DGK (288) | N/A | 1:8332- 1:24996 |
| S0311 | v-myb myeloblastosis viral oncogene homolog (avian)-like 2 | 4605 | MYBL2; MGC15600; MYB-RELATED GENE BMYB; MYB-related protein B; v-myb myeloblastosis viral oncogene homolog (avian)-like 2; V-MYB AVIAN MYELOBLASTOSIS VIRAL ONCOGENE HOMOLOG-LIKE 2 | MSRRTRCED LDELHYQDTD SD (289) | EEDLKEVLR SEAGIELIIE DDIR (290) | RRSPIKKVR KSLALDIVD ED (291) | 1:750- 1:5000 |
| S0312 | nucleoside phosphorylase | 4860 | NP; 2.4.2.1; nucleoside phosphorylase; PURINE-NUCLEOSIDE: ORTHOPHOSPHATE RIBOSYLTRANSFERASE; purine nucleoside phosphorylase; PNP NUCLEOSIDE PHOSPHORYLASE DEFICIENCY; ATAXIA WITH DEFICIENT CELLULAR IMMUNITY | EDYKNTAEW LLSHTKHR (292) | DERFGDRF PAMSDAYD RTMRQR (293) | KVIMDYESL EKANHEE (294) | 1:1000- 1:3600 |
| S0314 | chaperonin containing TCP1, subunit 5 (epsilon) | 22948 | KIAA0098; CCT5; chaperonin containing TCP1, subunit 5 (epsilon) | DQDRKSRLM GLEALKSHIM AAK (295) | KGVIVDKDF SHPQMPKK VED (296) | RMILKIDDIR KPGESEE (297) | 1:6000- 1:30000 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0315 | non-metastatic cells 1, protein (NM23A) expressed in | 4830 | GAAD; NME1; NDPKA; 2.7.4.6; NM23-H1; AWD NM23H1B; GZMA-ACTIVATED DNase; NUCLEOSIDE DIPHOSPHATE KINASE-A; AWD, DROSOPHILA, HOMOLOG OF; METASTASIS INHIBITION FACTOR NM23; nucleoside-diphosphate kinase 1 isoform b; NONMETASTATIC PROTEIN 23, HOMOLOG 1; nucleo | RLQPEFKPKQ LEGTMANCE R (298) | KFMQASED LLKEHYVDL KDR (299) | DSVESAEKE IGLWFHPEE LVD (300) | 1:9000-1:18000 |
| S0316 | squalene epoxidase | 6713 | SQLE; 1.14.99.7; squalene epoxidase; squalene monooxygenase | KSPPESENKE QLEARRRR (301) | RDGRKVTVI ERDLKEPDR (302) | DHLKEPFLE ATDNSHLR (303) | 1:1000-1:10000 |
| S0319 | pregnancy-induced growth inhibitor | 29948 | OKL38; pregnancy-induced growth inhibitor; PREGNANCY-INDUCED GROWTH INHIBITOR OKL38 | DLEVKDWMQ KKRRGLRNS R (304) | EYHKVHQM MREQSILSP SPYEGYR (305) | RHQLLCFKE DCQAVFQD LEGVEK (306) | 1:900 |
| S0326 | mal, T-cell differentiation protein 2 | 114569 | MAL2; mal, T-cell differentiation protein 2 | GPDILRTYSG AFVCLE (307) | CSLGLALRR WRP (308) | N/A | 1:120-1:1200 |
| S0330 | aldo-keto reductase family 1, member C 1/2 (dihydrodiol dehydrogenase 1; 20-alpha (3-alpha)-hydroxysteroid dehydrogenase) | 1645 | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol | RYLTLDIFAG PPNYPFSDEY (309) | N/A | N/A | 1:2500-1:75000 |
| S0330-x1 | aldo-keto reductase family 1, member C 1/2 (dihydrodiol dehydrogenase 1; 20-alpha (3-alpha)-hydroxysteroid dehydrogenase) | 1645 | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol | RYLTLDIFAG PPNYPFSDEY (310) | N/A | N/A | 1:600 |
| S0331 | aldo-keto reductase family 1, member C3 (3-alpha hydroxysteroid dehydrogenase, type II) | 8644 | HA1753; 1.1.1.188; DD3; hIuPGFS; HSD17B5; 1.3.1.20; 1.1.1.213; AKR1C3; KIAA0119; HAKRB; HAKRe; trans-1,2-dihydrobenzene-1,2-diol dehydrogenase; chlordecone reductase homolog; dihydrodiol dehydrogenase 3; prostaglandin F synthase; ALDO-KETO REDUCTASE B; 3- | HYFNSDSFAS HPNYPYSDE Y (311) | N/A | N/A | 1:300-1:999 |
| S0331-x1 | aldo-keto reductase family 1, member C3 (3-alpha hydroxysteroid dehydrogenase, type II) | 8644 | HA1753; 1.1.1.188; DD3; hIuPGFS; HSD17B5; 1.3.1.20; 1.1.1.213; AKR1C3; KIAA0119; HAKRB; HAKRe; trans-1,2-dihydrobenzene-1,2-diol dehydrogenase; chlordecone reductase homolog; dihydrodiol dehydrogenase 3; prostaglandin F synthase; ALDO-KETO REDUCTASE B; 3- | HYFNSDSFAS HPNYPYSDE Y (312) | N/A | N/A | 1:150-1:300 |
| S0332 | aldo-keto reductase family 1, member C4 (dihydrodiol dehydrogenase 1; 20-alpha (3-alpha)-hydroxy- | 1645 | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reduc- | RYVVMDFLM DHPDYPFSD EY (313) | N/A | N/A | 1:300-1:400 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | steroid dehydrogenase) | | tase C; 20 alpha-hydroxysteroid dehydrogenase; hepatic dihydrodiol | | | | |
| S0332-x1 | aldo-keto reductase family 1, member C4 (dihydrodiol dehydrogenase 1; 20-alpha (3-alpha)-hydroxysteroid dehydrogenase) | 1645 | 1.1.1.213; 2-ALPHA-HSD; 1.3.1.20; 20-ALPHA-HSD; MGC8954; H-37; HAKRC; MBAB; C9; DDH1; AKR1C1; trans-1,2-dihydrobenzene-1,2-diol dehydrogenase; chlordecone reductase homolog; aldo-keto reductase C; 20 alpha-hydroxysteroid dehydrogenase; hepatic dihydrodiol | RYVVMDFLM DHPDYPFSD EY (314) | N/A | N/A | 1:75-1:150 |
| S0336 | chromosome 20 open reading frame 139 | 140809 | C20orf139; chromosome 20 open reading frame 139 | DPAKVQSLV DTIREDPD (315) | RETIPAKLV QSTLSDLR (316) | N/A | 1:1600-1:2400 |
| S0342 | solute carrier family 2 (facilitated glucose transporter), member 12 | 154091 | SLC2A12; solute carrier family 2 (facilitated glucose transporter), member 12 | SDTTEELTVIK SSLKDE (317) | N/A | N/A | 1:400-1:1250 |
| S0343 | solute carrier family 2 (facilitated glucose transporter), member 12 | 154091 | SLC2A12; solute carrier family 2 (facilitated glucose transporter), member 12 | HSRSSLMPLR NDVDKR (318) | N/A | N/A | 1:50-1:125 |
| S0357 | HTPAP protein | 84513 | HTPAP; HTPAP protein | YRNPYVEAE YFPTKPMFVI A (319) | N/A | N/A | 1:100-1:300 |
| S0364 | KIAA0746 protein | 23231 | KIAA0746; KIAA0746 protein | KKFPRFRNRE LEATRRQRM D (320) | N/A | N/A | 1:200-1:300 |
| S0367 | peroxisomal acyl-CoA thioesterase 2B | 122970 | PTE2B; peroxisomal acyl-CoA thioesterase 2B | SGNTAINYKH SSIP (321) | N/A | N/A | 1:200-1:600 |
| S0374 | chloride intracellular channel 5 | 53405 | CLIC5; chloride intracellular channel 5 | DANTCGEDK GSRRKFLDG DE (322) | N/A | N/A | 1:5000-1:9000 |
| S0380 | keratinocyte associated protein 3 | 200634 | KRTCAP3; keratinocyte associated protein 3 | QLEEMTELES PKCKRQENE Q (323) | N/A | N/A | 1:2000-1:9000 |
| S0384 | FERM, RhoGEF (ARHGEF) and pleckstrin domain protein 1 (chondrocyte-derived) | 10160 | p63RhoGEF; CDEP; FARP1; chondrocyte-derived ezrin-like protein; FERM, RhoGEF, and pleckstrin domain protein 1; FERM, ARHGEF, AND PLECKSTRIN DOMAIN-CONTAINING PROTEIN 1; FERM, RhoGEF (ARHGEF) and pleckstrin domain protein 1 (chondrocyte-derived) | QADGAASAP TEEEEEVVKD R (324) | N/A | N/A | 1:100 |
| S0388 | trichorhinophalangeal syndrome I | 7227 | GC79; TRPS1; TRPS1 GENE; trichorhinophalangeal syndrome I; zinc finger transcription factor TRPS1 | SGDSLETKED QKMSPKATE E (325) | N/A | N/A | 1:600 |
| S0396 | cytochrome, P450, family 3, subfamily A, polypeptide 4 | 1576 | 1.14.14.1; HLP; CYP3A3; CYP3A4; P450C3; NF-25; CP33; CP34; P450-III, STEROID-INDUCIBLE; nifedipine oxidase; glucocorticoid-inducible P450; | RKSVKRMKE SRLEDTQKH RV (326) | N/A | N/A | 1:15 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | | | CYTOCHROME P450PCN1; P450, FAMILY III; P450-III, steroid inducible; cytochrome P450, subfamily IIIA, polypeptide 4; | | | | |
| S0398 | FAT tumor suppressor homolog 1 (Drosophila) | 2195 | CDHF7; FAT; cadherin ME5; FAT tumor suppressor precursor; cadherin-related tumor suppressor homolog precursor; cadherin family member 7 precursor; homolog of Drosophila Fat protein precursor; FAT tumor suppressor homolog 1 (Drosophila); FAT TUMOR SUPPRESS | KIRLPEREKP DRERNARRE P (327) | N/A | N/A | 1:45-1:200 |
| S0401 | granulin | 2896 | ACROGRANIN; PROEPITHELIN; PROGRANULIN; PEPI; PCDGF; granulin; GRN; EPITHELIN PRECURSOR | RGTKCLRRE APRWDAPLR DP (328) | N/A | N/A | 1:600-1:3000 |
| S0404 | N-myc downstream regulated gene 1 | 10397 | HMSNL; TARG1; CMT4D; RTP; PROXY1; NDRG1; GC4; NMSL; TDD5; RIT42; NDR1; differentiation-related gene 1 protein; nickel-specific induction protein Cap43; protein regulated by oxygen-1; NMYC DOWNSTREAM-REGULATED GENE 1; reducing agents and tunicamycin-respon | GTRSRSHTS EGTRSRSHT SE (329) | N/A | N/A | 1:100-1:900 |
| S0411 | fatty acid binding protein 5 (psoriasis-associated) | 2171 | PAFABP; EFABP; E-FABP; FABP5; PA-FABP; FATTY ACID-BINDING PROTEIN, EPIDERMAL; FATTY ACID-BINDING PROTEIN 5; FATTY ACID-BINDING PROTEIN, PSORIASIS-ASSOCIATED; fatty acid binding protein 5 (psoriasis-associated) | EETTADGRKT QTVCNFTD (330) | N/A | N/A | 1:1800 |
| S0413 | cyclin-dependent kinase inhibitor 1C (p57, Kip2) | 1028 | WBS; p57(KIP2); BWCR; CDKN1C; BWS; Beckwith-Wiedemann syndrome; cyclin-dependent kinase inhibitor 1C (p57, Kip2) | AKRKRSAPE KSSGDVP (331) | N/A | N/A | 1:2700 |
| S0414 | alpha-methyl-acyl-CoA racemase | 23600 | AMACR; 5.1.99.4; ALPHA-METHYL-ACYL-CoA RACEMASE; AMACR DEFICIENCY; AMACR ALPHA-METHYL-ACYL-CoA RACEMASE DEFICIENCY; alpha-methylacyl-CoA racemase isoform 1; alpha-methylacyl-CoA racemase isoform 2 | RVDRPGSRY DVSRLGRGK RS (332) | N/A | N/A | 1:100 |
| S0415 | gamma-aminobutyric acid (GABA) A receptor, beta 3 | 2562 | MGC9051; GABRB3; GABA-A RECEPTOR, BETA-3 POLYPEPTIDE; GAMMA-AMINOBUTYRIC ACID RECEPTOR, BETA-3; gamma-aminobutyric acid (GABA) A receptor, beta 3; gamma-aminobutyric acid (GABA) A receptor, beta 3 isoform 2 precursor; gamma-aminobutyric acid (GABA) A rece | ETVDKLLKGY DIRLRPD (333) | N/A | N/A | 1:600-1:1800 |
| S0417 | HSV-1 stimulation-related gene 1 | 22879 | HSRG1; KIAA0872; HSV-1 stimulation-related 1; HSV-1 stimulation-related gene 1 | APGGAEDLE DTQFPSEEAR E (334) | N/A | N/A | 1:9000 |
| S0425 | tumor necrosis factor receptor superfamily, | 27242 | TNFRSF21; DR6; BM-018; TNFR-related death receptor 6; tumor necrosis factor receptor | RKSSRTLKKG PRQDPSAIVE (335) | N/A | N/A | 1:9000 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | member 21 | | superfamily, member 21; tumor necrosis factor receptor superfamily, member 21 precursor | | | | |
| S0429 | jumonji domain containing 1C | 221037 | JMJD1C; TRIP8; jumonji domain containing 1C; THYROID HORMONE RECEPTOR INTERACTOR 8 | GSESGDSDE SESKSEQRTK R (336) | N/A | N/A | 1:1200 |
| S0432 | chromosome 9 open reading frame 140 | null | C9orf140; chromosome 9 open reading frame 140 | EADSGDARR LPRARGERR RH (337) | N/A | N/A | 1:90- 1:300 |
| S0440 | cell division cycle 25B | 994 | 3.1.3.48; CDC25B; cell division cycle 25B; cell division cycle 25B isoform 4; cell division cycle 25B isoform 5; cell division cycle 25B isoform 1; cell division cycle 25B isoform 2; cell division cycle 25B isoform 3 | RLERPQDRD TPVQNKRRR S (338) | N/A | N/A | 1:350- 1:3600 |
| S0445 | laminin, beta 1 | 3912 | LAMB1; LAMININ, BETA-1; CUTIS LAXA-MARFANOID SYNDROME; laminin, beta 1; laminin, beta 1 precursor; LAMB1 NEONATAL CUTIS LAXA WITH MARFANOID PHENOTYPE | DRVEDVMME RESQFKEKQ E (339) | N/A | N/A | 1:600- 1:1800 |
| S0447 | papillary renal cell carcinoma (translocation- associated) | 5546 | TPRC; MGC17178; MGC4723; PRCC; proline-rich protein PRCC; RCCP1 PRCC/TFE3 FUSION GENE; papillary renal cell carcinoma (translocation-associated); RENAL CELL CARCINOMA, PAPIL- LARY, 1 GENE; papillary renal cell carcinoma translocation- associated gene product | DEAFKRLQG KRNRGREE (340) | N/A | N/A | 1:4000- 1:6000 |
| S0455 | tumor necrosis factor (ligand) superfamily, member 10 | 8743 | APO2L; TL2; Apo-2L; TNFSF10; Apo-2 ligand; APO2 LIGAND; TNF-RELATED APOPTOSIS-INDUCING LIGAND; TNF-related apoptosis inducing ligand TRAIL; tumor necrosis factor (ligand) superfamily, member 10; TUMOR NECROSIS FACTOR LIGAND SUPER- FAMILY, MEMBER 10 | RFQEEIKENT KNDKQ (341) | N/A | N/A | 1:900 |
| S0459 | titin | 7273 | connectin; TMD; titin; CMD1G; CMPD4; TTN; FLJ32040; CMH9, included; titin isoform N2-A; titin isoform N2-B; titin iso- form novex-1; titin isoform novex-2; titin isoform novex- 3; cardiomyopathy, dilated 1G (autosomal dominant); TTN CARDIOMYOPATHY, FAMILIAL | KRDKEGVRW TKCNKKTLTD (342) | N/A | N/A | 1:2700- 1:8100 |
| S0469 | DNA fragmenta- tion factor, 45 kDa, alpha poly- peptide | 1676 | DFF45; DFF1; DFFA; ICAD; DFF- 45; INHIBITOR OF CASPASE- ACTIVATED DNase; DNA FRAGMEN- TATION FACTOR, 45-KD, ALPHA SUBUNIT; DNA fragmentation factor, 45 kDa, alpha poly- peptide; DNA fragmentation factor, 45 kD, alpha subunit; DNA fragmentation factor, 45 kD, alp | KEGSLLSKQE ESKAAFGEE (343) | N/A | N/A | 1:600 |
| S0494 | caspase 2, apoptosis- related cysteine protease (neural precursor cell | 835 | ICH-1L/1S; CASP2; ICH1; CASP- 2; ICH-1 protease; caspase 2 isoform 3; caspase 2 isoform 4; NEDD2 apoptosis regulatory gene; caspase 2 isoform 2 pre- | ESDAGKEKLP KMRLPTRSD (344) | N/A | N/A | 1:2000 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | expressed, developmentally down-regulated 2) | | cursor; caspase 2 isoform 1 preproprotein; NEURAL PRECURSOR CELL EXPRESSED, DEVELOPMENTALLY DOWNREGULATED 2; | | | | |
| S0501 | G1 to S phase transition 1 | 2935 | GSPT1; eRF3a; ETF3A; GST1, YEAST, HOMOLOG OF; PEPTIDE CHAIN RELEASE FACTOR 3A; G1- TO S-PHASE TRANSITION 1; G1 to S phase transition 1 | ERDKGKTVE VGRAYFETEK (345) | N/A | N/A | 1:15000 |
| S0502 | GCN5 general control of amino-acid synthesis 5-like 2 (yeast) | 2648 | hGCN5; GCN5L2; GCN5 (general control of amino-acid synthesis, yeast, homolog)-like 2; GCN5 general control of amino-acid synthesis 5-like 2 (yeast); General control of amino acid synthesis, yeast, homolog-like 2 | EKFRVEKDKL VPEKR (346) | N/A | N/A | 1:9000 |
| S0503 | geminin, DNA replication inhibitor | 51053 | GMNN; geminin, DNA replication inhibitor | EVAEKRRKAL YEALKENEK (347) | N/A | N/A | 1:333 |
| S0507 | ADP-ribosylation factor-like 6 interacting protein 2 | 64225 | ARL6IP2; ADP-ribosylation factor-like 6 interacting protein 2 | ENYEDDDLV NSDEVMKKP (348) | N/A | N/A | 1:8000-1:9000 |
| S0511 | DNA replication complex GINS protein PSF2 | 51659 | Pfs2; DNA replication complex GINS protein PSF2 | PKADEIRTLV KDMWDTR (349) | N/A | N/A | 1:2000 |
| S0524 | ankyrin repeat domain 10 | 55608 | ANKRD10; ankyrin repeat domain 10 | RKRCLEDSE DFGVKKARTE (350) | N/A | N/A | 1:4500 |
| S0527 | potassium channel tetramerisation domain containing 2 | null | KCTD2; potassium channel tetramerisation domain containing 2 | EPKSFLCRLC CQEDPELDS (351) | N/A | N/A | 1:900-1:1500 |
| S0528 | rabconnectin-3 | 23312 | RC3; KIAA0856; rabconnectin-3 | EEYDRESKS SDDVDYRGS (352) | N/A | N/A | 1:350-1:1200 |
| S0538 | acidic (leucine-rich) nuclear phosphoprotein 32 family, member E | 81611 | ANP32E; acidic (leucine-rich) nuclear phosphoprotein 32 family, member E | CVNGEIEGLN DTEKELEF (353) | N/A | N/A | 1:1200 |
| S0544 | chromosome 9 open reading frame 100 | 84904 | C9orf100; chromosome 9 open reading frame 100 | EQRARWERK RACTARE (354) | N/A | N/A | 1:40-1:240 |
| S0545 | Hpall tiny fragments locus 9C | 27037 | D22S1733E; HTF9C; Hpall tiny fragments locus 9C; Hpall tiny fragments locus 9C isoform2; Hpall tiny fragments locus 9C isoform 1 | ERKQLECEQ VLQKLAKE (355) | N/A | N/A | 1:900-1:5400 |
| S0546 | cell division cycle associated 2 | 157313 | CDCA2; cell division cycle associated 2 | RNSETKVRR STRLQKDLEN (356) | N/A | N/A | 1:1200 |
| S0553 | mitotic phosphoprotein 44 | 129401 | MP44; NUP35; LOC129401; NUCLEOPORIN, 35-KD; mitotic phosphoprotein 44 | SDYQVISDRQ TPKKDE (357) | N/A | N/A | 1:3000-1:5400 |
| S0557 | SMC4 structural maintenance of chromosomes 4-like 1 (yeast) | 10051 | SMC4L1; CAPC; hCAP-C; chromosome-associated polypeptide C; SMC4 (structural maintenance of chromosomes 4, yeast)-like | DIEGKLPQTE QELKE (358) | N/A | N/A | 1:200 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | | | 1; SMC4 structural maintenance of chromosomes 4-like 1 (yeast); structural maintenance of chromosomes (SMC) family member, chromosome-ass | | | | |
| S0564 | phosphatidylserine synthase 1 | 9791 | KIAA0024; PSSA; PTDSS1; phosphatidylserine synthase 1 | DDVNYKMHF RMINEQQVE D (359) | N/A | N/A | 1:1000-1:8000 |
| S0565 | polo-like kinase 1 (*Drosophila*) | 5347 | 2.7.1.-; PLK1; STPK13; polo-like kinase (*Drosophila*); polo (*Drosophia*)-like kinase; SERINE/THREONINE PROTEIN KINASE 13; polo-like kinase 1 (*Drosophila*) | ENPLPERPRE KEEPVVR (360) | N/A | N/A | 1:10-1:100 |
| S0567 | Pirin | 8544 | Pirin; PIR | REQSEGVGA RVRRSIGRPE (361) | N/A | N/A | 1:240 |
| S0578 | ATP-binding cassette, sub-family A(ABC1), member 3 | 21 | ABCA3; ABC3; LBM180; ABC-C; EST111653; ABC transporter 3; ATP-binding cassette 3; ATP-BINDING CASSETTE TRANSPORTER 3; ATP-BINDING CASSETTE, SUBFAMILY A, MEMBER 3; ATP-binding cassette, sub-family A member 3; ATP-binding cassette, subfamily A (ABC1), memb | PRAVAGKEE EDSDPEKALR (362) | N/A | N/A | 1:1500 |
| S0579 | ATP-binding cassette, sub-family A (ABC1), member 7 | 10347 | ABCX; ABCA7; ABCA-SSN; autoantigen SS-N; macrophage ABC transporter; SJOGREN SYNDROME ANTIGEN SS-N; ATP-BINDING CASSETTE, SUBFAMILY A, MEMBER 7; ATP-binding cassette, sub-family A (ABC1), member 7; ATP-binding cassette, sub-family A, member 7 isoform a; A | EKADTDMEG SVDTRQEK (363) | N/A | N/A | 1:300-1:400 |
| S0581 | ATP-binding cassette, sub-family B (MDR/TAP), member 7 | 22 | ABCB7; Atm1p; ASAT; ABC7; E5T140535; ABC TRANSPORTER 7; ATP-binding cassette 7; ATP-BINDING CASSETTE TRANSPORTER 7; Anemia, sideroblastic, with spinocerebellar ataxia; ATP-BINDING CASSETTE, SUBFAMILY B, MEMBER 7; ATP-binding cassette, sub-family B, member | RVQNHDNPK WEAKKENISK (364) | N/A | N/A | 1:4000-1:10000 |
| S0585 | ATP-binding cassette, sub-family C (CFTR/MRP), member 12 | 94160 | MRP9; ABCC12; MULTIDRUG RESISTANCE-ASSOCIATED PROTEIN 9; ATP-BINDING CASSETTE, SUBFAMILY C, MEMBER 12; ATP-binding cassette, sub-family C (CFTR/MRP), member 12 | RSPPAKGAT GPEEQSDSL K (365) | N/A | N/A | 1:500 |
| S0586 | ATP-binding cassette, sub-family G (WHITE), member 2 | 9429 | ABC15; MXR1; ABCP; EST157481; MRX; ABCG2; BCRP1; BMDP; MITOXANTRONE-RESISTANCE PROTEIN; mitoxantrone resistance protein; placenta specific MDR protein; ATP-BINDING CASSETTE TRANSPORTER, PLACENTA-SPECIFIC; breast cancer resistance protein; ATP-BINDING CASS | REEDFKATEII EPSKQDKP (366) | N/A 1:400 | NA | 1:333- |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0593 | solute carrier organic anion transporter family, member 1B3 | 28234 | OATP1B3; SLC21A8; OATP8; SLCO1B3; ORGANIC ANION TRANSPORTER 8; solute carrier organic anion transporter family, member 1B3; SOLUTE CARRIER FAMILY 21, MEMBER 8 (ORGANIC ANION TRANSPORTER); solute carrier family 21 (organic anion transporter), member 8 | DKTCMKWST NSCGAQ (367) | N/A | N/A | 1:500-1:2400 |
| S0597 | solute carrier family 22 (organic anion transporter), member 6 | 9356 | ROAT1; MGC45260; HOAT1; PAHT; SLC22A6; PAH TRANSPORTER; para-aminohippurate transporter; renal organic anion transporter 1; solute carrier family 22 member 6 isoform b; solute carrier family 22 member 6 isoform c; solute carrier family 22 member 6 isoform | DANLSKNGG LEVWL (368) | N/A | N/A | 1:3000 |
| S0604 | solute carrier family 35 (UDP-galactose transporter), member A2 | 7355 | UGT2; UGTL; UGAT; SLC35A2; UGT1; UDP-galactose translocator; UDP-GALACTOSE TRANSPORTER, ISOFORM 2; UGALT UDP-GALACTOSE TRANSPORTER, ISOFORM 1; solute carrier family 35 (UDP-galactose transporter), member A2; solute carrier family 35 (UDP-galactose transpo | EPFLPKLLTK (369) | N/A | N/A | 1:2400 |
| S0607 | cell division cycle 25B | 994 | 3.1.3.48; CDC25B; cell division cycle 25B; cell division cycle 25B isoform 4; cell division cycle 25B isoform 5; cell division cycle 25B isoform 1; cell division cycle 25B isoform 2; cell division cycle 25B isoform 3 | RKSEAGSGA ASSSGEDKE N (370) | N/A | N/A | 1:1800 |
| S0609 | stearoyl-CoA desaturase (delta-9-desaturase) | 6319 | SCD; acyl-CoA desaturase; stearoyl-CoA desaturase (delta-9-desaturase); fatty acid desaturase | DDIYDPTYKD KEGPSPKVE (371) | N/A | N/A | 1:2000-1:5000 |
| S0611 | mitogen-activated protein kinase 12 | 6300 | SAPK3; p38gamma; SAPK-3; p38-GAMMA; PRKM12; MAPK12; ERK3; ERK6; EXTRACELLULAR SIGNAL-REGULATED KINASE 6; mitogen-activated protein kinase 3; stress-activated protein kinase 3; mitogen-activated protein kinase 12 | QSDEAKNNM KGLPELEKKD (372) | N/A | N/A | 1:100 |
| S0612 | nuclear factor of kappa light polypeptide gene enhancer in B-cells 2 (p49/p100) | 4791 | LYT-10; LYT10; NFKB2; ONCOGENE LYT 10; TRANSCRIPTION FACTOR NFKB2; NFKB, p52/p100 SUBUNIT; LYMPHOCYTE TRANSLOCATION CHROMOSOME 10; NUCLEAR FACTOR KAPPA-B, SUBUNIT 2; Nuclear factor of kappa light chain gene enhancer in B-cells 2; nuclear factor of kappa I | SRPQGLTEAE QRELEQEAK (373) | N/A | N/A | 1:4500 |
| S0613 | tumor necrosis factor receptor superfamily, member 5 | 958 | Bp50; TNFRSF5; MGC9013; CDW40; CD40 antigen; CD40L receptor; B CELL-ASSOCIATED MOLECULE CD40; CD40 type II isoform; B cell surface antigen CD40; nerve growth factor receptor-related B-lymphocyte activation molecule; tumor necrosis factor receptor superfam | RVQQKGTSE TDTIC (374) | N/A | N/A | 1:250-1:270 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0614 | Epstein-Barr virus induced gene 3 | 10148 | EBI3; IL27, EBI3 SUBUNIT; EPSTEIN-BARR VIRUS-INDUCED GENE 3; INTERLEUKIN 27, EBI3 SUBUNIT; Epstein-Barr virus induced gene 3; Epstein-Barr virus induced gene 3 precursor | VRLSPLAERQ LQVQWE (375) | N/A | N/A | 1:1200-1:3000 |
| S0616 | zinc finger protein 339 | 58495 | ZNF339; zinc finger protein 339 | RRSLGVSVR SWDELPDEK R (376) | N/A | N/A | 1:2500 |
| S0617 | DAB2 interacting protein | 153090 | DAB2IP; DAB2 interacting protein | DEGLGPDPP HRDRLRSK (377) | N/A | N/A | 1:600 |
| S0618 | protein tyrosine phosphatase, receptor type, f polypeptide (PTPRF), interacting protein (liprin), alpha 1 | 8500 | MGC26800; LIP1; PPFIA1; LIP 1; LAR-interacting protein 1; PTPRF interacting protein alpha 1 isoform a; PTPRF interacting protein alpha 1 isoform b; protein tyrosine phosphatase, receptor type, f polypeptide (PTPRF), interacting protein (liprin), alpha 1 | SGKRSSDGS LSHEEDLAK (378) | N/A | N/A | 1:150 |
| S0631 | RGM domain family, member A | 56963 | RGMA; REPULSIVE GUIDANCE MOLECULE; RGM domain family, member A | SQERSDSPEI CHYEKSFHK (379) | N/A | N/A | 1:600 |
| S0633 | hypothetical protein LOC144347 | 144347 | LOC144347; hypothetical protein LOC144347 | KVNPEPTHEI RCNSEVK (380) | N/A | N/A | 1:100-1:200 |
| S0639 | tetratricopeptide repeat domain 7 | 57217 | TTC7; tetratricopeptide repeat domain 7 | RELREVLRTV ETKATQN (381) | N/A | N/A | 1:2000-1:3000 |
| S0640 | protein C (inactivator of coagulation factors Va and VIIIa) | 5624 | PROC; 3.4.21.69; PROC DEFICIENCY PROTEIN C; THROMBOPHILIA, HEREDITARY, DUE TO PC DEFICIENCY; PROTEIN C DEFICIENCY, CONGENITAL THROMBOTIC DISEASE DUE TO; protein C (inactivator of coagulation factors Va and VIIIa) | RDTEDQEDQ VDPRLIDGK (382) | N/A | N/A | 1:1000-1:1800 |
| S0643 | transducin-like enhancer of split 3 (E(sp1) homolog, Drosophila) | 7090 | HsT18976; KIAA1547; ESG3; TLE3; transducin-like enhancer protein 3; enhancer of split groucho 3; transducin-like enhancer of split 3 (E(sp1) homolog, Drosophila) | KNHHELDHR ERESSAN (383) | N/A | N/A | 1:200-1:1440 |
| S0645 | frizzled homolog 7 (Drosophila) | 8324 | FzE3; FZD7; frizzled 7; frizzled homolog 7 (Drosophila); Frizzled, drosophila, homolog of, 7 | SDGRGRPAF PFSCPRQ (384) | N/A | N/A | 1:900 |
| S0646 | solute carrier family 3 (activators of dibasic and neutral amino acid transport), member 2 | 6520 | MDU1; 4T2HC; SLC3A2; NACAE; 4F2HC; 4F2 HEAVY CHAIN; CD98 HEAVY CHAIN; CD98 MONOCLONAL ANTIBODY 44D7; ANTIGEN DEFINED BY MONOCLONAL ANTIBODY 4F2, HEAVY CHAIN; antigen identified by monoclonal antibodies 4F2, TRA1.10, TROP4, and T43; SOLUTE CARRIER FAMILY 3 | GSKEDFDSLL QSAKK (385) | N/A | N/A | 1:3600-1:5400 |
| S0648 | KIAA0738 gene product | 9747 | KIAA0738; KIAA0738 gene product | EYRNQTNLPT ENVDK (386) | N/A | N/A | 1:200 |
| S0651 | phospholipase A2 receptor 1, 180 kDa | 22925 | PLA2IR; PLA2-R; PLA2R1; PLA2G1R; PHOSPHOLIPASE A2 RECEPTOR, 180-KD; phospholipase A2 receptor 1, 180 kDa | QKEEKTWHE ALRSCQADN (387) | N/A | N/A | 1:3600 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S0654 | KIAA0182 protein | 23199 | KIAA0182; KIAA0182 protein | EKAEEGPRK REPAPLDK (388) | N/A | N/A | 1:400 |
| S0659 | thymidine kinase 2, mitochondrial | 7084 | TK2; THYMIDINE KINASE, MITOCHONDRIAL; thymidine kinase 2, mitochondrial | EQNRDRILTP ENRK (389) | N/A | N/A | 1:300 |
| S0663 | chromosome 14 open reading frame 135 | 64430 | C14orf135; chromosome 14 open reading frame 135 | RDWYIGLVSD EKWK (390) | N/A | N/A | 1:900 |
| S0665 | KIAA1007 protein | 23019 | KIAA1007; KIAA1007 protein; adrenal gland protein AD-005; KIAA1007 protein isoform a; KIAA1007 protein isoform b | DSYLKTRSPV TFLSDLR (391) | N/A | N/A | 1:1500-1:3000 |
| S0670 | DKFZP566O1646 protein | 25936 | DC8; DKFZP566O1646 protein | KCRGETVAK EISEAMKS (392) | N/A | N/A | 1:900 |
| S0672 | B-cell CLL/lymphoma 7A | 605 | BCL7A; B-cell CLL/lymphoma-7; B-cell CLL/lymphoma 7A | QRGSQIGRE PIGLSGD (393) | N/A | N/A | 1:800 |
| S0673 | likely ortholog of mouse nin one binding protein | 28987 | ART-4; NOB1P; adenocarcinoma antigen recognized by T lymphocytes 4; likely ortholog of mouse nin one binding protein | KPPQETEKG HSACEPEN (394) | N/A | N/A | 1:50 |
| S0676 | guanine nucleotide binding protein (G protein) alpha 12 | 2768 | RMP; NNX3; GNA12; GUANINE NUCLEOTIDE-BINDING PROTEIN, ALPHA-12; guanine nucleotide binding protein (G protein) alpha 12 | ERRAGSGAR DAERE (395) | N/A | N/A | 1:1200-1:2400 |
| S0677 | GrpE-like 1, mitochondrial (E. coli) | 80273 | HMGE; GRPEL1; HUMAN MITOCHONDRIAL GrpE PROTEIN; GrpE-like 1, mitochondrial (E. coli); GrpE, E. COLI, HOMOLOG OF, 1 | SEQKADPPAT EKTLLE (396) | N/A | N/A | 1:500-1:1000 |
| S0684 | hypothetical protein FLJ34922 | 91607 | FLJ34922; hypothetical protein FLJ34922 | EAEWSQGVQ GTLRIKKYLT (397) | N/A | N/A | 1:8100 |
| S0687 | hypothetical protein FLJ20457 | 54942 | FLJ20457; hypothetical protein FLJ20457 | EESKSITEGL LTQKQYE (398) | N/A | N/A | 1:600-1:1260 |
| S0691 | solute carrier family 7, (cationic amino acid transporter, y+ system) member 11 | 23657 | CCBR1; SLC7A11; xCT; cystine/glutamate transporter; SYSTEM Xc(-) TRANSPORTER-RELATED PROTEIN; SOLUTE CARRIER FAMILY 7, MEMBER 11; solute carrier family 7, (cationic amino acid transporter, y+ system) member 11 | QNFKDAFSG RDSSITR (399) | N/A | N/A | 1:1000-1:1575 |
| S0692 | glutamate-cysteine ligase, catalytic subunit | 2729 | GLCLC; GCLC; 6.3.2.2; GCS; GAMMA-GLUTAMYLCYSTEINE SYNTHETASE, CATALYTIC SUBUNIT; glutamate-cysteine ligase, catalytic subunit | EKIHLDDANE SDHFEN (400) | N/A | N/A | 1:100-1:400 |
| S0695 | integrin, beta 4 | 3691 | ITGB4; INTEGRIN, BETA-4; integrin, beta 4 | TEDVDEFRNK LQGER (401) | N/A | N/A | 1:2700-1:4050 |
| S0702 | solute carrier family 7 (cationic amino acid transpor- | 8140 | SLC7A5; MPE16; D165469E; CD98; LAT1; 4F2 light chain; Membrane protein E16; L-TYPE AMINO ACID TRANSPORTER 1; | KGDVSNLDP NFSFEGTKLD V (402) | N/A | N/A | 1:21160-1:178200 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | ter, y⁺ system), member 5 | | Solute carrier family 7, member 5; solute carrier family 7 (cationic amino acid transporter, y⁺ system), member 5 | | | | |
| S0705 | breast cancer metastasis suppressor 1 | 25855 | DKFZp564A063; BRMS1; breast cancer metastasis-suppressor 1; breast cancer metastasis suppressor 1 | KARAAVSPQ KRKSDGP (403) | N/A | N/A | 1:1000-1:2000 |
| S0706 | KiSS-1 metastasis-suppressor | 3814 | MGC39258; KISS1; KiSS-1 metastasis-suppressor; KISS 1 METASTIN; malignant melanoma metastasis-suppressor; KISS1 METASTASIS SUPPRESSOR | RQIPAPQGAV LVQREKD (404) | N/A | N/A | 1:180 |
| S0708 | cofactor required for Sp1 transcriptional activation, subunit 3, 130 kDa | 9439 | DKFZp434H0117; CRSP133; SUR2; DRIP130; CRSP3; mediator; transcriptional co-activator CRSP130; CRSP, 130-KD SUBUNIT; CRSP 130-kD subunit; 133 kDa transcriptional co-activator; 130 kDa transcriptional co-activator; vitamin D3 receptor interacting protein; c | SVKEQVEKIIC NLKPALK (138) | N/A | N/A | 1:2430 |
| S5002 | keratin 14 (epidermolysis bullosa simplex, Dowling-Meara, Koebner) | 3861 | CK; KRT14; K14; EBS4; EBS3; cytokeratin 14; CK 14; KERATIN, TYPE I CYTOSKELETAL 14; keratin 14 (epidermolysis bullosa simplex, Dowling-Meara, Koebner) | Antibody obtained from Chemicon | | | 1:50 |
| S5003 | keratin 17 | 3872 | PCHC1; PC; PC2; 39.1; KRT17; K17; CYTOKERATIN 17; VERSION 1; CK 17; KERATIN, TYPE I CYTOSKELETAL 17 | Antibody obtained from Dako | | | 1:10-1:25 |
| S5004 | keratin 18 | 3875 | K18; CYK18; KRT18; CYTOKERATIN 18; CK 18; KERATIN, TYPE I CYTOSKELETAL 18 | Antibody obtained from Dako | | | 1:200-1:400 |
| S5005 | keratin 18 | 3875 | K18; CYK18; KRT18; CYTOKERATIN 18; CK 18; KERATIN, TYPE I CYTOSKELETAL 18 | Antibody obtained from Becton Dickinson | | | 1:50-1:100 |
| S5012 | tumor-associated calcium signal transducer 1 | 4072 | TROP1; LY74; Ep-CAM; GA733-2; EGP40; MK-1; CO17-1A; EPCAM; M4S1; KSA; TACSTD1; EGP; MK-1 antigen; EPITHELIAL CELLULAR ADHESION MOLECULE; GASTRO-INTESTINAL TUMOR-ASSOCIATED ANTIGEN 2, 35-KD GLYCOPROTEIN; tumor-associated calcium signal transducer 1 precurso | Antibody obtained from Oncogene Research Products (Calbiochem) | | | 1:40 |
| S5014 | estrogen receptor 2 (ER beta) | 2100 | ER-BETA; ESR-BETA; ESR2; Erb; ESRB; NR3A2; ESTROGEN RECEPTOR, BETA; estrogen receptor 2 (ER beta) | Antibody obtained from Oncogene Research Products (Calbiochem) | | | 1:2500 |
| S5038 | mucin 1, transmembrane | 4582 | PEMT; MUC1; episialin; EMA; PUM; H23AG; CD227; PEM; CARCINOMA-ASSOCIATED MUCIN; H23 antigen; TUMOR-ASSOCIATED MUCIN; DF3 antigen; peanut-reactive urinary mucin; mucin 1, transmembrane; polymorphic epithelial mucin; MUCIN 1, URINARY; MUCIN, TUMOR-ASSOCIATE | Antibody obtained from Imperial Cancer Research Technology (ICRT) | | | 1:1 |
| S5044 | transferrin receptor | 7037 | P90; TR; TFRC; TFR; CD71; T9; TRFR; ANTIGEN CD71; TRANSFER- | Antibody obtained from NeoMarkers | | | 1:20 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | (p90, CD71) | | RIN RECEPTOR PROTEIN; transferrin receptor (p90, CD71) | | | | |
| S5045 | v-erb-b2 erythroblastic leukemia viral oncogene homolog 2, neuro/glioblastoma derived oncogene homolog (avian) | 2064 | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL | Antibody obtained from NeoMarkers | | | 1:600 |
| S5047 | major vault protein | 9961 | MVP; LRP; VAULT1; LUNG RESISTANCE-RELATED PROTEIN MAJOR VAULT PROTEIN, RAT, HOMOLOG OF | Antibody obtained from NeoMarkers | | | 1:300 |
| S5064 | tumor protein p73-like | 8626 | LMS; TP73L; KET; SHFM4; p73H; EEC3; TP63; p51; TUMOR PROTEIN p63; TUMOR PROTEIN p73-LIKE; p53-RELATED PROTEIN p63; tumor protein 63 kDa with strong homology to p53 | Antibody obtained from Dako | | | 1:50 |
| S5065 | estrogen receptor 1 | 2099 | ER; NR3A1; ESR1; Era; ESR; ER-ALPHA; ESRA; ESTRADIOL RECEPTOR; ESTROGEN RECEPTOR, ALPHA; estrogen receptor 1 (alpha) | Antibody obtained from Dako | | | 1:20 |
| S5066 | v-erb-b2 erythroblastic leukemia viral oncogene homolog 2, neuro/glioblastoma derived oncogene homolog (avian) | 2064 | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL | Antibody obtained from Dako | | | 1:300 |
| S5067 | cathepsin D (lysosomal aspartyl protease) | 1509 | CTSD; MGC2311; CPSD; EC 3.4.23.5; cathepsin D preproprotein; Cathepsin D precursor; cathepsin D (lysosomal aspartyl protease); | Antibody obtained from Dako | | | 1:20-1:50 |
| S5069 | CA 125 | n/a | | Antibody obtained from Dako | | | 1:20 |
| S5070 | CA 15-3 | n/a | | Antibody obtained from Dako | | | 1:50 |
| S5071 | CA 19-9 | n/a | | Antibody obtained from Dako | | | 1:50 |
| S5072 | v-myc myelocytomatosis viral oncogene homolog (avian) | 4609 | c-Myc; MYC; ONCOGENE MYC; Myc proto-oncogene protein; PROTOONCOGENE HOMOLOGOUS TO MYELOCYTOMATOSIS VIRUS; v-myc myelocytomatosis viral oncogene homolog (avian); v-myc avian myelocytomatosis viral oncogene homolog; Avian myelocytomatosis viral (v-myc) onco | Antibody obtained from Dako | | | 1:50 |
| S5073 | cadherin 1, type 1, E-cadherin (epithelial) | 999 | CDH1; Cadherin-1; Arc-1; ECAD; CDHE; Uvomorulin; LCAM; Epithelial-cadherin precursor; cell-CAM 120/80; CADHERIN, EPITHELIAL; calcium-dependent adhesion protein, epithelial; cadherin 1, E-cadherin (epithelial); cadherin 1, type 1 preproprotein; cadherin 1, | Antibody obtained from Dako | | | 1:100-1:150 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| S5074 | glutathione S-transferase pi | 2950 | GSTP1; DFN7; GSTP1-1; GST3; GSTPP; GST class-pi; glutathione transferase; EC 2.5.1.18; glutathione S-transferase pi; GST, CLASS PI; deafness, X-linked 7; GLUTATHIONE S-TRANSFERASE 3; GLUTATHIONE S-TRANSFERASE, PI; FAEES3 GLUTATHIONE S-TRANSFERASE PI PSEUD | Antibody obtained from Dako | | | 1:50 |
| S5075 | tumor protein p53 (Li-Fraumeni syndrome) | 7157 | p53; TP53; TRP53; PHOSPHOPROTEIN P53; TRANSFORMATION-RELATED PROTEIN 53; TUMOR SUPPRESSOR P53; CELLULAR TUMOR ANTIGEN P53; tumor protein p53 (Li-Fraumeni syndrome) | Antibody obtained from Dako | | | 1:50 |
| S5076 | progesterone receptor | 5241 | NR3C3; PR; PGR; PROGESTERONE RESISTANCE; PSEUDOCORPUS LUTEUM INSUFFICIENCY PROGESTERONE RECEPTOR | Antibody obtained from Dako | | | 1:50 |
| S5077 | trefoil factor 1 (breast cancer, estrogen-inducible sequence expressed in) | 7031 | | Antibody obtained from Dako | | | 1:50-1:100 |
| S5079 | enolase 2, (gamma, neuronal) | 2026 | NSE; ENO2; 2-phospho-D-glycerate hydro-lyase; ENOLASE, GAMMA; neurone-specific enolase; ENOLASE, NEURON-SPECIFIC; 2-phospho-D-glycerate hydrolyase; EC 4.2.1.11; Neural enolase; enolase-2, gamma, neuronal; neuron specific gamma enolase; enolase 2, (gamma, | Antibody obtained from Dako | | | 1:400 |
| S5080 | B-cell CLL/lymphoma 2 | 596 | BCL2; FOLLICULAR LYMPHOMA; APOPTOSIS REGULATOR BCL-2; B-cell CLL/lymphoma 2; B-cell ymphoma protein 2 alpha; B-cell lymphoma protein 2 beta; ONCOGENE B-CELL LEUKEMIA 2 LEUKEMIA, CHRONIC LYMPHATIC, TYPE 2 | Antibody obtained from Dako | | | 1:50 |
| S5081 | retinoblastoma 1 (including osteosarcoma) | 5925 | p105-Rb; PP110; Retinoblastoma-1; RB; RB1; RETINOBLASTOMA-ASSOCIATED PROTEIN; RB OSTEOSARCOMA, RETINOBLASTOMA-RELATED; retinoblastoma 1 (including osteosarcoma) | Antibody obtained from Dako | | | 1:20 |
| S5082 | synaptophysin | 6855 | SYP; Synaptophysin; Major synaptic vesicle protein P38 | Antibody obtained from Dako | | | 1:50 |
| S5083 | BCL2-associated X protein | 581 | BAX; BCL2-associated X protein; APOPTOSIS REGULATOR BAX, MEMBRANE ISOFORM ALPHA | Antibody obtained from Dako | | | 1:500 |
| S5086 | estrogen receptor 2 (ER beta) | 2100 | ER-BETA; ESR-BETA; ESR2; Erb; ESRB; NR3A2; ESTROGEN RECEPTOR, BETA; estrogen receptor 2 (ER beta) | Antibody obtained from Abcam | | | 1:200 |
| S5087 | mucin 1, transmembrane | 4582 | PEMT; MUC1; episialin; EMA; PUM; H23AG; CD227; PEM; CARCINOMA-ASSOCIATED MUCIN; H23 antigen; TUMOR-ASSOCIATED MUCIN; DF3 antigen; peanut- | Antibody obtained from Zymed | | | 1:200-1:1600 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | | | reactive urinary mucin; mucin 1, transmembrane; polymorphic epithelial mucin; MUCIN 1, URINARY; MUCIN, TUMOR-ASSOCIATE | | | | |
| S6001 | estrogen receptor 1 | 2099 | ER; NR3A1; ESR1; Era; ESR; ER-ALPHA; ESRA; ESTRADIOL RECEPTOR; ESTROGEN RECEPTOR, ALPHA; estrogen receptor 1 (alpha) | Antibody obtained from US Labs | | | 1:1 |
| S6002 | progesterone receptor | 5241 | NR3C3; PR; PGR; PROGESTERONE RESISTANCE; PSEUDOCORPUS LUTEUM INSUFFICIENCY PROGESTERONE RECEPTOR | Antibody obtained from US Labs | | | 1:1 |
| S6003 | v-erb-b2 erythroblastic leukemia viral oncogene homolog 2, neuro/ glioblastoma derived oncogene homolog (avian) | 2064 | HER-2; ERBB2; NGL; P185ERBB2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL | Antibody obtained from US Labs | | | 1:1 |
| S6004 | B-cell CLL/ lymphoma 2 | 596 | BCL2; FOLLICULAR LYMPHOMA; APOPTOSIS REGULATOR BCL-2; B-cell CLL/lymphoma 2; B-cell lymphoma protein 2 alpha; B-cell lymphoma protein 2 beta; ONCOGENE B-CELL LEUKEMIA 2 LEUKEMIA, CHRONIC LYMPHATIC, TYPE 2 | Antibody obtained from US Labs | | | 1:1 |
| S6005 | keratin 5 (epidermolysis bullosa simplex, Dowling-Meara/ Kobner/Weber-Cockayne types) | 3852 | KRT5; EBS2; Keratin-5; K5; CYTOKERATIN 5; CK 5; 58 KDA CYTOKERATIN; KERATIN, TYPE II CYTOSKELETAL 5; keratin 5 (epidermolysis bullosa simplex, Dowling-Meara/Kobner/ Weber-Cockayne types) | Antibody obtained from US Labs | | | 1:1 |
| S6006 | tumor protein p53 (Li-Fraumeni syndrome) | 7157 | p53; TP53; TRP53; PHOSPHOPROTEIN P53; TRANSFORMATION-RELATED PROTEIN 53; TUMOR SUPPRESSOR P53; CELLULAR TUMOR ANTIGEN P53; tumor protein p53 (Li-Fraumeni syndrome) | Antibody obtained from US Labs | | | 1:1 |
| S6007 | KI67 | n/a | | Antibody obtained from US Labs | | | 1:1 |
| S6008 | epidermal growth factor receptor (erythroblastic leukemia viral (v-erb-b) onco- gene homolog, avian) | 1956 | S7; EGFR; 2.7.1.112; ERBB; ONCOGENE ERBB; ERBB1 SPECIES ANTIGEN 7; V-ERB-B AVIAN ERYTHROBLASTIC LEUKEMIA VIRAL ONCOGENE HOMOLOG; epidermal growth factor receptor (avian erythroblastic leukemia viral (v-erb-b) oncogene homolog) | Antibody obtained from US Labs | | | 1:1 |
| S6011 | enolase 2, (gamma, neuronal) | 2026 | NSE; ENO2; 2-phospho-D-glycerate hydro-lyase; ENOLASE, GAMMA; neurone-specific enolase; ENOLASE, NEURN-SPECIFIC; 2-phospho-D-glycerate hydrolyase; EC 4.2.1.11; Neural enolase; enolase-2, gamma, neuronal; neuron specific gamma enolase; enolase 2, (gamma, | Antibody obtained from US Labs | | | 1:1 |
| S6012 | thyroid transcription | 7080 | benign chorea; chorea, hereditary benign; NK-2 (*Drosophila*) | Antibody obtained from US Labs | | | 1:1 |

Appendix A-continued

| AGI ID | GENE NAME | ENTREZ GENE ID | ALIASES | PEPTIDE 1 (SEQ ID NO.) | PEPTIDE 2 (SEQ ID NO.) | PEPTIDE 3 (SEQ ID NO.) | TITER |
|---|---|---|---|---|---|---|---|
| | factor 1 | | homolog A (thyroid nuclear factor); Thyroid transcription factor 1 (NK-2, *Drosophila*, homolog of, A); BCH; BHC; TEBP; TTF1; NKX2A; TTF-1; NKX2.1 | | | | |
| S6013 | v-erb-b2 erythroblastic leukemia viral oncogene homolog 2, neuro/ glioblastoma derived oncogene homolog (avian) | 2064 | HER-2; ERBB2; NGL; P185ERBB2; HER2; C-ERBB-2; NEU; MLN 19; EC 2.7.1.112; TKR1 HERSTATIN; NEU PROTO-ONCOGENE; ONCOGENE ERBB2; RECEPTOR PROTEIN-TYROSINE KINASE ERBB-2 PRECURSOR; ONCOGENE NGL, NEUROBLASTOMA- OR GLIOBLASTOMA-DERIVED; TYROSINE KINASE-TYPE CELL | Antibody obtained from US Labs | | | 1:1 |

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

We claim:

1. A method for selecting a chemotherapy for a breast cancer patient comprising steps of:
   providing a cancer sample from a breast cancer patient;
   detecting the presence of expression of TLE3 in the cancer sample; and
   selecting a taxane or taxane derivative for chemotherapy of the cancer patient when the TLE3 expression is present.

2. The method of claim 1, wherein the step of detecting comprises steps of:
   providing a negative control sample;
   detecting a level of TLE3 expression in the negative control sample;
   detecting a level of TLE3 expression in the cancer sample; and
   comparing the level of TLE3 expression in the cancer sample with the level of TLE3 expression in the negative control sample.

3. The method of claim 1, wherein the step of detecting comprises steps of:
   providing a positive control sample;
   detecting a level of TLE3 expression in the positive control sample;
   detecting a level of TLE3 expression in the cancer sample; and
   comparing the level of TLE3 expression in the cancer sample with the level of TLE3 expression in the positive control sample.

4. The method of claim 1, wherein the step of detecting comprises contacting the cancer sample with an interaction partner that binds a TLE3 polypeptide.

5. The method of claim 4, wherein the interaction partner is an antibody.

6. The method of claim 1, wherein the step of detecting comprises contacting the cancer sample with one or more primers that hybridize with a TLE3 polynucleotide.

7. The method of claim 6, wherein the taxane is paclitaxel.

8. The method of claim 6, wherein the taxane is docetaxel.

9. The method of claim 4, wherein the step of selecting comprises selecting a taxane for chemotherapy.

10. The method of claim 9, wherein the taxane is paclitaxel.

11. The method of claim 9, wherein the taxane is docetaxel.

12. The method of claim 5, wherein the step of selecting comprises selecting a taxane for chemotherapy.

13. The method of claim 12, wherein the taxane is paclitaxel.

14. The method of claim 12, wherein the taxane is docetaxel.

15. The method of claim 6, wherein the step of selecting comprises selecting a taxane for chemotherapy.

16. The method of claim 15, wherein the taxane is paclitaxel.

17. The method of claim 15, wherein the taxane is docetaxel.

* * * * *